US 8,246,934 B2

(12) United States Patent
Weers et al.

(10) Patent No.: US 8,246,934 B2
(45) Date of Patent: *Aug. 21, 2012

(54) RESPIRATORY DISPERSION FOR METERED DOSE INHALERS COMPRISING PERFORATED MICROSTRUCTURES

(75) Inventors: Jeffry G. Weers, Belmont, CA (US);
Ernest G. Schutt, San Diego, CA (US);
Luis A. Dellamary, San Marcos, CA (US); Thomas E. Tarara, Burlingame, CA (US); Alexey Kabalnov, Corvallis, OR (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/875,966

(22) Filed: Sep. 3, 2010

(65) Prior Publication Data

US 2010/0329984 A1   Dec. 30, 2010

Related U.S. Application Data

(62) Division of application No. 12/012,827, filed on Feb. 5, 2008, now Pat. No. 7,790,145.

(51) Int. Cl.
*A61K 9/00* (2006.01)
*A61K 9/12* (2006.01)
*A61K 9/14* (2006.01)

(52) U.S. Cl. .................... 424/46; 424/45; 424/489
(58) Field of Classification Search .............. 424/45, 424/46, 489
See application file for complete search history.

(56) References Cited

U.S. PATENT DOCUMENTS

| | | |
|---|---|---|
| 979,993 A | 10/1910 | O'Byrne et al. |
| 1,855,591 A | 4/1932 | Wallerstein |
| 2,457,036 A | 12/1948 | Epstein |
| 2,797,201 A | 6/1957 | Veatch et al. |
| 3,014,844 A | 12/1961 | Thiel et al. |
| 3,362,405 A | 1/1968 | Hazel |
| 3,555,717 A | 1/1971 | Chivers |
| 3,619,294 A | 11/1971 | Black et al. |
| 3,632,357 A | 1/1972 | Childs |
| 3,655,442 A | 4/1972 | Schwar et al. |
| 3,745,682 A | 7/1973 | Waldeisen |
| 3,812,854 A | 5/1974 | Michaels et al. |
| 3,948,263 A | 4/1976 | Drake, Jr. et al. |
| 3,957,964 A | 5/1976 | Grimm, III |
| 3,964,483 A | 6/1976 | Mathes |
| 3,975,512 A | 8/1976 | Long, Jr. |
| 4,009,280 A | 2/1977 | Macarthur et al. |
| 4,036,223 A | 7/1977 | Obert |
| 4,089,120 A | 5/1978 | Kozishek |
| 4,098,273 A | 7/1978 | Glenn |
| 4,102,999 A | 7/1978 | Umezawa et al. |
| 4,127,502 A | 11/1978 | Li Mutti et al. |
| 4,127,622 A | 11/1978 | Watanabe et al. |
| 4,158,544 A | 6/1979 | Louderback |
| 4,159,319 A | 6/1979 | Bachmann et al. |
| 4,161,516 A | 7/1979 | Bell |
| 4,180,593 A | 12/1979 | Cohan |
| 4,201,774 A | 5/1980 | Igarashi et al. |
| 4,211,769 A | 7/1980 | Okada et al. |
| 4,244,949 A | 1/1981 | Gupta |
| 4,253,468 A | 3/1981 | Lehmbeck |
| 4,281,031 A | 7/1981 | Hillman et al. |
| 4,326,524 A | 4/1982 | Drake, Jr. et al. |
| 4,327,076 A | 4/1982 | Puglia et al. |
| 4,327,077 A | 4/1982 | Puglia et al. |
| 4,358,442 A | 11/1982 | Wirtz-Peitz et al. |
| 4,371,557 A | 2/1983 | Oppy et al. |
| 4,397,799 A | 8/1983 | Edgren et al. |
| 4,404,228 A | 9/1983 | Cloosterman |
| 4,407,786 A | 10/1983 | Drake et al. |
| 4,452,239 A | 6/1984 | Malem |
| 4,484,577 A | 11/1984 | Sackner et al. |
| 4,524,769 A | 6/1985 | Wetterlin et al. |
| 4,534,343 A | 8/1985 | Nowacki et al. |
| 4,571,334 A | 2/1986 | Yoshida et al. |
| 4,588,744 A | 5/1986 | McHugh |
| 4,590,206 A | 5/1986 | Forrester et al. |
| 4,591,552 A | 5/1986 | Neurath |
| 4,613,500 A | 9/1986 | Suzuki et al. |
| 4,617,272 A | 10/1986 | Kirkwood et al. |
| 4,620,847 A | 11/1986 | Shishov et al. |
| 4,659,696 A | 4/1987 | Hirai et al. |
| 4,680,027 A | 7/1987 | Parsons et al. |
| 4,684,719 A | 8/1987 | Nishikawa et al. |
| 4,701,417 A | 10/1987 | Portenhauser et al. |
| 4,713,249 A | 12/1987 | Schröder |

(Continued)

FOREIGN PATENT DOCUMENTS

AU    757337    2/2003

(Continued)

OTHER PUBLICATIONS

"Albuterol" PubMed Health website accessed on Jan. 29, 2011 at www.ncbi.nlm.nih.gov/pubmedhealth/PMH0000355.*
U.S. Appl. No. 60/060,337, filed Sep. 1997, Kabalnov.
Block, et al., "Solubility and dissolution of triamcinolone acetonide", J. Pharm. Sci., 1973, 62(4), p. 617-621.
Bustami, et al., "Generation of Micro-Particles of Proteins for Aerosol Delivery Using High Pressure Modified Carbon Dioxide", Pharm. Res., 2000, pp. 1360-1366, vol. 17, No. 11.
Christensen, et al., "Preparation of Redispersible Dry Emulsions by Spray Drying", Int. J. Of Pharm., 2001, pp. 187-194.
Cicogna et al., "Efficacy of prophylactic aerosol amphotericin B lipid complex in a rat model of pulmonary aspergillosis", Antimicrobial Agents and Chemotherapy, 1997, 41 (2), p. 259-261.
Dahl, et al., "Selective induction of transforming growth factor beta in human monocytes by lipoarabinomannan of *Mycobacterium tuberculosis*", Infection and Immunity, 64:399-405, 1996.

(Continued)

*Primary Examiner* — James H. Alstrum-Acevedo
(74) *Attorney, Agent, or Firm* — Janah & Associates, P.C.

(57) ABSTRACT

A respiratory dispersion for pulmonary delivery comprises one or more bioactive agents, a suspension medium, and a plurality of perforated microstructures having a mean aerodynamic diameter of less than 5 μm. The suspension medium comprises at least one propellant and permeates the perforated microstructures.

19 Claims, 4 Drawing Sheets

U.S. PATENT DOCUMENTS

| | | |
|---|---|---|
| 4,721,709 A | 1/1988 | Seth et al. |
| 4,739,754 A | 4/1988 | Shaner |
| 4,758,583 A | 7/1988 | Cerami et al. |
| 4,761,400 A | 8/1988 | Doat et al. |
| 4,762,857 A | 8/1988 | Bollin, Jr. et al. |
| 4,765,987 A | 8/1988 | Bonte et al. |
| 4,790,824 A | 12/1988 | Morrow et al. |
| 4,793,997 A | 12/1988 | Drake et al. |
| 4,812,444 A | 3/1989 | Mitsuhashi et al. |
| 4,814,436 A | 3/1989 | Shibata et al. |
| 4,818,542 A | 4/1989 | DeLuca et al. |
| 4,819,629 A | 4/1989 | Jonson |
| 4,824,938 A | 4/1989 | Koyama et al. |
| 4,830,858 A | 5/1989 | Payne et al. |
| 4,847,079 A | 7/1989 | Kwan |
| 4,851,211 A | 7/1989 | Adjei et al. |
| 4,855,326 A | 8/1989 | Fuisz |
| 4,861,627 A | 8/1989 | Mathiowitz et al. |
| 4,865,871 A | 9/1989 | Livesey et al. |
| 4,866,051 A | 9/1989 | Hunt |
| 4,883,762 A | 11/1989 | Hoskins |
| 4,891,319 A | 1/1990 | Roser |
| 4,904,479 A | 2/1990 | Illum |
| 4,906,463 A | 3/1990 | Cleary et al. |
| 4,907,583 A | 3/1990 | Wetterlin et al. |
| 4,942,544 A | 7/1990 | McIntosh et al. |
| 4,950,477 A | 8/1990 | Schmitt et al. |
| 4,952,402 A | 8/1990 | Sparks et al. |
| 4,971,787 A | 11/1990 | Cherukuri et al. |
| 4,984,158 A | 1/1991 | Hillsman |
| 4,988,683 A | 1/1991 | Corbiere |
| 4,995,385 A | 2/1991 | Valentini et al. |
| 4,999,384 A | 3/1991 | Roberts et al. |
| 5,000,591 A | 3/1991 | Burgess |
| 5,006,343 A | 4/1991 | Benson et al. |
| 5,011,678 A | 4/1991 | Wang et al. |
| 5,013,557 A | 5/1991 | Tai |
| 5,017,372 A | 5/1991 | Hastings |
| 5,026,566 A | 6/1991 | Roser |
| 5,026,772 A | 6/1991 | Kobayashi et al. |
| 5,032,585 A | 7/1991 | Lichtenberger |
| 5,033,463 A | 7/1991 | Cocozza |
| 5,043,158 A | 8/1991 | Sleytr et al. |
| 5,043,165 A | 8/1991 | Radhakrishnan |
| 5,049,388 A | 9/1991 | Knight et al. |
| 5,049,389 A | 9/1991 | Radhakrishnan |
| 5,069,936 A | 12/1991 | Yen |
| 5,089,181 A | 2/1992 | Hauser |
| 5,098,893 A | 3/1992 | Franks et al. |
| 5,112,596 A | 5/1992 | Malfroy-Camine |
| 5,112,598 A | 5/1992 | Biesalski |
| 5,118,494 A | 6/1992 | Schultz et al. |
| 5,126,123 A | 6/1992 | Johnson |
| 5,145,684 A | 9/1992 | Liversidge et al. |
| 5,149,543 A | 9/1992 | Cohen et al. |
| 5,149,653 A | 9/1992 | Roser |
| 5,160,745 A | 11/1992 | De Luca et al. |
| 5,173,298 A | 12/1992 | Meadows |
| 5,182,097 A | 1/1993 | Byron et al. |
| 5,190,029 A | 3/1993 | Byron et al. |
| 5,200,399 A | 4/1993 | Wettlaufer et al. |
| 5,202,159 A | 4/1993 | Chen et al. |
| 5,202,333 A | 4/1993 | Berger et al. |
| 5,204,108 A | 4/1993 | Illum |
| 5,208,226 A | 5/1993 | Palmer |
| 5,215,079 A | 6/1993 | Fine et al. |
| 5,225,183 A | 7/1993 | Purewal et al. |
| 5,230,884 A | 7/1993 | Evans et al. |
| 5,239,993 A | 8/1993 | Evans |
| 5,240,712 A | 8/1993 | Smith et al. |
| 5,240,843 A | 8/1993 | Gibson et al. |
| 5,240,846 A | 8/1993 | Collins et al. |
| 5,254,330 A | 10/1993 | Ganderton et al. |
| 5,260,306 A | 11/1993 | Boardman et al. |
| 5,262,405 A | 11/1993 | Girod-Vaquez et al. |
| 5,270,048 A | 12/1993 | Drake |
| 5,284,133 A | 2/1994 | Burns et al. |
| 5,284,656 A | 2/1994 | Platz et al. |
| 5,290,765 A | 3/1994 | Wettlaufer et al. |
| 5,299,566 A | 4/1994 | Davis et al. |
| 5,304,125 A | 4/1994 | Leith |
| 5,306,483 A | 4/1994 | Mautone |
| 5,306,506 A | 4/1994 | Zema et al. |
| 5,308,620 A | 5/1994 | Yen |
| 5,309,900 A | 5/1994 | Knoch et al. |
| 5,312,335 A | 5/1994 | McKinnon et al. |
| 5,312,909 A | 5/1994 | Driessen et al. |
| 5,342,625 A | 8/1994 | Hauer et al. |
| 5,348,730 A | 9/1994 | Greenleaf et al. |
| 5,348,852 A | 9/1994 | Bonderman |
| 5,354,562 A | 10/1994 | Platz et al. |
| 5,354,934 A | 10/1994 | Pitt et al. |
| 5,366,734 A | 11/1994 | Hutchinson |
| 5,376,359 A | 12/1994 | Johnson |
| 5,380,473 A | 1/1995 | Bogue et al. |
| 5,380,519 A | 1/1995 | Schneider et al. |
| 5,384,345 A | 1/1995 | Naton |
| 5,387,431 A | 2/1995 | Fuisz |
| 5,403,861 A | 4/1995 | Goldwin et al. |
| 5,404,871 A | 4/1995 | Goodman et al. |
| 5,422,360 A | 6/1995 | Miyajima et al. |
| 5,422,384 A | 6/1995 | Samuels et al. |
| 5,425,951 A | 6/1995 | Goodrich, Jr. et al. |
| 5,437,272 A | 8/1995 | Fuhrman |
| 5,437,274 A | 8/1995 | Khoobehi et al. |
| 5,451,569 A | 9/1995 | Wong et al. |
| 5,453,514 A | 9/1995 | Niigata et al. |
| 5,458,135 A | 10/1995 | Patton et al. |
| 5,470,885 A | 11/1995 | Fuhrman et al. |
| 5,474,059 A | 12/1995 | Cooper |
| 5,474,759 A | 12/1995 | Fassberg et al. |
| 5,482,927 A | 1/1996 | Maniar et al. |
| 5,490,498 A | 2/1996 | Faithfull et al. |
| 5,492,688 A | 2/1996 | Byron et al. |
| 5,506,203 A | 4/1996 | Backstrom et al. |
| 5,508,269 A | 4/1996 | Smith et al. |
| 5,512,547 A | 4/1996 | Johnson et al. |
| 5,518,709 A | 5/1996 | Sutton et al. |
| 5,518,731 A | 5/1996 | Meadows |
| 5,518,998 A | 5/1996 | Backstrom et al. |
| 5,527,521 A | 6/1996 | Unger |
| 5,540,225 A | 7/1996 | Schutt |
| 5,542,935 A | 8/1996 | Unger et al. |
| 5,547,656 A | 8/1996 | Unger |
| 5,547,696 A | 8/1996 | Sorenson |
| 5,552,160 A | 9/1996 | Liversidge et al. |
| 5,562,608 A | 10/1996 | Sekins et al. |
| 5,567,439 A | 10/1996 | Mters et al. |
| 5,569,448 A | 10/1996 | Wong et al. |
| 5,569,450 A | 10/1996 | Duan et al. |
| 5,571,499 A | 11/1996 | Hafler et al. |
| 5,577,497 A | 11/1996 | Mecikalski et al. |
| 5,580,575 A | 12/1996 | Unger et al. |
| 5,580,859 A | 12/1996 | Felgner et al. |
| 5,589,167 A | 12/1996 | Cleland et al. |
| 5,591,453 A | 1/1997 | Ducheyne et al. |
| 5,605,673 A | 2/1997 | Schutt et al. |
| 5,605,674 A | 2/1997 | Purewal et al. |
| 5,607,915 A | 3/1997 | Patton et al. |
| 5,611,344 A | 3/1997 | Bernstein et al. |
| 5,612,053 A | 3/1997 | Baichwal et al. |
| 5,616,311 A | 4/1997 | Yen |
| 5,618,786 A | 4/1997 | Roosdorp et al. |
| 5,621,094 A | 4/1997 | Roser et al. |
| 5,631,225 A | 5/1997 | Sorensen |
| 5,635,159 A | 6/1997 | Fu Lu et al. |
| 5,635,161 A | 6/1997 | Adjei et al. |
| 5,642,728 A | 7/1997 | Andersson et al. |
| 5,648,095 A | 7/1997 | Illum et al. |
| 5,653,961 A | 8/1997 | McNally et al. |
| 5,653,962 A | 8/1997 | Akehurst et al. |
| 5,654,007 A | 8/1997 | Johnson et al. |
| 5,654,278 A | 8/1997 | Sorenson |
| 5,655,521 A | 8/1997 | Faithfull et al. |
| 5,656,297 A | 8/1997 | Bernstein et al. |
| 5,658,549 A | 8/1997 | Akehurst et al. |
| 5,659,297 A | 8/1997 | Tatavoosian |

| | | |
|---|---|---|
| 5,667,808 A | 9/1997 | Johnson et al. |
| 5,667,809 A | 9/1997 | Trevino et al. |
| 5,673,686 A | 10/1997 | Villax et al. |
| 5,674,471 A | 10/1997 | Akehurst et al. |
| 5,674,472 A | 10/1997 | Akehurst et al. |
| 5,674,473 A | 10/1997 | Purewal et al. |
| 5,676,929 A | 10/1997 | Akehurst et al. |
| 5,676,931 A | 10/1997 | Adjei et al. |
| 5,681,545 A | 10/1997 | Purewal et al. |
| 5,681,746 A | 10/1997 | Bodner et al. |
| 5,683,676 A | 11/1997 | Akehurst et al. |
| 5,683,677 A | 11/1997 | Purewal et al. |
| 5,688,782 A | 11/1997 | Neale et al. |
| 5,690,954 A | 11/1997 | Illum |
| 5,695,743 A | 12/1997 | Purewal et al. |
| 5,695,744 A | 12/1997 | Neale et al. |
| 5,698,537 A | 12/1997 | Pruss |
| 5,705,482 A | 1/1998 | Christensen et al. |
| 5,707,352 A | 1/1998 | Sekins et al. |
| 5,707,644 A | 1/1998 | Illum |
| 5,714,141 A | 2/1998 | Ho et al. |
| 5,718,222 A | 2/1998 | Lloyd et al. |
| 5,718,921 A | 2/1998 | Mathiowitz et al. |
| 5,720,940 A | 2/1998 | Purewal et al. |
| 5,724,957 A | 3/1998 | Rubsamen et al. |
| 5,725,841 A | 3/1998 | Duan et al. |
| 5,725,871 A | 3/1998 | Illum |
| 5,727,546 A | 3/1998 | Clarke et al. |
| 5,728,574 A | 3/1998 | Legg |
| 5,733,555 A | 3/1998 | Chu |
| 5,735,263 A | 4/1998 | Rubsamen et al. |
| 5,736,124 A | 4/1998 | Akehurst et al. |
| 5,740,064 A | 4/1998 | Witte et al. |
| 5,740,794 A | 4/1998 | Smith et al. |
| 5,741,478 A | 4/1998 | Osborne et al. |
| 5,741,522 A | 4/1998 | Violante et al. |
| 5,743,250 A | 4/1998 | Gonda et al. |
| 5,743,252 A | 4/1998 | Rubsamen et al. |
| 5,744,123 A | 4/1998 | Akehurst et al. |
| 5,744,166 A | 4/1998 | Illum |
| 5,747,001 A | 5/1998 | Wiedmann et al. |
| 5,747,445 A | 5/1998 | Backstrom et al. |
| 5,755,218 A | 5/1998 | Johansson et al. |
| 5,756,104 A | 5/1998 | de Haan et al. |
| 5,759,572 A | 6/1998 | Sugimoto et al. |
| 5,766,520 A | 6/1998 | Bronshtein |
| 5,766,573 A | 6/1998 | Purewal et al. |
| 5,770,187 A | 6/1998 | Hasebe et al. |
| 5,770,222 A | 6/1998 | Unger et al. |
| 5,770,234 A | 6/1998 | Gristina et al. |
| 5,770,559 A | 6/1998 | Manning et al. |
| 5,770,585 A | 6/1998 | Kaufman et al. |
| 5,775,320 A | 7/1998 | Patton et al. |
| 5,776,496 A | 7/1998 | Violante et al. |
| 5,780,014 A | 7/1998 | Eljamal et al. |
| 5,780,295 A | 7/1998 | Livesey et al. |
| 5,785,049 A | 7/1998 | Smith et al. |
| 5,804,212 A | 9/1998 | Illum |
| 5,807,552 A | 9/1998 | Stanton et al. |
| 5,811,406 A | 9/1998 | Szoka, Jr. et al. |
| 5,814,607 A | 9/1998 | Patton |
| 5,817,293 A | 10/1998 | Akehurst et al. |
| 5,820,883 A | 10/1998 | Tice et al. |
| 5,829,435 A | 11/1998 | Rubsamen et al. |
| 5,830,430 A | 11/1998 | Unger et al. |
| 5,830,853 A | 11/1998 | Backstrom et al. |
| 5,849,700 A | 12/1998 | Sorenson et al. |
| 5,851,453 A | 12/1998 | Hanna et al. |
| 5,853,698 A | 12/1998 | Straub et al. |
| 5,853,740 A | 12/1998 | Lu et al. |
| 5,853,752 A | 12/1998 | Unger et al. |
| 5,853,763 A | 12/1998 | Tice et al. |
| 5,855,913 A | 1/1999 | Hanes et al. |
| 5,856,367 A | 1/1999 | Barrows et al. |
| 5,858,784 A | 1/1999 | Debs et al. |
| 5,861,175 A | 1/1999 | Walters et al. |
| 5,863,554 A | 1/1999 | Illum |
| 5,873,360 A | 2/1999 | Davies et al. |
| 5,874,063 A | 2/1999 | Briggner et al. |
| 5,874,064 A | 2/1999 | Edwards et al. |
| 5,875,776 A | 3/1999 | Vaghefi |
| 5,891,844 A | 4/1999 | Hafner |
| 5,891,873 A | 4/1999 | Colaco et al. |
| 5,898,028 A | 4/1999 | Jensen et al. |
| 5,921,447 A | 7/1999 | Barger et al. |
| 5,925,334 A | 7/1999 | Rubin et al. |
| 5,928,469 A | 7/1999 | Franks et al. |
| 5,928,647 A | 7/1999 | Rock |
| 5,934,273 A | 8/1999 | Andersson et al. |
| 5,948,411 A | 9/1999 | Koyama et al. |
| 5,955,143 A | 9/1999 | Wheatley et al. |
| 5,955,448 A | 9/1999 | Colaco et al. |
| 5,962,424 A | 10/1999 | Hallahan et al. |
| 5,972,366 A | 10/1999 | Haynes et al. |
| 5,972,388 A | 10/1999 | Sakon et al. |
| 5,976,436 A | 11/1999 | Livesley et al. |
| 5,976,574 A | 11/1999 | Gordon |
| 5,977,081 A | 11/1999 | Marciani |
| 5,985,309 A | 11/1999 | Edwards et al. |
| 5,993,783 A | 11/1999 | Eljamal et al. |
| 5,993,805 A | 11/1999 | Sutton et al. |
| 5,994,314 A | 11/1999 | Eljamal et al. |
| 5,994,318 A | 11/1999 | Gould-Fogerite et al. |
| 5,997,848 A | 12/1999 | Patton |
| 6,001,336 A | 12/1999 | Gordon |
| 6,013,638 A | 1/2000 | Crystal et al. |
| 6,017,310 A | 1/2000 | Johnson et al. |
| 6,019,968 A | 2/2000 | Platz et al. |
| 6,032,666 A | 3/2000 | Davies et al. |
| 6,034,080 A | 3/2000 | Colaco et al. |
| 6,041,777 A | 3/2000 | Faithfull et al. |
| 6,048,546 A | 4/2000 | Sasaki et al. |
| 6,051,256 A | 4/2000 | Platz et al. |
| 6,051,259 A | 4/2000 | Johnson et al. |
| 6,051,566 A | 4/2000 | Bianco |
| 6,060,069 A | 5/2000 | Hill et al. |
| 6,068,600 A | 5/2000 | Johnson et al. |
| 6,071,428 A | 6/2000 | Franks et al. |
| 6,071,497 A | 6/2000 | Steiner et al. |
| 6,077,543 A | 6/2000 | Gordon et al. |
| 6,086,376 A | 7/2000 | Moussa et al. |
| 6,113,948 A | 9/2000 | Heath et al. |
| 6,116,237 A | 9/2000 | Schultz et al. |
| 6,117,455 A | 9/2000 | Takada et al. |
| 6,120,751 A | 9/2000 | Unger |
| 6,123,924 A | 9/2000 | Mistry et al. |
| 6,123,936 A | 9/2000 | Platz et al. |
| 6,129,934 A | 10/2000 | Egan et al. |
| 6,136,295 A | 10/2000 | Edwards et al. |
| 6,136,346 A | 10/2000 | Eljamal et al. |
| 6,138,668 A | 10/2000 | Patton et al. |
| 6,139,819 A | 10/2000 | Unger et al. |
| 6,142,216 A | 11/2000 | Lannes |
| 6,143,276 A | 11/2000 | Unger |
| 6,165,463 A | 12/2000 | Platz et al. |
| 6,165,508 A | 12/2000 | Tracy et al. |
| 6,165,597 A | 12/2000 | Williams et al. |
| RE37,053 E | 2/2001 | Hanes et al. |
| 6,187,344 B1 | 2/2001 | Eljamal et al. |
| 6,190,859 B1 | 2/2001 | Putnak et al. |
| 6,207,135 B1 | 3/2001 | Rossling et al. |
| 6,230,707 B1 | 5/2001 | Horlin |
| 6,231,851 B1 | 5/2001 | Platz et al. |
| 6,248,720 B1 | 6/2001 | Mathiowitz et al. |
| 6,254,854 B1 | 7/2001 | Edwards et al. |
| 6,258,341 B1 | 7/2001 | Foster et al. |
| 6,284,282 B1 | 9/2001 | Maa et al. |
| 6,290,991 B1 | 9/2001 | Roser et al. |
| 6,303,581 B2 | 10/2001 | Pearlman |
| 6,303,582 B1 | 10/2001 | Eljamal et al. |
| 6,309,623 B1 * | 10/2001 | Weers et al. .................... 424/45 |
| 6,309,671 B1 | 10/2001 | Foster et al. |
| 6,313,102 B1 | 11/2001 | Colaco et al. |
| 6,315,983 B1 | 11/2001 | Eistetter |
| 6,331,310 B1 | 12/2001 | Roser et al. |
| 6,334,182 B2 | 12/2001 | Merchant et al. |
| 6,358,530 B1 | 3/2002 | Eljamal et al. |
| 6,365,190 B1 | 4/2002 | Gordon et al. |

| | | |
|---|---|---|
| 6,372,258 B1 | 4/2002 | Platz et al. |
| 6,387,886 B1 | 5/2002 | Montgomery et al. |
| 6,416,739 B1 | 7/2002 | Rogerson et al. |
| 6,423,334 B1 | 7/2002 | Brayden et al. |
| 6,423,344 B1 | 7/2002 | Platz et al. |
| 6,426,210 B1 | 7/2002 | Franks et al. |
| 6,433,040 B1 | 8/2002 | Dellamary et al. |
| 6,468,782 B1 | 10/2002 | Tunnacliffe et al. |
| 6,475,468 B2 | 11/2002 | Zhu et al. |
| 6,479,049 B1 | 11/2002 | Platz et al. |
| 6,503,411 B1 | 1/2003 | Franks et al. |
| 6,503,480 B1 | 1/2003 | Edwards et al. |
| 6,509,006 B1 | 1/2003 | Platz et al. |
| 6,514,482 B1 | 2/2003 | Bartus et al. |
| 6,514,496 B1 | 2/2003 | Platz et al. |
| 6,518,239 B1 | 2/2003 | Kuo et al. |
| 6,551,578 B2 | 4/2003 | Adjei et al. |
| 6,565,871 B2 | 5/2003 | Roser et al. |
| 6,565,885 B1 | 5/2003 | Tarara et al. |
| 6,569,406 B2 | 5/2003 | Stevenson et al. |
| 6,569,458 B1 | 5/2003 | Gombotz et al. |
| 6,572,893 B2 | 6/2003 | Gordon et al. |
| 6,582,728 B1 | 6/2003 | Platz et al. |
| 6,586,006 B2 | 7/2003 | Roser et al. |
| 6,589,560 B2 | 7/2003 | Foster et al. |
| 6,592,904 B2 | 7/2003 | Platz et al. |
| 6,630,169 B1 | 10/2003 | Bot et al. |
| 6,638,495 B2 * | 10/2003 | Weers et al. .......... 424/45 |
| 6,649,911 B2 | 11/2003 | Kawato |
| 6,652,837 B1 | 11/2003 | Edwards et al. |
| 6,655,379 B2 | 12/2003 | Clark et al. |
| 6,673,335 B1 | 1/2004 | Platz et al. |
| 6,681,767 B1 | 1/2004 | Patton et al. |
| 6,685,967 B1 | 2/2004 | Patton et al. |
| 6,737,045 B2 | 5/2004 | Patton et al. |
| 6,737,066 B1 | 5/2004 | Moss |
| 6,752,893 B2 | 6/2004 | Frieder et al. |
| 6,797,258 B2 | 9/2004 | Platz et al. |
| 6,811,792 B2 | 11/2004 | Roser et al. |
| 6,825,031 B2 | 11/2004 | Franks et al. |
| 6,893,657 B2 | 5/2005 | Roser et al. |
| 6,921,527 B2 | 7/2005 | Platz et al. |
| 6,946,117 B1 | 9/2005 | Schutt et al. |
| 7,306,787 B2 | 12/2007 | Tarara et al. |
| 7,393,544 B2 | 7/2008 | Dellamary et al. |
| 7,442,388 B2 | 10/2008 | Weers et al. |
| 7,628,978 B2 * | 12/2009 | Weers et al. .......... 424/46 |
| 7,790,145 B2 * | 9/2010 | Weers et al. .......... 424/46 |
| 2001/0035184 A1 | 11/2001 | Schuler et al. |
| 2002/0017295 A1 | 2/2002 | Weers et al. |
| 2002/0052310 A1 | 5/2002 | Edwards et al. |
| 2002/0127188 A1 | 9/2002 | Platz et al. |
| 2002/0132787 A1 | 9/2002 | Eljamal et al. |
| 2002/0187106 A1 | 12/2002 | Weers et al. |
| 2002/0192164 A1 | 12/2002 | Patton et al. |
| 2003/0035778 A1 | 2/2003 | Platz et al. |
| 2003/0068277 A1 | 4/2003 | Vanbever et al. |
| 2003/0068279 A1 | 4/2003 | Platz et al. |
| 2003/0072718 A1 | 4/2003 | Platz et al. |
| 2003/0086877 A1 | 5/2003 | Platz et al. |
| 2003/0092666 A1 | 5/2003 | Eljamal et al. |
| 2003/0096774 A1 | 5/2003 | Gonda et al. |
| 2003/0113273 A1 | 6/2003 | Patton et al. |
| 2003/0113900 A1 | 6/2003 | Tunnacliffe et al. |
| 2003/0171282 A1 | 9/2003 | Patton |
| 2003/0185765 A1 | 10/2003 | Platz et al. |
| 2003/0198601 A1 | 10/2003 | Platz et al. |
| 2003/0203036 A1 | 10/2003 | Gordon et al. |
| 2003/0215512 A1 | 11/2003 | Foster et al. |
| 2003/0215514 A1 | 11/2003 | Platz et al. |
| 2003/0219490 A1 | 11/2003 | Hovey et al. |
| 2004/0052825 A1 | 3/2004 | Roser et al. |
| 2004/0096400 A1 | 5/2004 | Patton et al. |
| 2004/0096401 A1 | 5/2004 | Patton et al. |
| 2004/0105820 A1 | 6/2004 | Weers et al. |
| 2004/0156792 A1 * | 8/2004 | Tarara et al. .......... 424/46 |
| 2004/0170568 A1 | 9/2004 | Weers et al. |
| 2004/0219206 A1 | 11/2004 | Roser et al. |
| 2005/0074449 A1 | 4/2005 | Bot et al. |
| 2005/0147566 A1 | 7/2005 | Fleming et al. |
| 2005/0186143 A1 | 8/2005 | Stevenson et al. |
| 2005/0203002 A1 | 9/2005 | Tzannis et al. |
| 2005/0214224 A1 | 9/2005 | Weers et al. |
| 2006/0159625 A1 | 7/2006 | Tarara et al. |
| 2006/0159629 A1 | 7/2006 | Tarara et al. |
| 2006/0165606 A1 | 7/2006 | Tarara et al. |
| 2008/0233194 A1 * | 9/2008 | Dellamary et al. .......... 424/484 |

FOREIGN PATENT DOCUMENTS

| | | |
|---|---|---|
| AU | 731671 | 4/2004 |
| BE | 0902257 | 8/1985 |
| DE | 3141498 | 4/1983 |
| DE | 3713326 | 10/1987 |
| EP | 0015123 | 3/1980 |
| EP | 0072046 | 2/1983 |
| EP | 0090356 | 10/1983 |
| EP | 0111216 | 6/1984 |
| EP | 0136030 | 4/1985 |
| EP | 0139286 | 5/1985 |
| EP | 0140489 | 5/1985 |
| EP | 0222313 | 5/1987 |
| EP | 0229810 | 7/1987 |
| EP | 0274431 | 7/1988 |
| EP | 0282179 | 9/1988 |
| EP | 0325936 | 8/1989 |
| EP | 0356154 | 2/1990 |
| EP | 0360340 | 3/1990 |
| EP | 0366303 | 5/1990 |
| EP | 0383569 | 8/1990 |
| EP | 0415567 | 3/1991 |
| EP | 0174759 | 4/1991 |
| EP | 0430045 | 6/1991 |
| EP | 0433679 | 6/1991 |
| EP | 0463653 | 1/1992 |
| EP | 0474874 | 3/1992 |
| EP | 0520748 | 10/1992 |
| EP | 0600730 | 8/1994 |
| EP | 0616524 | 9/1994 |
| EP | 0640347 | 3/1995 |
| EP | 0653205 | 5/1995 |
| EP | 0656203 | 6/1995 |
| EP | 0658101 | 6/1995 |
| EP | 0663840 | 7/1995 |
| EP | 0714905 | 6/1996 |
| EP | 0743860 | 11/1996 |
| EP | 0536235 | 1/1997 |
| EP | 0773781 | 5/1997 |
| EP | 0257956 | 3/1998 |
| EP | 0904056 | 3/1999 |
| EP | 1019022 | 4/2003 |
| ES | 8403520 | 6/1984 |
| FR | 2238476 | 2/1975 |
| GB | 1263780 | 2/1972 |
| GB | 1265615 | 3/1972 |
| GB | 1288094 | 9/1972 |
| GB | 1381588 | 1/1975 |
| GB | 1477775 | 6/1977 |
| GB | 1533012 | 11/1978 |
| GB | 2025196 | 1/1980 |
| GB | 2105189 | 3/1983 |
| GB | 2126588 | 9/1984 |
| GB | 21878191 | 1/1987 |
| JP | 52139789 | 11/1977 |
| JP | 58216695 | 12/1983 |
| JP | 59095885 | 6/1984 |
| JP | 60244288 | 12/1985 |
| JP | 62228272 | 10/1987 |
| JP | 62255434 | 11/1987 |
| JP | 02084401 | 3/1990 |
| JP | 03038592 | 2/1991 |
| JP | 03264537 | 11/1991 |
| JP | 06100464 | 4/1994 |
| WO | WO8604095 | 7/1986 |
| WO | WO8700196 | 1/1987 |
| WO | WO8702038 | 4/1987 |
| WO | WO8705300 | 9/1987 |
| WO | WO8801862 | 3/1988 |
| WO | WO8808298 | 11/1988 |

| | | |
|---|---|---|
| WO | WO8906976 | 8/1989 |
| WO | WO8908449 | 9/1989 |
| WO | WO9005182 | 5/1990 |
| WO | WO9011756 | 10/1990 |
| WO | WO9013285 | 11/1990 |
| WO | WO9015635 | 12/1990 |
| WO | WO9104715 | 4/1991 |
| WO | WO9116038 | 10/1991 |
| WO | WO9116882 | 11/1991 |
| WO | WO9118091 | 11/1991 |
| WO | WO9202133 | 2/1992 |
| WO | WO9219243 | 11/1992 |
| WO | WO9300951 | 1/1993 |
| WO | WO9309832 | 5/1993 |
| WO | WO9310758 | 6/1993 |
| WO | WO9311743 | 6/1993 |
| WO | WO9312240 | 6/1993 |
| WO | WO9313752 | 7/1993 |
| WO | WO9314172 | 7/1993 |
| WO | WO9317663 | 9/1993 |
| WO | WO9323065 | 11/1993 |
| WO | WO9323110 | 11/1993 |
| WO | WO9404133 | 3/1994 |
| WO | WO9407514 | 4/1994 |
| WO | WO9408552 | 4/1994 |
| WO | WO9413271 | 6/1994 |
| WO | WO9500127 | 1/1995 |
| WO | WO9500128 | 1/1995 |
| WO | WO9501324 | 1/1995 |
| WO | WO9520979 | 8/1995 |
| WO | WO9524183 | 9/1995 |
| WO | WO9531182 | 11/1995 |
| WO | WO9531479 | 11/1995 |
| WO | WO9603116 | 2/1996 |
| WO | WO9603978 | 2/1996 |
| WO | WO9609085 | 3/1996 |
| WO | WO9607399 | 4/1996 |
| WO | WO9609814 | 4/1996 |
| WO | WO9615814 | 5/1996 |
| WO | WO9618388 | 6/1996 |
| WO | WO9619968 | 7/1996 |
| WO | WO9626746 | 9/1996 |
| WO | WO9627393 | 9/1996 |
| WO | WO9632096 | 10/1996 |
| WO | WO9632116 | 10/1996 |
| WO | WO9636314 | 11/1996 |
| WO | WO9640049 | 12/1996 |
| WO | WO9640066 | 12/1996 |
| WO | WO9640077 | 12/1996 |
| WO | WO9640285 | 12/1996 |
| WO | WO9713503 | 4/1997 |
| WO | WO9725086 | 7/1997 |
| WO | WO9726863 | 7/1997 |
| WO | WO9732609 | 9/1997 |
| WO | WO9734689 | 9/1997 |
| WO | WO9736574 | 10/1997 |
| WO | WO9740819 | 11/1997 |
| WO | WO9807414 | 2/1998 |
| WO | WO9808519 | 3/1998 |
| WO | WO9824882 | 6/1998 |
| WO | WO9829096 | 7/1998 |
| WO | WO9833487 | 9/1998 |
| WO | WO9851282 | 11/1998 |
| WO | WO9858989 | 12/1998 |
| WO | WO9906026 | 2/1999 |
| WO | WO9909956 | 3/1999 |
| WO | WO9916419 | 4/1999 |
| WO | WO9916420 | 4/1999 |
| WO | WO9916421 | 4/1999 |
| WO | WO9916422 | 4/1999 |
| WO | WO9932083 | 7/1999 |
| WO | WO9932098 | 7/1999 |
| WO | WO9938493 | 8/1999 |
| WO | WO9944583 | 9/1999 |
| WO | WO9945986 | 9/1999 |
| WO | WO9945987 | 9/1999 |
| WO | WO9947196 | 9/1999 |
| WO | WO9966903 | 12/1999 |
| WO | WO0000176 | 1/2000 |
| WO | WO0000215 | 1/2000 |
| WO | WO0010541 | 3/2000 |
| WO | WO0021594 | 4/2000 |
| WO | WO0056282 | 9/2000 |
| WO | WO0061157 | 10/2000 |
| WO | WO0072904 | 12/2000 |
| WO | WO0100263 | 1/2001 |
| WO | WO0113891 | 3/2001 |
| WO | WO0113892 | 3/2001 |
| WO | WO0126683 | 4/2001 |
| WO | WO0132144 | 5/2001 |
| WO | WO0164254 | 9/2001 |
| WO | WO0185136 | 11/2001 |
| WO | WO0185137 | 11/2001 |
| WO | WO0195874 | 12/2001 |
| WO | WO2006002140 | 1/2006 |

OTHER PUBLICATIONS

Office Action in U.S. Appl. No. 10/644,265 (patented as 7,628,978) dated Feb. 1, 2007.
Office Action in U.S. Appl. No. 10/644,265 (patented as 7,628,978) dated Feb. 20, 2008.
Office Action in U.S. Appl. No. 10/644,265 (patented as 7,628,978) dated May 9, 2006.
Office Action in U.S. Appl. No. 10/644,265 (patented as 7,628,978) dated Oct. 7, 2005.
Office Action in U.S. Appl. No. 10/616,448 dated Feb. 25, 2010.
Office Action in U.S. Appl. No. 10/616,448 dated Apr. 16, 2008.
Office Action in U.S. Appl. No. 10/616,448 dated May 4, 2006.
Office Action in U.S. Appl. No. 10/616,448 dated Aug. 19, 2005.
Office Action in U.S. Appl. No. 10/616,448 dated Sep. 25, 2009.
Office Action in U.S. Appl. No. 10/616,448 dated Oct. 25, 2004.
Office Action in U.S. Appl. No. 10/616,448 dated Nov. 14, 2008.
Office Action in U.S. Appl. No. 11/187,757 dated Mar. 26, 2010.
Office Action in U.S. Appl. No. 10/096,780 (patented as 7,306,787) dated Jan. 25, 2006.
Office Action in U.S. Appl. No. 10/096,780 (patented as 7,306,787) dated Apr. 19, 2005.
Office Action in U.S. Appl. No. 10/096,780 (patented as 7,306,787) dated May 20, 2003.
Office Action in U.S. Appl. No. 10/096,780 (patented as 7,306,787) dated Jun. 17, 2004.
Office Action in U.S. Appl. No. 10/096,780 (patented as 7,306,787) dated Oct. 2, 2002.
Office Action in U.S. Appl. No. 09/568,818 dated Jan. 24, 2006.
Office Action in U.S. Appl. No. 09/568,818 dated Feb. 26, 2008.
Office Action in U.S. Appl. No. 09/568,818 dated Apr. 7, 2005.
Office Action in U.S. Appl. No. 09/568,818 dated Apr. 10, 2002.
Office Action in U.S. Appl. No. 09/568,818 dated May 5, 2004.
Office Action in U.S. Appl. No. 09/568,818 dated Jun. 4, 2007.
Office Action in U.S. Appl. No. 09/568,818 dated Jul. 29, 2003.
Office Action in U.S. Appl. No. 09/568,818 dated Oct. 6, 2006.
Office Action in U.S. Appl. No. 09/568,818 dated Nov. 5, 2002.
Office Action in U.S. Appl. No. 09/568,818 dated Dec. 8, 2008.
Office Action in U.S. Appl. No. 09/851,226 (patented as 7,442,388) dated Feb. 11, 2003.
Office Action in U.S. Appl. No. 09/851,226 (patented as 7,442,388) dated Mar. 22, 2005.
Office Action in U.S. Appl. No. 09/851,226 (patented as 7,442,388) dated May 5, 2004.
Office Action in U.S. Appl. No. 09/851,226 (patented as 7,442,388) dated Jun. 24, 2002.
Office Action in U.S. Appl. No. 09/851,226 (patented as 7,442,388) dated Jul. 24, 2003.
Office Action in U.S. Appl. No. 10/141,219 dated Jan. 8, 2009.
Office Action in U.S. Appl. No. 10/141,219 dated Mar. 10, 2006.
Office Action in U.S. Appl. No. 10/141,219 dated Mar. 26, 2010.
Office Action in U.S. Appl. No. 10/141,219 dated Jun. 6, 2005.
Office Action in U.S. Appl. No. 10/141,219 dated Jul. 21, 2008.
Office Action in U.S. Appl. No. 10/141,219 dated Aug. 18, 2009.
Office Action in U.S. Appl. No. 10/141,219 dated Oct. 23, 2003.
Office Action in U.S. Appl. No. 10/141,219 dated Nov. 15, 2004.
Office Action in U.S. Appl. No. 10/141,219 dated Nov. 29, 2006.
Office Action in U.S. Appl. No. 12/258,163 dated Sep. 28, 2009.

Office Action in U.S. Appl. No. 10/612,393 dated Feb. 9, 2006.
Office Action in U.S. Appl. No. 10/612,393 dated Aug. 1, 2006.
Office Action in U.S. Appl. No. 11/317,839 dated Apr. 13, 2009.
Office Action in U.S. Appl. No. 11/317,839 dated Sep. 25, 2008.
Office Action in U.S. Appl. No. 11/317,839 dated Dec. 23, 2009.
Office Action in U.S. Appl. No. 09/888,311 dated Jan. 8, 2003.
Office Action in U.S. Appl. No. 09/888,311 dated Jun. 25, 2002.
Office Action in U.S. Appl. No. 09/888,311 dated Dec. 5, 2001.
Office Action in U.S. Appl. No. 09/999,071 (patented as 7,205,343) dated Jan. 18, 2006.
Office Action in U.S. Appl. No. 09/999,071 (patented as 7,205,343) dated Jun. 17, 2003.
Office Action in U.S. Appl. No. 09/999,071 (patented as 7,205,343) dated Oct. 7, 2004.
Office Action in U.S. Appl. No. 11/076,430 dated Mar. 3, 2010.
Office Action in U.S. Appl. No. 11/076,430 dated May 11, 2009.
Office Action in U.S. Appl. No. 11/076,430 dated Nov. 13, 2008.
Office Action in U.S. Appl. No. 10/141,032 dated May 20, 2005.
Office Action in U.S. Appl. No. 10/141,032 dated Jul. 16, 2003.
Office Action in U.S. Appl. No. 10/141,032 dated Aug. 17, 2004.
Office Action in U.S. Appl. No. 10/141,032 dated Oct. 23, 2002.
Haitsma, et al., "Exogenous Surfactant as a Drug Delivery Agent", Adv. Drug Del. Rev., 2001, pp. 197-207.
JM. Goldman et al., "Inhaled Micronised Gentamicin Powder: A New Delivery System," Thorax, BMJ Publishing Group, GB, vol. 45, No. 12, Dec. 1990, pp. 939-940 XP001057935.
Johansen, et al., "Technological Considerations Related to the Up-Scaling of Protein Microencapsulation by Spray-Drying", Eur. J. of Pham. and Biopharm., 2000, pp. 413-417.
Morel, et al., "Crossregulation between Th1 and Th2 cells", Critical Reviews in Immunology U.S., 1998, pp. 275-303, vol. 18, No. 4.
Sasaki, et al, "Human immunodeficiency viris type-1 specific immune responses induced by DNA vaccination are greatly enhances by manna-coated DIC14-amidine", Euro. J. of Immunology, Dec. 1997, pp. 3121-3129, vol. 27, No. 12.
Shibata, et al., "Chitin Particle-Induced Cell-Mediated Phagocytosis Initiaties IL-12 Production", J. of Immunology, 1997, pp. 2462-2467, vol. 159, No. 5.
"Chapter 89—Oral Solid Dosage Forms, "In *Remington's Pharmaceutical Sciences*, 18th Edition, Mack Publishing Co., Gennaro, A.R., pp. 1646-1647 (1990).
"Pfizer and Inhale Therapeutic Systems Enter Pulmonary Insulin Collaboration for Dry Powder Aerosol Delivery", Health News Daily, vol. 7, No. 13, pp. 4-5 (Jan. 1995).
Agrimi, U., et al. "Amyloid, Amyloid-Inducers, Cytokines and Heavy Metals in Scrapie and Other Human and Animal Subacute Spongiform Encephalopathies: Some Hypotheses", *Med. Hypotheses*, 40(2): 113-116 (1993).
Ahlneck et al. "The Molecular Basis of Moisture Effects on the Physical and Chemical Stability of Drugs in the Solid State" Int. J. of Pharmaceutics 62: 87-95 (1990).
Akers, M.J., et al., "Glycine Crystallization During Freezing: The Effects of Salt Form, pH, and Ionic Strenght", *Pharmaceutical Research* 12(10):1457 1461 (1995).
Akoh, et al., "One-stage synthesis of raffinose fatty acid polyesters", J. Food Sci., 52:1570-1576 (1987).
Alberts, B., et al., *Molecular Biology of the Cell*, 2nd ed., Garland Publishing, Inc., Ch.2, p. 58 (1989).
Aldous, et al., "The Crystallization of Hydrates from Amorphous Carbohydrates", *Cryo-Letters*, 16:181-186 (1995).
Allen, D.J., et al. "Determination of the Degree of Crystallinity in Solid-Solid Equilibria", J. Pharm. Sci., 58:1190-1193 (1969).
Allison, S.D. and Anchordoquy, Thomas J., *Lyophilization of Nonviral Gene Delivery Systems*, Methods in Molecular Medicine, Nonviral Vectors for Gene Therapy, Ch. 18, pp. 225-252 (Mark A. Findeis ed., Humana Press, 2001).
Allison, S.D., et al., "Mechanisms of Protection of Cationic Lipid-DNA Complexes During Lyophilization", *Journal of Pharmaceutical Sciences* 89(5): 682-691 (2000).
Altenbach et al. "Ca2+Binding to Phosphatidycholine Bilayers as Studied by Deuterium Magnetic Resonance. Evidence for the Formation of a Ca2+Complex with Two Phospholipid Molecules" Biochemistry 23: 3913-3920 (1984).

Amidon, G.E., et al., "Powder Flow Testing in Preformulation and Formulation Development", *Pharm. Manuf.*, 2: 20-31 (1985).
Anchoroquy, Thomas J., Physical Stabilization of DNA Based Therapeutics, 6(9): DDT 463-470 (May 2001).
Anekwe, J., et al., "Relaxation Constants as a Predictor of Protein Stabilization", *Biocalorimetry: Applications of Calorimetry in the Biological Science*, J.E. Ladbury and B.Z. Chowdhry, editors, John Wiley & Sons, pp. 243-251 (1998).
Babincova et al. "Dextran Enhances Calcium-Induced Aggregation of Phosphatidylserine Liposomes: Possible Implications for Exocytosis" Physiol Res 48(4): 319-321 (1999).
Bandara, G., et al., "Interarticular Expression of Biologically Active Interleukin 1-Receptor-Antagonist Protein by Ex Vivo Gene Transfer", *Proc. Natl. Acad. Sci.*, 90:10764-10768 (Nov. 1993).
Barnett,.A.H., Exhubera Inhaled Insulin: A Review *Int. J. Clin. Pract* 58(4): 394-401 (2004).
Bell, J.H., et al., "Dry Powder Aerosols I: A New Powder Inhalation Device", J. Pharm. Sci., 60(10): 1559-1564 (Oct. 1971).
Belopol'skaya, T.V. et al. "The effect of water as natural plasticizer on thermal properties of denatured DNA studied by calorimetry" Vestnik Sankt-Peterburgskogo Universiteta Journal, Abstract Only, 1999, 2 pages.
Ben-Jebria, Abdellaziz et al., "Large Porous Particles for Sustained Protection from Carbochol Induced Bronchoconstriction in Guinea Pigs," Pharm. Res., vol. 16 (No. 4), p. 555-561 (1999).
Bigsbee, et al. "Solid State Liability of Insulin: Comparison of Crystalline and Amorphous Forms", *Pharmaceutical Research* 10(10): Abstract No. PDD 7418, p. S-279 (1993).
Blakeley, et al., "Dry instant blood typing for bedside use", Lancet, 336: 854-855 (1990).
Bögelein, J., et al., "Influence of Amorphous Mannitol on Powder Properties of Spray Dried Trehalose/Dextran Mixtures", [on-line] [retrieved Sep. 2005] Retrieved from the Internet, 2 pages (2003).
Bootsma, H.P.R., et al., "β-Cyclodestrin as an Excipient in Solid Oral Dosage Forms: In Vitro and In Vivo Evaluation of Spray-Dried Diazepan-β-Cyclodestrin Products", International Journal of Pharmaceutics 51:213-223 (1989).
Borgstrom et al., "Lung Deposition of Budesonide Inhaled via Turbuhaler," Eur. Respir. J, p. 69-73, (Feb. 26, 1994).
Bosquillon, C. et al., "Aerosolization Properties, Surface Composition and Physical State of Spray. Dried Protein Powders", *Journal of Controlled Release*, 99: 357-367 (2004).
Branca, C., et al., "Destructuring effect of trehalose on the tetrahedral network of water: a Raman and neutron diffraction comparison", Physica A 304: 314-318 (2002).
Branchu, S., et al., "Hydroxypropyl-β-Cyclodextrin Inhibits Spray-Drying-Induced Inactivation of β-Galactosidase", *Journal of Pharmaceutical Sciences* 88(9): 905-911 (1999).
Branchu, S., et al., "The Effect of Cyclodestrins on Monomeric Protein Unfolding", *Biocalorimetry: Applications of Calorimetry in the Biological Sciences*, J.E. Ladbury and B.Z. Chowdhry (eds.), John Wiley & Sons, Ltd., 297-301 (1998).
Brange, et al., "Chemical Stability of Insulin, I, Hydrolytic Degradation During Storage of Pharmaceutical Preparations", *Pharmaceutical Research* 9(6): 715-726 (1992).
Breitenbach, J., "Melt Extrusion: From Process to Drug Delivery Technology", *European Journal of Pharmaceuticals and Biopharmaceutics* 54: 107-117 (2002).
Broadhead, et al. "The effect of process and formulation variable on the properties of spray-dried Beta-Galactosidase", Journal of Pharmaceutical Sciences 88(9): 905-911, 1999.
Broadhead, J., et al., *The Spray Drying of Pharmaceuticals*, 18 Drug Development and Industrial Pharmacy, p. 1169-1206 (1992).
Brown, "A Therapeutic Panorama of the Spongiform Encephalopathies", *Antiviral Chem. Chemother.* 1(2): 75-83 (1990).
Buckton et al. "The Use of Gravimetric Studies to Assess the Degree of Crystallinity of Predominantly Crystalline Powders" Int. J. of Pharmaceutics 123: 265-271 (1995).
Buitink, Julia, et al., *High Critical Temperature above Tg May Contribute to the Stability of Biological Systems*, 79 Biophysical Journal, 1119 1128 (Aug. 2000).
Buldt et al. "Neutron Diffraction Studies on Phosphatidylcholine Model Membranes" J. Mol. Biol. 134: 673-691 (1979).

Burvall, et al. "Storage of Lactose-Hydrolised Dried Milk: Effect of Water Activity on the Protein Nutritional Value", Journal of Dairy Research 45:381-389 (1978).

Byron, Peter R., et al., Drug Carrier Selection—Important Physicochemical Characteristics Respiratory Drug Delivery, 5th Ed., Interpharm Press., 103-113 (1996).

Byström et al., "Microcalorimetry—A Novel Technique for Characterization of Powders", *Respiratory Drug Delivery IV*, p. 297-302 (1994).

Carpenter, John F., et al., "Rational Design of Stable Lyophilized Protein Formulations: Some Practical Advice", *Pharmaceutical Res.*, 14(8): 969-975 (1997).

Casselyn, M. et al., *Time-Resolved Scattering Investigations of Brome Mosaic Virus Micro crystals Appearance* D58 ACTH CRYST. 1568-1570 (2002).

Caughey, et al., "Sulphated Polyanion Inhibition of Scrapie-Associated PrP Accumulation in Cultured Cells", *J. Virol.*, 67(2): 643-650 (1993).

Cevc. G. "Membrane Electrostatics" Biochim Biophys Acta 1031(3): 311-382 (1990)., in particular pp. 330-338.

Chan, et al., "Formulation of Vaccine Ajuvant Muramyldipeptides (MDP). 1 Characterization of Amorphous and Crystalline Forms of a Muramyldipeptide Analouge", Pharmaceutical Research, 5(8): 523-527 (1988).

Chan, Hak-Kim, et al., "Physical Stability of Salmon Calcitonin Spray-Dried Powders for Inhalation", *Journal of Pharmaceutical Sciences*, 93(3): 792-804 (2004).

Chan, Hak-Kim, et al., "Solid State Characterization of Spray-Dried Powders of Recombinant Human Deoxyribonuclease (RhDNase)", *Journal of Pharmaceutical Sciences*, 87(5): 647-654 (1998).

Chavan, V., et al., "Effect of Rise in Simulated Inspiratory Flow Rate and Carrier Particle Size on Powder Emptying From Dry Powder Inhalers", *AAPS Pharmsci* 2000; 2(2) article 10 [on-line] Retrieved from the Internet 7 pages (2000).

Chavan, V., et al., "Novel System to Investigate the Effects of Inhaled Volume and Rates of Rise in Simulated Inspiratory Air Flow on Fine Particle Output From a Dry Power Inhaler", *AAPS Pharmisci* 2002; 4(2) article 6, pp. 1-6.

Chavan, V., et al., Effect of Particle Size and Rise in Simulated Inspiratory Flow Rate on Device Emptying in a Dry Powder Inhaler SYstem, [on-line] [retrieved Jan. 7, 2005] Retrieved from the Internet 1 page (1999).

Chawla, et al., "Production of Spray Dried Salbutamol Suplhate for Use in Dry Powder Aerosol Formulation", *International Journal of Pharmaceutics*, 108: 233-240 (1994).

Chiou, et al., "Pharmaceutical Applications of Solid Dispersion Systems", J. Pharm., 60(9): 1281-1302 (1971).

Cleland, et al., "The Development of Stable Protein Formulations: A Close Look at Protein Aggregation, Deamidation and Oxidation", *Critical Reviews in Therapeutic Drug Carrier Systems*, 10(4): 307-377 (1993).

Cline D., "Predicting the Quality of Powders for Inhalation from Surface Energy and Area", *Pharmaceutical Research*, 19(9): 1274-1277 (2002).

Cline, D., et al., "Predicting the Quality of Powders for Inhalation", *Respiratory Drug Delivery VIII*p. 683-685 (2002).

Colaco, et al., "Chapter 14: Chemistry of Protein Stabilization by Trehalose", ACS *Symposium Series* 567, *Formulation and Delivery of Proteins and Peptides*, J.L. Cleland & R. Langer, pp. 222-240 (1994).

Colaco, et al., "Extraordinary Stability of Enzymes Dreid in Trehalose: Simplified Molecular Biology", *Bio/Technology* 10: 1007-1011 (1992).

Colaco, et al., "Trehalose Stabilization of Biological Molecules", *Biotechnol. Internet.*, pp. 345, 347-350 (1992).

Considine, G.D., et al., *Van Nostrand's Scientific Encyclopedia*, 9th edition, vol. 2, Wiley-Interscience, John Wiley & Sons, Inc., Definition of Vaccines: pp. 3591-3592 (2002).

Constantino, et al., "Moisture-Induced Aggregation of Lyophilized Insulin", *Pharmaceutical Research*, 11(1): 21-29 (1994).

Constantino, H.R., et al., "Effect of Mannitol Crystallization on the Stability and Aerosol Performance of a Spray-Dried Pharmaceutical Protein, Recombinant Humanized Anti-IgE Monoclonal Antibody", *Journal of Pharmaceutical Sciences*, 87(11): 1406-1411 (1998).

Craig, I.D., et al., "Mailiard Reaction Kinetics in Model Preservation Systems in the Vicinity of the Glass Transition: Experiment and Theory", *J. Agric. Food Chem.* 49(10: 4706-4712 (2001).

Crommelin, et al., "Liposomes", Chapter 3, *Colloidal Drug Delivery Systems*, J. Kreuter, editor: 73-190 (1994).

Crowe, et al., "Are Freezing and Dehydration Similar Stress Vectors? A Comparison of Modes of Interaction of Stabilizing Solutes with Biomolecules", Cryobiol. 27: 219-231 (1990).

Crowe, et al., "Interations of Sugars with Membranes", Biochimica et Biophysica Acta, 947: 367-384 (1988).

Crowe, John H., et al., "The Role of Vitrification in Anhydrobiosis", *Annu. Rev. Physiol.*, 60: 73-103 (1998).

Crowe, Lois M., et al., "Is Trehalose Special for Preserving Dry Biomaterials?", *Biophysical Journal*, 71: 2087-2093 (1996).

Daemen, et al., "The Destruction of Enzymes and Bacteria During the Spray-Drying of Milk and Whey, 2. The Effect of the Drying Conditions", Neth. Milk Dairy J., 36: 211-229 (1982).

Dalby, et al., "Relationship Between Particles Morphology and Drug Release Properties After Hydration of Aerosols Properties Containing Liposome Forming Ingredients", *Pharmaceutical Research*, 5(10): S-94, Abstract PD 888 (1988).

Dalby, R.N., et al., "Droplets Drying and Electrostatic Collection a Novel Alternative to Conventional Comminution Techniques", *Journal of Biopharmaceutical Sciences* 3 (1/2): 091-099 (1992).

Dalby, R.N., et al., "Inhalation Therapy: Technological Milestones in Asthma Treatment", *Advanced Drug Delivery*, 55: 779-791 (2003).

Darrington, et al., "Evidence for a Common Intermediate in Insulin Deamidation and Covalent Dimer Formation: Effects of pH and Aniline Trapping in Dilute Acidic Solutions", *Journal of Pharmaceuticals Sciences*, 84(3): 275-282 (1995).

D'Cruz, N. "Relationship Between Protein Thermal Stability and Glass Transition in Gelatin Polyol and Gelatin-Water Mixtures", Proceedings of 2004 Meeting IFT, Jul. 12-16, 2004, Las Vegas, NV, Session 17E, Food Chemistry: Proteins, [on-line].

Decarlo, S., et al., "Unexpected Property of Trehakose as Observed by Cyro-Electron Microscopy", *Journal of icroscopy*, 196(1): 40-45 (1995).

Dellamary et al. "Hollow Porous Particles in Metered Dose Inhalers" Pharm Research 17(2): 168-174 (2000).

DeYoung, "The AeroDose Multidose Inhaler Device Design and Delivery Characteristics", *Respiratory Drug Delivery VI*, p. 91 (1998).

D'Hondt, "Possible Approaches to Develop Vaccines Against Hepatitis A", *Vaccine* 10 (Supplement 1): S48-S52 (1992).

Dose, et al., "Survival in Extreme Dryness and DNA-Single-Strand Breaks", *Advances in Space Research*, 12(4)221-229 (1992).

Dunbar et al., "Dispersion and Characterization of Pharmaceutical Dry Powder Aerosols," KONA (Feb. 26, 1998).

During, M.J., et al., "Long-Term Behavioral Recovery in Parkinsonian Rats by an HSV Vector Expressing Tyrosine Hydrosylase", *Science*, 266(5189): 856-857 (Nov. 1994).

Duzgunes et al. "Studies on the Mechanism of Membrane Fusion. Role of Head-Group Composition in Calcium- and Magnesium-induced Fusion of Mixed Phospholipid Vesticles" Biochim Biophys Acta 642: 182-195 (1981).

Ebara et al. "interactions of Calcium Ions with phospholipid Membranes" Langmuir 10: 2267-2271 (Apr. 1994).

Edwards, A.D., et al., "Crystallization of Pure Anhydrous Polymorphs of Carbamazepine by Solution Enhanced Dispersion with Supercritial Fluids (SEDS™)", *Journal of Pharmaceutical Sciences*, 90(8): 1115-1124 (2001).

Edwards, et al., "Large Porous Particles for Pulmonary Drug Delivery", *Science*, vol. 276, pp. 1868-1871 (Jun. 1997).

Eisenberg et al. "Adsorption of Monovalent Cations to Bilayer Membranes Containing Negative Phospholipids" Biochemistry 18(23):5213-5223 (1979).

Eleutherio, et al., "Role of the Trehalose Carrier in Dehydration Resistence of *Saccharomyces cerevisiae*", Biochimica et Biophysica Acta, 1156: 263-266 (1993).

Elkordy, et al., Integrity of Crystalline Lysozyme Exceeds that of a Spray-Dried Form, *International Journal of Pharmaceutics*, 247: 79-90 (2002).

Fahy, et al., "Vitrification as an Approach to Cryopreservation", Cryobiology, 21: 407-426 (1984).

Fakes, M., et al., "Moisture Sorption Behavior of Selected Bulking Agents Used in Lyophilized Products", *PDA J. Pharm. Sci. Technol.* 54(2) 144-149, Abstract only [on-line] [retrieved Sep. 25, 2005] Retrieved from the Internet (2002).

Finar, I.L., "§14. Trehalose, m.p. 203° C", under "Carbohydrate" Organic Chemistry, vol. 2, Stereochemistry and the Chemistry of Natural Products, 5th edition, Longman, p. 323 (1996).

Forbes, R.T., et al., "Water Vapor Sorption Studies on the Physical Stability of a Series of Spray-Dried Protein/Sugar Powders for Inhalation", *Journal of Pharmaceutical Sciences*, 87(11): 1316-1321 (1998).

Franks, "Accelerated Stability Testing of Bioproducts: Attractions and Pitfalls", *Tibtech*, 12: 114-117 (1994).

Franks, "Freeze Drying: From Empiricism to Predictability", Cyro-Letters, 11: 93-110 (1990).

Franks, "Materials Science and the Production of Shelf-Stable Biologicals", *Pharmaceutical Technology International*, 24: 24-34 (Oct. 1991).

Franks, "Separation, Improved Freeze-Drying, an Analysis of the Basic Scientific Principles", *Process Biochemistry*, 24(1): iii-vii (1989).

French, Donna L., et al., "The Influence of Formulation on Emission, Deaggregation and Deposition of Dry Powders for Inhalation," *J. Aerosol Science*, vol. 27, No. 5, pp. 769-783 (1996).

Fukuoka, et al., "Glassy State of Pharmaceuticals. V. Relaxation During Cooling and Heating of Glass by Differential Scanning Calorimetry", *Chem. Pharm. Bull* 39(8): 2087-2090 (Aug. 1991).

Goldbach et al. "Spray-Drying of Liposomes for a Pulmonary Administration I. Chemical Stability of Phospholipids" Drug Develop Ind Pharm 19(19): 2611-2622 (1993).

Gonda, et al., "Characterization of Hygroscopic Inhalation Aerosols", In: Particle Size Analysis, (Eds. N.G. Stanley-Wood and T. Allen, Wiley Heyden Ltd., NY), pp. 31-43 (1981).

Gordon et al. "Ideal Copolymers and the Second-Order Transitions of Synthetic Rubbers. I. Non-Crystalline Copolymers" J. Appl. Chem. 2: 493-500 (Sep. 1952).

Green, et al., "Phase Relations and Vitrification in Saccharide-Water Solutions and the Trehalose Anomaly", J. Phys. Chem., 98: 2880-2882 (1989).

Green, et al., "The Protein-Glass Analogy: Some Insights from Homopeptide Comparisons", *J. Phys. Chem.*, 98: 13780-13790 (Apr. 1994).

Gupta, A., et al., "Single Virus Particle Mass Detection Using Microresonators with Nanoscale Thickness", *Applied Physics Letters*, 84(11): 1976-1978 (2004).

Hahn, et al., "Solid Surfactant Solutions of Active Ingredients in Sugar Esters", Pharmaceutical Research, 6: 958-959 (1989).

Hancock et al. "Characteristics and Significance of the Amorphous State in Pharmaceutical Systems" J. of Pharmaceutical Sciences 86(1): 1-12 (Jan. 1997).

Hancock et al. "The Relationship Between the Glass Transition Temperature and the Water Content of Amorphous Pharmaceutical Solids" Pharm Research 11(4):471-477 (1994).

Hancock, B.C., et al., "The Effect of Temperature on Water Vapor Sorption by Some Amorphous Pharmaceutical Sugars", *Pharmaceutical Development and Technology*, 4(1): 125-131 (1999).

Hancock, et al., "The Use of Solution Theories for Predicting Water Vapor Absorbtion by Amorphous Pharmaceutical Solids: A Test of the Flory-Huggins and Vrentas Models", Pharmaceutical Research, 10(9): 1262-1267 (1993).

Hancock, et al., "A Pragmatic Test of Simple Calorimetric Method for Determining the Fragility of some Amorphous Pharmaceutical Materials", *Pharm. Res.*, 15(5): 762-767 (1998).

Hancock, et al., "Molecular Mobility of Amorphous Pharmaceutical Solids Below Their Glass Transition Temperatures", *Pharmaceutical Research*, 12(6): 799-806 (1995).

Hanes, et al., "Porous Dry-Powder PLGA Microspheres coated with Lung Surfactant for Systematic Insulin Delivery via the Lung", *Proc. Int'l. Symp. Control Rel. Bioactive Matter*, 24: 5758 (1997).

Hanes, Justin, "Polymer Microspheres for Vaccine Delivery", Thesis (Ph.D.), dated Sep. 1996, archived by MIT library Jul. 31, 1997 and catalogued on Dec. 5, 1997.

Harwood, C.F., "Compact Effect on Flow Property Indexes for Powders", *J. Pharm. Sci.*, 60:161-163 (1971).

Hauser et al. "Comparative Structural Aspects of Cation Binding to Phosphatidylserine Bilayers" Biochim Biophys Acta 813: 343-346 (1985).

Hauser et al. "Interactions of Divalent Cations with Phosphatidylserine Bilayer Membranes" Biochemistry 23: 34-41 (1984).

Heitefuss, R., et al., "The Stabilization of Extracts of Cabbage Leaf Proteins by Polyhydroxy Compounds for Electrophoretic and Immunological Studies", Archives of Biochemistry and Biophysics, 85: 200-208 (1959).

Heller, Martin C., et al., *Protein Formulation and Lyophilization Cycle Design: Prevention of Damage Due to Freeze-Concentration Induced Phase Separation* 63 Biotechnology & Bioengineeting, 166-174 (1999).

Herrington, T.M., et al., "Physico-Chemical Studies on Sugar Glasses. I. Rates of Crystallization", Journal of Food Technology, 19: 409-425 (1984).

Hickey, A. J. et al., "Behavoir of Hygroscopic Pharmaceutical Aerosols and the Influence of Hydrophobic Additives," *Pharmaceutical Research* 10(1):1-7 (1993).

Hickey, A. J. et al., "Methods of Aerosol Particle Size Charaterization," *Pharmaceutical Inhalation Aerosol Technology* 8:219-253 (1992).

Hoener, Betty-Ann et al., "Factors Influencing Drug Absorption and Availability" *Modern Pharmaceutics*, Gilber S. Banker et al., eds., Marcel Dekker Inc., Chapter 4, pp. 121-153 (1996).

Hrkach et al., "Poly-lactic-co-amino acid) graft copolymers: A class of . . . polymers for bioapplication, " Hydrogels and Biodegradable Polymers for Bioapplication (1996), ACS Symposium Series No. 627, pp. 93-101.

Hrkach et al., "Synthese of polylactic acid-co-lysine graft copolymers," Macromolecules 1995, 28(13):4736-4739.

Huster et al. "Investigation of Phospholipid Area Compression Induced by Calcium-Mediated Dextran Sulfate Interaction" Biophys J. 77(2): 879-867 (Aug., 1999).

Huster et al. "Strength of Ca(2+) Binding to Retinal Lipid Membranes: Consequences for Lipid Organization" Biophys J. 78(6): 3011-3018 (Jun. 2000).

Ibrahim, A. L. et al., "Sprah Vaccination With an Improved F Newcastle Disease Vaccine. A Comparison of Efficacy With the B1 and La Sota Vaccines," Br. Vet. J. 139:213-219 (1983).

Igaki, N. et al., "The Inhibition of the Maillard Reaction by L Lysine In-Vitro," *J. Jpn. Diabetes Soc.*, english abstract 34(5):403-407 (1991).

Iglesias et al., "Adsorption Isotherm of Amorphous Trehalos", *J. Sci. food Agric*. 75:183186 (1997).

Jacobson et al. "Phase Transition and Phase Separations in Phospholipid Membranes Induced by Changes in Temperature, pH, and Concentration of Bivalent Cations" 14(1): 152-161 (1975).

Jameel, F. et al., "Freeze Drying Properties of Some Oligonucleotides", *Pharmaceutical Development and Technolology* 6(2):151-157 (2001).

Jovanovic-Peterson, L. et al., "Jet-injected insulin is associated with decreased antibody production and postprandial glucose variability when compared with needle injected insulin in gestational diabetic women, " *Diabetes Care* 16(11):1479-1484 (Nov. 1993).

Kachura, "Method of Drying Lactic Acid Bacteria," Vinodelie I Vinogradarstvo SSSR 2:49-50, English Abstract only, one page (1985).

Kanna, K. et al., "Denaturation of Fish Muscle Protein by Dehydration" *Bull Tokai Reg. Fish. Res. Lab.* 77:70-76 English abstract (1974).

Karmas. R, et al., "Effect of Glass Transition on Rates of Nonenzymatic Browning in Food Systems," *J. Agric. Food Chem.* 40:873-879 (1992).

Khan, R. "Chemistry and New Uses of Sucrose: How Important?" Pure & Appl. Chem. 56(7):833-844 (1984).

Khan, R. "Cyclic Acetals of 4,1', 6'-Tricholoro4,1', 6'-Trideoxy-Galacto-Sucrose and Their Conversion Into Methyl Ether Derivatives," Garb. Res. 198:275-283 (1990).

Klein, T. M. et al., "High Velocity Microprojectiles for Delivering Nucleic Acids Into Living Cells," Nature 327:70-73 (1987).

Kwon et al. "Calcium Ion Adsorption on Phospholipid Bilayers—Theoretical Interpretation" J Jap Oil Chem Soc 43(1): 23-30 (1994).

Labrude, P. et al., "Protective Effectof Sucrose on Spray Drying of Ocxyhemoglobin," Journal of Pharmaceutical Sciences. 78(3):223-229 (1989).

Labuza el al., "Glass Transition Temperatures of Food Systems", [on-line] [retrieved Sep. 2005] Retrieved from the Internet pp. 1-31 (Jan. 1992).

Lai, M. C. et al., "Solid-State Chemical Stability of Proteins and Peptides", *Journal of Pharmaceutical Sciences* 88(5):489-500 (1999).

Laube, B. L. et al., "Targeting Aerosol Deposition in Patients With Cystic Fibrosis, Effects of Alterations in Particle Size and Inspiratory Flow Rate", *Chest* 118(4): 1069-1076 (2000).

Ledt, F., et al., "New Aspects of the Maillard Reaction in Foods and in the Human Body," *Ang. Chem. Int. Ed.* Engl. 29:565-594 (Jun. 1990).

Lee, C. K. Developments in Food Carbohydrate—2nd edition Applied Science Publishers, London, Table of Contents, 4 pages (1980).

Lee, G., "Spray Drying of Proteins," Chapter 6, *Rational Design of Stable Protein Formulations, Theory and Practice*, J. F. Carpenter & M. Manning, pp. 135-158 (2002).

Lehninger, Albert L. *The Molecular Basis of Cell Structure and Function* Biochemistry, Chapter 31, 859-890 (Worth Publishers Inc., 2nd edition, 1975).

Leslie, S. B. et al., "Trehalose and sucrose protect both membranes and proteins in intact bacteria during drying", *Appl. Env. Microbiol.* 61(10): 3592-3597 (1995).

Leuner, C. et al., "Improving Drug Solubility for Oral Delivery Using Solid Dispersions", *European Journal of Pharmaceutics and Biopharmaceutics* 50:47-60 (2000).

Levine et al., "Another View of Trehalose for Drying and Stabilizing Biological Materials," *Biopharm* 5:36-40 (1992).

Li, Z. et al., "Realistic In Vitro Assessment of Dry Powder Inhalers", *Respiratory Drug Delivery VIII*, pp. 687-689 (2002).

Lin, S.-Y. et al., "Solid Particles of Drug-β-Cyclodextrin Inclusion Complexes Directly Prepared by a Spray-Drying Technique", International Journal of Pharmaceutics, 56:249-259 (1989).

Lis et al. "Adsorption of Divalent Cations to a Variety of Phosphatidylcholine Bilayers" Biochemistry 20: 1771-1777 (1981).

Lis et al. "Binding of Divalent Cations to Dipalmitoylphosphatidytcholine Bilayers and its Effect on Bilayer Interaction" Biochemistry 20: 1761-1770 (1981).

Liu, Jinsong et al., "Dynamics of Pharmaceutical Amorphous Solids: The Study of Enthalpy Relaxation by Isothermal Microcalorimetry", *Journal of Pharmaceutical Sciences* 91(8):1853-1862 (2002).

Louey, M. D. et al., "Controlled Release Products for Respiratory Delivery", *APR*, 7(4):82-87 [online] retrieved 09/20051 <http://www.americanpharmaceuticalreview.com.article.aspx?article=77 (2004).

Louis, P. et al., "Survival of *Escherichia coli* During Drying and Storage in the Presence of Compatible Solutes" *Appl. Microbiol. Biotechnol.* 41:684-688 (1994).

Lueckel, B. et al., "Effects of Formulation and Process Variables on the Aggregation of Freeze-Dried Interleukin-6 (IL-6) After Lyophilization and on Storage", *Pharmaceutical Development and Technology* 3(3):337-346 (1998).

MacKenzie, "Collapse During Freeze Drying-Qualitative and Quantitative Aspects." *Freeze Drying and Advanced Food Technology*, edited by Goldblith, Rey and Rothmayr: 277-307 (1975).

Makower, B. et al., "Equilibrium Moisture Content and Crystallization of Amorphous Sucrose and Glucose," Agric. and Food Chem. 4(1):72-77 (1956).

Martin, A. et al., States of Matter and Phase Equilibria Physical Pharmacy, Physical Chemical Principles in the Pharmaceutical Sciences, 3rd. ed., Chapter 4, 62-92 (1983).

Masinde, Lwandiko E., et al., "Aerosolized Aqueous Suspension of Poly(L-lactic Acid) Microspheres,", 100 *International Journal of Pharmaceutics*, pp. 123-131 (1993).

Masters, K Spray Drying Handbook, 5th ed., Chapters 13 and 15, pp. 491-537 and 587-642 (1991).

Masters, K. Spray Drying Handbook, England; Longman Scientific & Technical and John Wiley & Sons, Inc., 5th ed. Chapter 8, pp. 309-352 (1991).

Matsuda, Y. et al., "Amorphism and Physicochemical Stability of Spray Dried Frusemide," *J. Pharm,. Pharmacol.* 44:627-633.

Mattern et al., "Formulation of Proteins in Vacuum-Dried Glasses. II. Process and Storage Stability in Sugar-Free Amino Acid Systems", Pharmaceutical Development & Technology 4(2):199-208 (1999).

Miller, D. P. et al., "Stabilization of Lactate Dehydrogenase Following Freeze Thawing and Vacuum-Drying in the Presence of Trehalose and Borate", *Pharmaceutical Research* 15(8):1215-1221 (1998). (7 pages) 7 patents [ISI abstract].

Millqvist-Fureby et al. "Spray-Drying of Trypsin—Surface Characterisation and Activity Preservation" Int. J. Pharm. 188: 243-253 (1999).

Millqvist-Fureby et al. "Surface Characterisation of Freeze-Dried Protein/Carbohydrate Mixtures" Int. J. Pharm. 191: 103-114 (1999).

Molina, M. C. et al., "The Stability of Lyophilized Lipid/DNA Complexes During Prolonged Storage," J. Pharm. Sci. 93(9):2259-2273, abstract only, one page, [on-line] [retrieved Sep. 2005] Retrieved from the Internet , (2004).

Monnier et al., *Mechanisms of Protection Against Damage Mediated by the Maillard Reaction in Aging Gerontology* 37:152-165 (1991).

Mouradian, R. et al., "Degradation of Functional Integrity During Long-Term. Storage of a Freeze-Dried Biological Membrane", Cryobiology 22: 119-127 (1985).

Moynihan et al., "Dependence of the Glass Transition Temperature on Heating and Cooling Rate", J. Physical. Chem. 78(26):2673-2677 (1974).

Muller, et al., "On the Influence of Molecular Forces on the Deformation of an Elastic Sphere and Its Sticking to a Rigid Plane", *J. Colloid Interface Sci.*, 77: 91 (1980).

Mumenthaler, M. et al., "Feasibility Study on Spray-Drying Protein Pharmaceuticals: Recombinant Human Growth Hormone and Tissue-Type Plasminogen Activator," *Clinical Research* 11(1): 12-20 (1994).

Murphy, B. R. et al., "Chapter 19: Immunization Against Viruses", in *Fields of Virology*, 2nd Edition, vol. 1, Raven Press, pp. 469-502 (1990).

Murphy, Brian R. et al., *Fields Virology*, vol. 1, Chapter 16, *Immunization Against Virus Disease*, 467, at p. 468, first full paragraph, first column, lines 26-33 (Bernard N. Fields et al. eds., Lippincott-Raven Publishers, 3rd ed. 1996).

Mutterlein, et al., "New Technology for Generating Inhalation Aerosols—Preliminary Results with the Piezoelectrical Pocket-Inhaler", *J. Aerosol Med.*, 1: 231 (1988).

Nabel, G. J. et al., "Direct Gene Transfer With DNA-Liposome Complexes in Melanoma," Proc. Nat. Acad. Sci. 90:11307-11311 (1993).

Nabel, G. J. et al., "Immunotherapy of Malignancy by In Vivo Gene Transfer Into Tumors," *Hum. Gene. Ther*. 3(4): 3 99-4 10 (Aug. 1992) Abstract only [on-line].

Naini, V. et al., "Particles for Inhalation Produced by Spray Drying and Electrostatic Precipitation of Different Protein-Sugar Solutions". *Respiratory Drug Delivery V*, pp. 382-384 (1996).

Naini, V. et al., "Physicochemical Stability of Crystalline Sugars and Their Spray-Dried Forms: Dependence Upon Relative Humidity and Suitability for Use in Powder Inhalers", *Drug Development and Industrial Pharmacy* 24(10):895-909 (1998).

Natarajan, P., Crystallization Conditions for VIPER Entries [on-line] [retrieved Nov. 4, 2004] Retrieved from the Internet 5 pages (last updated Jan. 3, 2002).

Nektar Notice of Opposition against EP 939622 B1 (May 12, 2003).

Nektar U.S. Appl. No. 08/044,358, "Compositions and Methods for Nucleic Acid Delivery to the Lung" filed by Patton et al. on Apr. 7, 1993, assigned to Inhale Therapeutic Systems.
Niven, R. W., "Delivery of Biotherapeutics by Inhalation Aerosol," *Critical Reviews in Therapeutic Drug Carrier Systems*, 12(2&3):151-231 (1995).
Niven, R. W., "Delivery of Biotherapeutics by Inhalation Aerosols," *Pharmaceutical Technology* 72-75, 80 (Jul. 1993).
Nornerg, J. et al., "Glass Transition in DNA From Molecular Dynamics Simulation", *Proc. Natl. Acad. Sci. USA* 93:10173-10176 (1996).
Notter, R.H., "Physical Chemistry and Physiological Activity of Pulmonary Surfactants", In: Surfactant Replacement Therapy (Eds. Shapiro and Notter, Alan R. Liss, Inc., New York), Chapter 2, pp. 19-71 (1989).
Odegard, P. S. et al., "Inhaled Insulin: Exubera", *The Annals of Pharmacotherapy* 39:843-853 (2005).
Ohtake, S. et al., "Effect of pH, Counter Ion and Phosphate Concentration on the Glass Transition Temperature of Freeze-Dried Sugar-Phosphate Mixtures", *Pharmaceutica Research* 21(9):1615-1621(2004).
Okamoto, H. et al., "Dry Powders for Pulmonary Delivery of Peptides and Proteins", *KONA* 20:71-83 (2002).
Oksanen et al., "The Relationship between the Glass Transition Temperature and Water Vapor Absorption by Poly(Vinylpyrrolidone)," *Pharmaceutical Research* 7(6): 654-657 and errata on p. 974(1990).
Okumura, K. et al., "Intratracheal Delivery of Calcitonin Dry Powder in Rats and Human Volunteers," *S.T.P. Pharmaceutical Sciences* 4(I):5 pages (Jan., Feb. 1994).
Onodera et al., "Glass Transition of Dehydrated Amorphous Solid", *Bull. Chem. Soc.* Japan 41(9):222 (1968).
Opposition Papers of European Patent No. EP 1019021 (European Application No. 98950826.2) Dated: Jun. 3, 2004 through Nov. 15, 2006.
Owens, D. R. et al., "Alternative Routes of Insulin Delivery," *Diabetic Medicine* 20:886-898 (2003).
Palmer, K.J., et al., "X-Ray Diffractometer and Microscopic Investigation of Crystallization of Amorphous Sucrose", Agricultural and Food Chemistry 4(1): 77-81 (Jan. 1956).
Parasassi et al. "Calcium-Induced Phase Separation in Phospholipid Bilayers. A Fluorescence Arisotropy" Cellular and Molecul Bio 32(3): 261-266 (1986).
Parks, "Studies on Glass. II The Transition Between the Glassy and Liquid States in the Case of Glucose", *Journal of Physical Chemistry* 1366-1379 (1928).
Patel, M. M. et al., "Degradation Kinetics of High Molecular Weight Poly(L Lactide) Microspheres and Release Mechanism of Lipid: DNA Complexes", *Journal of Pharmaceutical Sciences*, 93(10): 2573-2584 (2004).
Pearlman et al., "Formulation Strategies for Recombinant Proteins: Human Growth Hormone and Tissue Plasminogen Activator", *Therapeutic Peptides and Proteins, Formulation, Delivery and Targeting*, Cold Spring Harbour, New York, pp. 23-30 (1989).
Pekarek et al. "Double-walled polymer microspheres for controlled drug release," Nature 367:258-260 (1994).
Persson, G. and J.E. Wiren, The bronchodilator response from inhaled terbutaline is influenced by the mass of small particles: a study on a dry powder inhaler (Turbuhalter) Eur. Respir J. 2:253-256 (1989).
Phillips, E. et al., "Size Reduction of Peptides and Proteins by Jet-Milling", *Respiratory Drug Delivery VI*, pp. 161-167 (1998).
Pikal et al., "Thermal Decomposition of Amorphous β-Lactam Antibacterials", *Journal of Pharmaceutical Science* 66(9): 1312-1316 (Sep. 1997).
Pikal, M. J. et al., "The Stability of Insulin in Crystalline and Amorphous Solids: Observation of Greater Stability for the Amorphous Form", *Pharmaceutical Research* 14(10):1379-1387 (1997).
Pikal, M. J. et al., Errata of "The Stability of Insulin in Crystalline and Amorphous Solids: Observation of Greater Stability for the Amorphous Form," *Pharmaceutical Research* 15(2):362-363 (1998).
Pikal, M. J., "Freeze-Drying of Proteins Part II: Formulation Selections," *Biopharm* 3(8):26-30 (Oct. 1990).
Pisecky, J., "2. Evaporation and Membrane Filtration", *Handbook of Milk Powder Manufacture*, Niro A/S, Denmark, p. 3 (1997).

Pocchiari, M. et al., "Amphotericin B: A Novel Class of Antiscrapie Drugs," J Infect. Dis. 160(5):795-802 (Nov. 1989).
Prestrelski, S. J. el al., "Optimization of Lyophilization Conditions for Recombinant Human Interleukin-2 by Dried-State Conformational Analysis Using Fourier-Transform Infrared Spectroscopy," *Pharmaceutical Research* 12(9):1250-1259 (1995).
Prestrelski, S. J. et al., "Separation of Freezing- and Drying-Induced Denaturation of Lyophilized Proteins Using Stress-Specific Stabilization," *Archives of Biochemistry and Biophysics* 303(2):465-473 (Jun. 1993).
Quan, C. Protein Science 4(2): 148, Abstract No, 490-T (1995).
Ramanujam, R. et al., "Ambient-Temperature-Stable Molecular Biology Reagents," *Biotechniques* 14(3):470-473 (1993).
Reboiras, M.D. "Activity Coefficients of $CaCl_2$ and $MgCl_2$ in the Presence of Dipalmitoylphosphatidylcholine-Phosphatidylinositol Vesicles in Aqueous Media" Bioelectrochemistry and Bioenergetics 39: 101-108 (1996).
Ringe, D. et al., "The Glass Transition in Protein Dynamics: What it is, Why it Occurs, and How to Exploit It", *Biophys. Chem.* 105(2-3):667-680, Abstract only, [on-line] [retrieved Nov. 19, 2004] Retrieved from the Internet (2003).
Roos, "Phase Transitions of Mixtures of Amorphous Polysaccharides and Sugars," *Biotechnology Progress* 7(1): 49-53 (1991).
Rosen, Surfactants and Interfacial Phenomena, Second Edition, John Wiley & Sons, New York, pp. 326-329 (1989).
Roser, B., "Trehalose Drying: A Novel Replacement for Freeze Drying" *Biopharm* 4:47-53 (1991).
Roser, B., "Trehalose, A New Approach to Premium Dried Foods," *Trends in Food Sci. and Tech.* pp. 166-169 (Jul. 1991).
Roser, et al., "A Sweeter Way to Fresher Food" *New Scientist* pp. 25-28 (May 15, 1993).
Roth, C. et al., "Production of Hollow Spheres," Paragamon Press, vol. 19 (No. 7), p. 939-942, (Feb. 26, 1988).
Royall et al. "Characterisation of Moisture Uptake Effects on the Glass Transitional Behaviour of an Amorphous Drug Using Modulated Temperature DSC" Int. J. Pharm. 192: 39-46 (1999).
Sacchetti, et al., "Spray-Drying and Supercritical Fluid Particle Generation Techniques", *Inhalation Aerosols: Physical and Biological Basis for Therapy*, A.J. Hickey, ed., Marcel Dekkar, New York, Chapter 11, p. 337 (1996).
Saleki-Gerhardt, A. et al., "Hydration and Dehydration of Crystalline and Amorphous Forms of Raffinose," *Journal of Pharmaceutical Sciences*, 84(3):318-323 (Mar. 1995).
Saleki-Gerhardt, A. et al., "Non-Isothermal and Isothermal Crystallization of Sucrose From the Amorphous State," *Pharmaceutical Research* 11 (8):1166-1173 (1994).
Sambrook, et al., *Molecular Cloning: A Laboratory Manual*, 2nd. ed., "Concentrating Nucleic Acids: Precipitation with Ethynol or Isopropanol", pp. E.10-E.17, Cold Spring Harbor Laboratory Press (1989).
Sanchez, J. et al., "Recombinant System for Overexpression of Cholera Toxin B Subunit in Vibro Cholerae as a Basis for Vaccine Development" Proc. Natl. Acad. Sci. USA 86:481-485 (1989).
Sarkar and Moore, "Immunization of Mice Against Murine Mammary Tumor Virus Infection and Mammary Tumor Development," Cancer Research 38:1468-1472 (1978).
Satoh, Koichi, "Determination of Binding Constants of $Ca^{2+}$, $Na^+$, and $Cl^-$ Ions to Liposomal Membranes of Dipalmitaoylphosphatidylcholine at Gel Phase by Particle Electrophoresis", Biochem. Biophys. Acta 1239:239-248 (1995).
Schamblin and Zografi. "Enthalpy Relaxation in Binary Amorphous Mixtures Containing Sucrose" *Pharmaceutical Research* 15(12): 1828-1834 (Dec. 1998).
Schebor, C. et al., "Color Formation Due to Non-Enzymatic Browning in Amorphous, Glassy, Anhydrous, Model Systems", *Food Chemistry* 65:427432 (1999).
Schram, L. "The Language of Colloid and Interface Science, A Dictionary of Terms", American Chem. Soc. p. 157 (1993).
Sciarra et al., "Aerosols", *Remington's Pharmaceutical Sciences*, Chap. 93, 17 Ed., Mack Publishing Company, Alfonso R. Gennaro, editor, pp. 1662-1677 (1985).

Sebhatu, T. et al., "Assessment of the Degree of Disorder in Crystalline Solids by Isothermal Microcalorimetry," *International Journal of Pharmaceutics* 104:135-144 (1994).

Seddon, J.M. "Structure of the Inverted Hexagonal (HII) Phase, and Non-Lamellar Phase Transitions of Lipids" Biochim Biophys Acta 1031:1-69 (1990)., in particular p. 43-44 and 49-50.

Seelig, Joachim *Handb. Met.—Ligand Interact. Biol. Fluids: Bioinorg. Chem.* § Metal Ion Interactions with Lipids: 698-706 (1995).

Sellers, S. P. et al., "Dry Powders of Stable Protein Formulations From Aqueous Solutions Prepared Using Supercritical CO2-Assisted Aerosolization", *Journal of Pharmaceutical Sciences*, 90(6): 785-797 (2001).

Serajuddin, A. T. M. et al. "effect of Thermal History on the Glassy State of Indapamide," J. Pharm. Pharmacol. 38:219-220 (1986).

Shah et al. "The Ionic Structure of Sphingomyelin Monolayers" Biochem Biophys Acta 135: 184-187 (1967).

Shalaev, E.Y. et al., "How Does Residual Water Affect the Solid-State Degradation of Drugs in the Amorphous State", *Journal of Pharmaceutical Sciences*, 85(11): 1137-111 (1996).

Shalaev, E.Y. et al., "Structural Glass Transitions and Thermophysical Processes in Amorphous Carbohydrates and Their Supersaturated Solutions," *J. Chem. Soc. Faraday Trans.* 91(10):1511-1517 (1995).

Sharma, V.K. et al., "Effect of Vacuum Drying on Protein-Mannitol Interactions: The Physical State of Mannitol and Protein Structure in the Dried State", AAPS PharmSciTech 5(1) Article 10:1-12 [on-line] [retreived] Retreived from the Internet (2004).

Shavnin et al. "Cholesterol Affects Divalent Cation-Induced Fusion and Isothermal Phase Transitions of Phospholipid Membranes" Biochim Biophys Acta 946: 405-416 (1988).

Simha et al. "On a General Relation Involving the Glass Temperature and Coefficients of Expansion of Polymers" J. Chem. Physics 37(5): 1003-1007 (Sep. 1962).

Singer et al., "Thermotolerance in *Saccharomyces cerevisiae*: the Yin and Yang of Trehalose", Tibtech 16:460-468. (1998).

Skrabanja et al., "Lyophilization of Biotechnology Products" *PDA J. Pharm. Sci Technol.* 48(6):311-7 (1994).

Slade and Levine, "Non-Equilibrium Behavior of Small Carbohydrate-Water Systems," Pure and Applied Chemistry, 60(12): 1841-1864 (1988).

Sokolov et al., "Glassy Dynamics in DNA: Ruled by Water of Hydration" *Journal of Chemical Physics* 110(14):7053-7057 (1999).

Sola-Penna, Mauro et al., *Stabilization Against Thermal Inactivation . . . : Why is Trehalose More Effective Than Other Sugars?* 360(I) Archives of Biochemistry and Biophysics 10-14, Article No. BB9809606, (Dec. 1998).

Sonner, C. et al., "Spray-Freeze-Drying for Protein Powder Preparation: Particle Characeterization and a Case Study With Trypsinogen Stability", *Journal of Pharmaceutical Sciences* 91(10):2122-2139 (2002).

SPI Polyols™ "What are Polyols? What do Polyols do? What are Polyols' functionality?", [on-line] [retrieved Jun. 25, 2004] Retrieved from the Internet one page (2003).

Stribling, R. et al., "Aerosol Gene Delivery in Vivo," *Proc. Natl. Acad. Sci*. 89:11277-11281 (Dec. 1992).

Strickley, R. G. et al., "Solid-State Stability of Human Insulin II. Effect of Water on . . . in Lyophiles from pH 2-5 Solutions: Stabilization Against Covalent Dimer Formation", *Journal of Pharmaceutical Sciences* 86(6):645-653 (1997).

Strom, A. R. and Kaasen. L. "Trehalose Metabolism in *Escherichia coli*: Stress Protection and Stress Regulation of Gene Expression", *Molecular Microbiology* 8(2):205-210 (1993).

Stubberud, L. et al., "The Use of Gravimetry for the Study of the Effect of Additives on the Moisture-Induced Recrystallisation of Amorphous State", *International Journal of Pharmaceutics* 163:145-156 (1998).

Sugisaki et al. "Calorimetric Study of the Glassy State. IV. Heat Capacities of Glassy Water and Cubic Ice" Bulletin of the Chemical Society of Japan 41: 2591-2599 (Nov. 1968).

Sukenik et al. "Enhancement of a Chemical Reaction Rate by Proper Orientation of Reacting Molecules in the Solid State", J. Am. Chem. Soc. 97: 5290-5291 (Sep. 1975).

Sussich, F. et al., "Reversible Dehydration of Trehalose and Anhydrobiosis: From Solution State to an Exotic Crystal?", *Carbohydrate Research* 34: 165-176 (2001).

Takahashi et al., "Induction of CD8+ cytotoxic T cells by immunization with purified HIV-1 envelope protein in ISCOMs", Nature 344:873-875 (Apr. 1990).

Tarara, T. et al. "Characterization of Suspension-Based Metered Dose Inhaler Formulations Composed of Spray-Dried Budesonide Microcrystals Dispersed in HFA," J. Pharm Res, vol. 21, No. 9, pp. 1607-1614 (Sep. 2004).

Tarelli, E. et al., "Additives to Biological Substances. 111. The Moisture Content and Moisture Uptake of Commonly Used Carrier Agents . . . in the Preperation of International Biological Standards," Journal of Biological Standardization 15:331-340 (1987).

Tatulian, S.A. "Binding of Alkaline-Earth Metal Cations and Some Anions to Phosphatidylcholine Liposomes" Eur. J. Biochem. 170: 413-420 (1987).

Tatulian, S.A. "Evalutation of Divalent Cation Binding to Phosphatidylserine Membranes by an Analysis of Concentration Dependence of Surface Potential" J. Colloid Interface Science 175: 131-137 (1995).

Thatcher, E., "Quantitation of Virus" [on-line] Retrieved from the internet www.sonoma.edu/users/t/thatcher/biol383/lab.htm>, (last updated Jan. 5, 2002).

Timko et al., "Thermal Analysis Studies of Glass Dispersion Systems", *Drug Devel. Ind. Pharm.* 10:425451 (1984).

To et al., "Collapse. a Structural Transition in Freeze Dried Carbohydrates", *J. Fd. Technol.* 13:567-581 (1978).

Toyama, A. (ed) *Handbook of Natural Product for food processing*, 9th Edition, Osaka, Japan, Shokuhin to Kagaku Sha, pp. 384 and 495 (ISBN4-87994-048-8),(1986).

Underwood et al., "A Novel Technique for the Administration of Bronchodilator Drugs Formulated as Dry Powders to the Anaesthetized Guinea Pig", *J. of Pharmacological Methods*, vol. 26, pp. 203-210, 1991.

Uritani, M. et al., "Protective Effect of Disaccharides on Restriction Endonucleases During Drying Under Vacuum." *J. Biochem.* 117:774-779 (1995).

Vain et al., "Development of the particle inflow gun", *Plant Cell, Tissue and Organ Culture* 33:237-246 (1993).

Vavelyuk, O.L. et al., "Thermostability of DNA and Its Association with Vitrification", *Tsitologiya* 41(11):958-965 (1999).

Verstraeten et al. "Effects of Al(3+) and Related Metals on Membrane Phase State and Hydration: Correlation with Lipid Oxidation" Arch Biochem Biophys 375(2): 340-346 (Mar. 15, 2000).

Vidgren, M. T. et al., "Comparison of Physical and Inhalation Properties of Spray-Dried and Mechanically Micronized Disodium Cromoglycate," International Journal of Pharmaceutics 35:139-144 (1987).

Vromans, H. et al., "Studies on Tableting Properties of Lactose. VII. The Effect of Variations in Primary Particle Size and Percentage of Amorphous Lactose in Spray Dried Lactose Products," International Journal of Pharmaceutics 35:29-36 (1987).

Wang, et al., eds. *Stability and characterization of protein and peptide drugs*, Table of Contents, 6 pages (1993).

Welsh, D. T., "The Role of Compatible Solutes in the Adaptation and Survival of *Escherichia coli*," Ph.D. Thesis Submitted to Department of Biological Sciences, Univeristy of Dundee. pp. 1-262. (Aug. 1992).

Whipps et al. "Growth of Calcium Monohydrate at Phospholipid Langmuir Monolayers" J Cryst Growth 192: 243-249 (1998).

Whittier, E., "Lactose and its Utilization: A Review," *J. Dairy Sci*. 27(7)505-537 (Jul. 1994).

William and Leopold, "The Glassy State in Com Embryos" Plant Physiology 89:977-981 (1979).

Williams et al., "The Temperature Dependence of Relaxation Mechanisms in Amorphous Polymers and Other Glass Forming Liquids", The Journal of the American Chemical Society 77: 3701-3707 (1955).

Wolff, J. A. et al., "Grafting Fibroblasts Genetically Modified to Produce L-Dopa in a Rat Model of Parkinson Disease," Proc. Natl. Acad. Sci. 86:9011-9014 (Nov. 1989).

Xi, Y. G. et al., "Amphotericin B Treatment Dissociates in Vivo Replication of the Scrapie Agent From PrP Acummulation", *Nature* 356:598-601 (Apr. 1992).

Yamaguchi et al. "Adsorption of Divalent Cations onto the Membrane Surface of Lipid Emulsion" Colloids and Surfaces B: Biointerfaces 5: 49-55 (1995).

York, "Powdered Raw Materials: Characterizing Batch Uniformity," *Respiratory Drug Delivery IV, Programs and Proceedings*, edited by Byron, Dalby and Farr: 83-91 (1994).

Yoshida, H. et al., "Absorption of Insulin Delivered to Rabbit Trachea Using Aerosol Dosage Form," Journal of Pharmaceutical Sciences 68(5): 670 (May 1979).

Yoshinari, T. et al., "Moisture Induced Polymorphic Transition of Mannitol and its Morphological Transformation", *International Journal of Pharmaceutics*, 247:69-77 (2002).

Yoshioka, M. et al., "Crystallisation of Indomethacin From the Amorphous State Below and Above Its Glass Transition Membrane," *Journal of Pharmaceutical Sciences* 83(12):1700-1705 (Dec. 1994).

Zarif et al., "Amphotericin B. Cochleates as a Novel Oral Delivery System," International Symposium, p. 965-965 (1999).

Zubay, G. Biochemistry, Second Edition, pp. 211-256 "Nucleotides and Nucleic Acids" (1988).

Zubay, G. Biochemistry, Second Edition, pp. 39 & 169, Table 5-6 Major Steroid Hormones (1988).

Decision of the Board of Appeal, case No. T0041/07-3.3.02, of Apr. 14, 2010, mailing date May 18, 2010.

Office Action in U.S. Appl. No. 10/132,215 (patented as 7,141,236) dated Nov. 3, 2005.

Office Action in U.S. Appl. No. 10/327,510 (patented as 7,368,102) dated Jan. 14, 2007.

Office Action in U.S. Appl. No. 10/327,510 (patented as 7,368,102) dated May 4, 2006.

Office Action in U.S. Appl. No. 10/327,510 (patented as 7,368,102) dated Jun. 28, 2005.

Office Action in U.S. Appl. No. 10/327,510 (patented as 7,368,102) dated Sep. 20, 2004.

Office Action in U.S. Appl. No. 11/317,523 dated Apr. 10, 2009.

Office Action in U.S. Appl. No. 11/317,523 dated Sep. 25, 2008.

Office Action in U.S. Appl. No. 11/317,523 dated Oct. 1, 2009.

Office Action in U.S. Appl. No. 09/919,477 dated Feb. 11, 2004.

Office Action in U.S. Appl. No. 10/916,246 dated Mar. 19, 2009.

Office Action in U.S. Appl. No. 10/916,246 dated Mar. 25, 2008.

Office Action in U.S. Appl. No. 10/916,246 dated Jun. 19, 2007.

Office Action in U.S. Appl. No. 10/916,246 dated Oct. 28, 2009.

Johnson, Preparation of peptide and protein powders for inhalation, Advanced Drug Delivery Reviews 26 (1997) 3-15.

Mitra et al, Enhanced Pulmonary Delivery of Insulin by Lung Fluid and Phospholipids, International Journal of Pharmaceutics 217 (2001) 25-31.

Patton, John S. et al., "Inhaled Insulin", 35 Advanced Drug Delivery Reviews, pp. 235-247 (1999).

Todo, Hirosiki et al., "Effect of Additives on Insulin Absorption From Intratracheally Administered Dry Powders in Rats", 220 Int. J. of Pharmaceutics pp. 101-110 (1999).

Williams III, R.O., et al., "Formulation of a Protein with Propellant HFA 134a for Aerosol Delivery", 7 European J. of Pharmaceutical Sciences, pp. 137-144 (1998).

* cited by examiner

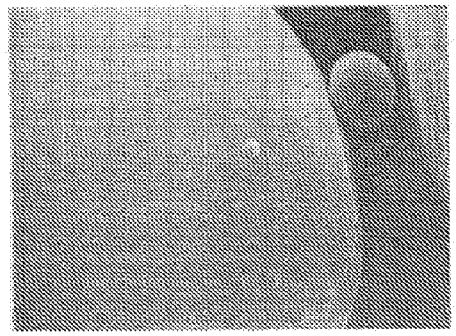 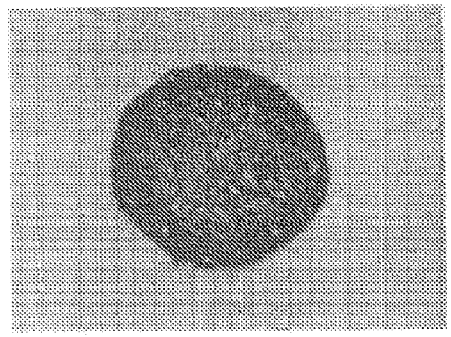
PFC/PC = 0
FIG. 1A-1  FIG. 1A-2
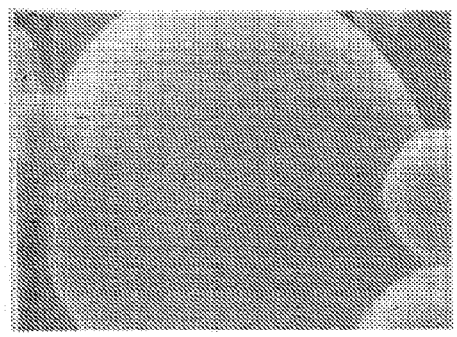 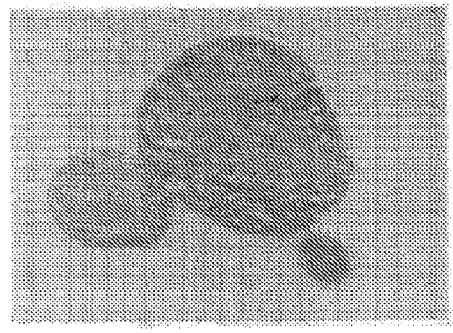
PFC/PC = 1.1
FIG. 1B-1  FIG. 1B-2
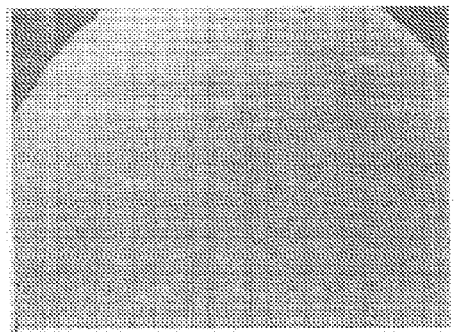 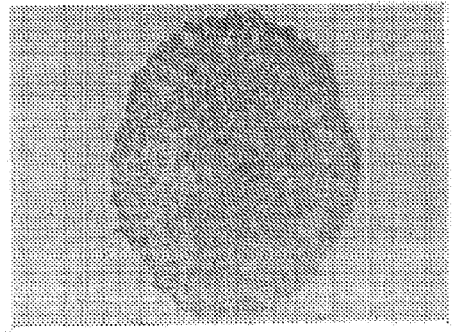
PFC/PC = 2.2
FIG. 1C-1  FIG. 1C-2

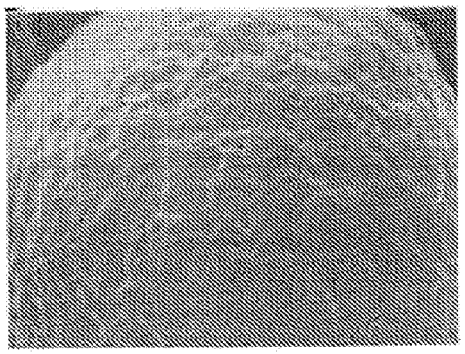 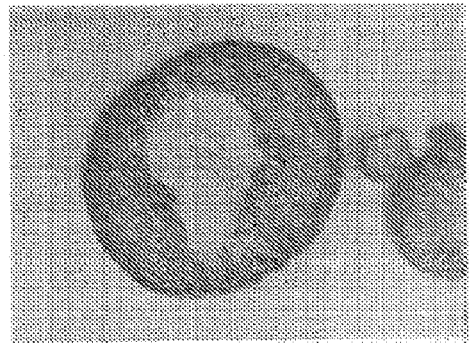
PFC/PC = 4.8
FIG. 1D-1    FIG. 1D-2
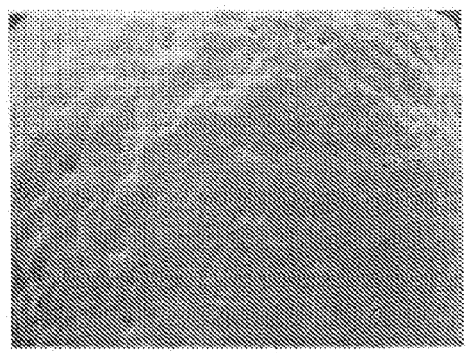 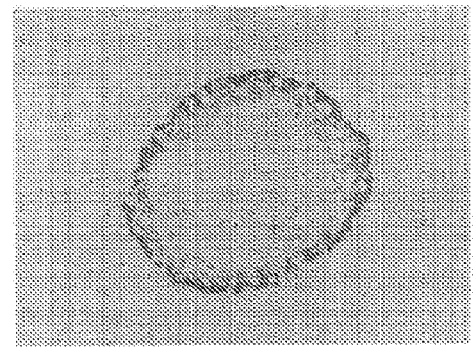
PFC/PC = 18.8
FIG. 1E-1    FIG. 1E-2
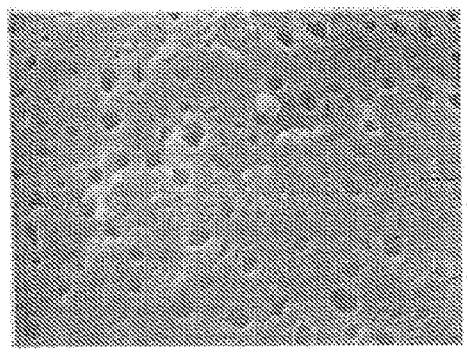 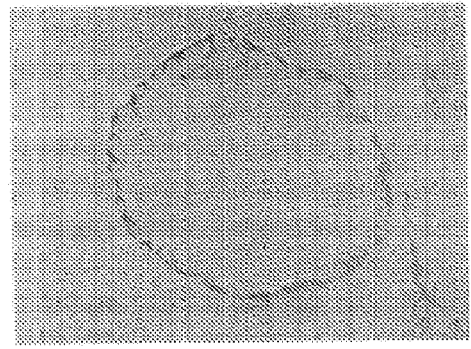
PFC/PC = 44.7
FIG. 1F-1    FIG. 1F-2

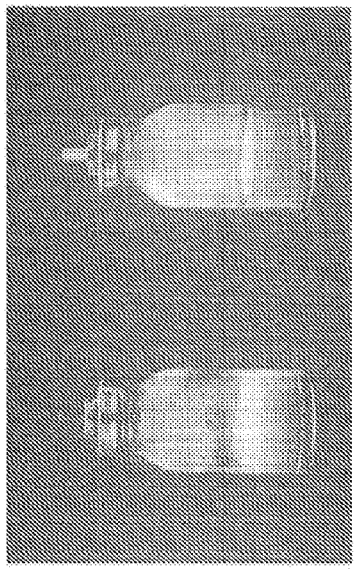
FIG. 3A T = 0
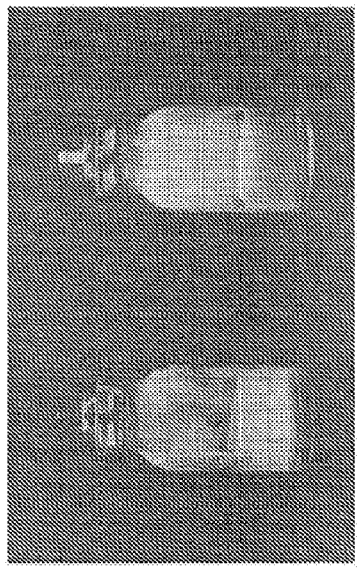
FIG. 3B 30 Sec
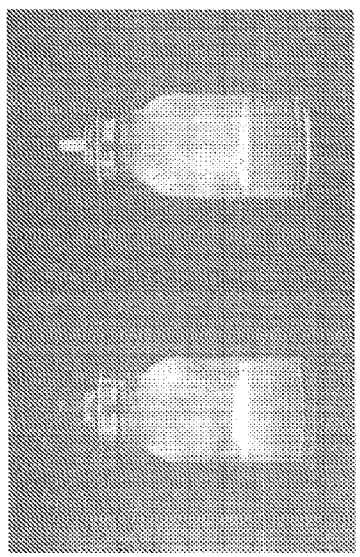
FIG. 3C
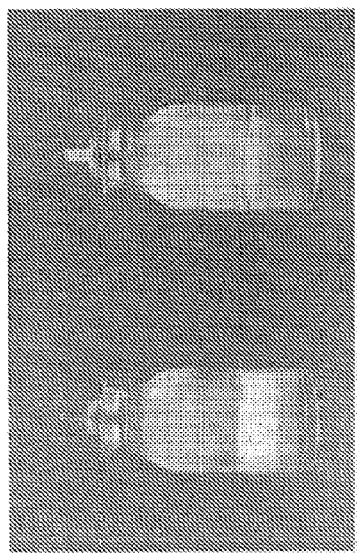
FIG. 3D 2 Hrs

RESPIRATORY DISPERSION FOR METERED DOSE INHALERS COMPRISING PERFORATED MICROSTRUCTURES

CROSS-REFERENCE

The present application is a divisional of U.S. patent application Ser. No. 12/012,827 which was filed Feb. 5, 2008, which is a continuation of U.S. patent application Ser. No. 10/644,265 filed Aug. 19, 2003, which is a continuation of U.S. patent application Ser. No. 09/862,764 filed May 21, 2001, which is a continuation of U.S. patent application Ser. No. 09/218,212 filed Dec. 22, 1998, which is a continuation of PCT Application No. PCT/US98/20615, filed Sep. 29, 1998, which is a continuation-in-part of U.S. patent application Ser. No. 09/133,848, filed Aug. 14, 1998, which is a continuation-in-part of U.S. patent application Ser. No. 09/106,932 filed Jun. 29, 1998 which claims priority from U.S. Provisional Application Ser. No. 60/060,337, filed Sep. 29, 1997 and now lapsed, all of which are incorporated herein by reference in their entireties.

BACKGROUND

The present invention generally relates to formulations and methods for the administration of bioactive agents to a patient via the respiratory tract. More particularly, the present invention relates to methods, systems and compositions comprising relatively stable dispersions of perforated microstructures in a suspension medium that are preferably administered via aerosolization using pulmonary, nasal, or topical routes.

Targeted drug delivery means are particularly desirable where toxicity or bioavailability of the pharmaceutical compound is an issue. Specific drug delivery methods and compositions that effectively deposit the compound at the site of action potentially serve to minimize toxic side effects, lower dosing requirements and decrease therapeutic costs. In this regard, the development of such systems for pulmonary drug delivery has long been a goal of the pharmaceutical industry.

The three most common systems presently used to deliver drugs locally to the pulmonary air passages are dry powder inhalers (DPIs), metered dose inhalers (MDIs) and nebulizers. MDIs, the most popular method of inhalation administration, may be used to deliver medicaments in a solubilized form or as a dispersion. Typically MDIs comprise a Freon or other relatively high vapor pressure propellant that forces aerosolized medication into the respiratory tract upon activation of the device. Unlike MDIs, DPIs generally rely entirely on the patient's inspiratory efforts to introduce a medicament in a dry powder form to the lungs. Finally, nebulizers form a medicament aerosol to be inhaled by imparting energy to a liquid solution. More recently, direct pulmonary delivery of drugs during liquid ventilation or pulmonary lavage using a fluorochemical medium has also been explored. While each of these methods and associated systems may prove effective in selected situations, inherent drawbacks, including formulation limitations, can limit their use.

Since the introduction of the metered-dose inhaler in the mid 1950s, inhalation has become the most widely used route of administration of bronchodilators and steroids locally to the airways of asthmatic patients. Compared with oral administration of bronchodilators, inhalation via an MDI offers a rapid onset of action and a low incidence of systemic side effects.

The MDI is dependent on the propulsive force of the propellant system used in its manufacture. Traditionally, the propellant system has consisted of a mixture of chlorofluorocarbons (CFCs) which are selected to provide the desired vapor pressure and suspension stability. Currently, CFCs such as Freon 11, Freon 12, and Freon 114 are the most widely used propellants in aerosol formulations for inhalation administration. While such systems may be used to deliver solubilized drug, the selected bioactive agent is typically incorporated in the form of a fine particulate to provide a dispersion. To minimize or prevent the problem of aggregation in such systems, surfactants are often used to coat the surfaces of the bioactive agent and assist in wetting the particles with the aerosol propellant. The use of surfactants in this way to maintain substantially uniform dispersions is said to "stabilize" the suspensions.

Unfortunately, traditional chlorofluorocarbon propellants are now believed to deplete stratospheric ozone and, as a consequence, are being phased out. This, in turn, has led to the development of aerosol formulations for pulmonary drug delivery employing so-called environmentally friendly propellants. Classes of propellants which are believed to have minimal ozone-depletion potential in comparison with CFCs are perfluorinated compounds (PFCs) and hydrofluoroalkanes (HFAs). While selected compounds in these classes may function effectively as biocompatible propellants, many of the surfactants that were effective in stabilizing drug suspensions in CFCs are no longer effective in these new propellant systems. As the solubility of the surfactant in the HFA decreases, diffusion of the surfactant to the interface between the drug particle and HFA becomes exceedingly slow, leading to poor wetting of the medicament particles and a loss of suspension stability. This decreased solubility for surfactants in FIFA propellants is likely to result in decreased efficacy with regard to any incorporated bioactive agent.

More particularly, medicament suspensions in propellants tend to aggregate rapidly. If the particle size of the suspended material cannot be regulated and aggregation takes place, the valve orifice of the aerosol container may clog, rendering the dispensing device inoperative or, if a metering valve is employed, it may be rendered inaccurate. This unwanted aggregation or flocculation may lead to improper dosages which can lead to undesirable results, particularly in the case of highly potent, low dose medicaments. Moreover, particle aggregation also leads to fast creaming or sedimentation of the suspension. The resulting phase separation is generally addressed by vigorously shaking the MDI device immediately before use. However, patient compliance is difficult to control and many commercially available suspensions are so unstable that even slight delays between shaking and use can affect dosage uniformity.

Prior art efforts to overcome the difficulties associated with forming stabilized dispersions using environmentally compatible propellants generally involve the addition of HFA-miscible cosolvents (i.e. ethanol) and/or the inclusion of various surfactant systems. For example, several attempts have dealt with improving suspension stability by increasing the solubility of surface-active agents in the HFA propellants. To this end U.S. Pat. No. 5,118,494, WO 91/11173 and WO 92/00107 disclose the use of HFA soluble fluorinated surfactants to improve suspension stability. Mixtures of HFA propellants with other perfluorinated cosolvents have also been disclosed as in WO 91/04011.

Other attempts at stabilization involved the inclusion of nonfluorinated surfactants. In this respect, U.S. Pat. No. 5,492,688 discloses that some hydrophilic surfactants (with a hydrophilic/lipophilic balance greater than or equal to 9.6) have sufficient solubility in HFAs to stabilize medicament suspensions. Increases in the solubility of conventional nonfluorinated MDI surfactants (e.g. oleic acid, lecithin) can also reportedly be achieved with the use of co-solvents such as alcohols, as set forth in U.S. Pat. Nos. 5,683,677 and 5,605,674, as well as in WO 95/17195. Unfortunately, as with the prior art cosolvent systems previously discussed. merely increasing the repulsion between particles has not proved to be a very effective stabilizing mechanism in nonaqueous dispersions, such as MDI preparations.

In addition to the aforementioned surfactant systems. several other attempts have been made to provide stabilized dispersions in environmentally compatible systems. For example, Canadian Patent Application No. 2,036,844 describes the use of suspensions comprising procaterol encapsulated in thermally denatured albumin. Reportedly, the suspensions provide for controlled release of the encapsulated agent. Another attempt at providing stable systems is described in Canadian Patent Application No. 2,136,704 which discloses medicinal aerosol formulations comprising spray dried products and a hydrogenated propellant. The powders apparently contain low levels of a surface active agent to increase particle repulsion and counterbalance attractive forces. Similarly, PCT international Publication No. 97/44012 describes suspension systems comprising powders incorporating low levels of a surface active agent to create "appropriate repulsive forces" that counterbalance electrostatic attractive forces. Yet another system is described in PCT international Publication No. 97/36574 which discusses the use of powders in metered dose inhalers. In these systems it appears that soluble surfactants are added separately to the systems to stabilize the medicament powders. Each of the aforementioned systems is evidently based on the prior art concept that suspension stability is largely achieved by providing repulsive forces that counterbalance the natural particulate attractive forces. Despite such attempts, it is clear that no one has been able to develop a broadly applicable formulation approach that is able to meet the demanding criteria of good dry formulation stability while simultaneously being able to satisfy the ever increasing regulatory standards for MDIs.

Accordingly, it is desirable to have provide methods and preparations that advantageously allow for the efficient delivery of bioactive agents to the pulmonary air passages of a patient in need thereof. It is also desirable to provide stabilized preparations suitable for aerosolization and subsequent administration to the pulmonary air passages of a patient in need thereof. It is still further desirable to provide stabilized dispersions that are compatible for use in a metered dose inhaler and provide reproducible dosing levels over the life of the device.

SUMMARY

A respiratory dispersion for pulmonary delivery comprises one or more bioactive agents, a suspension medium, and a plurality of perforated microstructures having a mean aerodynamic diameter of less than 5 μm. Said suspension medium comprises at least one propellant and permeates said perforated microstructures.

Methods and associated compositions provide for the improved delivery of bioactive agents using stabilized preparations. Preferably, the bioactive agents are in a form for administration to a patient via the respiratory tract. More particularly, the present invention provides for the formation and use of stabilized dispersions (also referred to as stabilized respiratory dispersions) and inhalation systems, including metered dose inhalers comprising such dispersions and individual components thereof. Unlike prior art formulations for targeted drug delivery, the present invention employs novel techniques to reduce attractive forces between the dispersed components and to reduce density differences, thereby retarding degradation of the disclosed dispersions by flocculation, sedimentation or creaming. As such, the disclosed stable preparations facilitate uniform dose delivery by metered dose inhalers, and allow for more concentrated dispersions.

The stabilized preparations of the present invention provide these and other advantages through the use of hollow and/or porous perforated microstructures that substantially reduce attractive molecular forces, such as van der Waals forces, which dominate prior art dispersion preparations. In particular, the use of perforated (or porous) microstructures or microparticulates that are permeated or filled by the surrounding fluid medium, or suspension medium, significantly reduces disruptive attractive forces between the particles. Moreover, the components of the dispersions may be selected to minimize differences in polarizabilities (i.e. reduced Hamaker constant differentials) and further stabilize the preparation. Unlike formulations comprising relatively dense, solid particles or nonporous particles (typically micronized), the dispersions of the present invention are substantially homogeneous with only minor differences in density between particles defined by the perforated microparticulates and the suspension medium.

In addition to the heretofore unappreciated advantages associated with the formation of stabilized preparations, the perforated configuration and corresponding large surface area enables the microstructures to be more easily carried by the flow of gases during inhalation than non-perforated particles of comparable size. This, in turn, enables the perforated microparticles of the present invention to be carried more efficiently into the lungs of a patient than non-perforated structures such as, micronized particles or relatively nonporous microspheres.

In view of these advantages, the dispersions of the present invention are particularly compatible with inhalation therapies comprising administration of the bioactive preparation to at least a portion of the pulmonary air passages. For the purposes of the present application, these stabilized dispersions intended for pulmonary delivery may be termed respiratory dispersions. In particularly preferred embodiments, such respiratory dispersions comprise an environmentally compatible propellant and are used in conjunction with metered dose inhalers to effectively deliver a bioactive agent to the pulmonary air passages or nasal passages of a patient in need thereof.

Accordingly, in preferred embodiments, the invention provides stable respiratory dispersions for the pulmonary or nasal delivery of one or more bioactive agents comprising a suspension medium having dispersed therein a plurality of perforated microstructures comprising at least one bioactive agent, wherein said suspension medium comprises at least one propellant and substantially permeates said perforated microstructures.

For all embodiments of the invention, the perforated microstructures may be formed of any biocompatible material that provides the physical characteristics necessary for the formation of the stabilized dispersions. In this regard, the microstructures comprise pores, voids, defects or other interstitial spaces that allow the fluid suspension medium to freely permeate or perfuse the particulate boundary, thus reducing, or minimizing density differences between the dispersion components. Yet, given these constraints, it will be appreciated that, any material or configuration may be used to form the microstructure matrix. With regard to the selected materials, it is desirable that the microstructure incorporates at least one surfactant. Preferably, this surfactant will comprise a phospholipid or other surfactant approved for pulmonary use. As to the configuration, particularly preferred embodiments of the invention incorporate spray dried hollow microspheres having a relatively thin porous wall defining a large internal void although other void containing or perforated structures are contemplated as well.

Along with the perforated microstructures discussed above, the stabilized dispersions of the present invention further comprise a continuous phase suspension medium. It is an advantage of the present invention that any biocompatible suspension medium having adequate vapor pressure to act as a propellant may be used. Particularly preferred suspension media are compatible with use in a metered dose inhaler. In general, suitable propellants for use in the suspension mediums of the present invention are those propellant gases that can be liquefied under pressure at room temperature and, upon inhalation or topical use are safe, toxicologically innocuous and free of side effects. Further, it is desirable that the selected suspension medium should be relatively non-reactive with respect to the suspended perforated microstructures. In this regard, compatible propellants may generally comprise hydrofluoroalkane propellants. Particularly preferred propellants comprise 1,1,1,2-tetrafluoroethane ($CF_3CH_2F$) (HFA-134a) and 1,1,1,2,3,3,3-heptafluoro-n-propane ($CF_3CHFCF_3$) (HFA-227), perfluoroethane, monochloro-difluoromethane, 1,1-difluoroethane, and combinations thereof.

It will be appreciated that, the present invention further provides methods for forming stabilized dispersions comprising the steps of:

combining a plurality of perforated microstructures comprising at least one bioactive agent with a predetermined volume of suspension medium comprising at least one propellant to provide a respiratory blend wherein said suspension medium permeates said perforated microstructures; and mixing said respiratory blend to provide a substantially homogeneous respiratory dispersion.

As briefly mentioned above (and discussed in more detail below) the stability of the formed dispersions may be further increased by reducing, or minimizing the Hamaker constant differential between the perforated microstructures and the suspension medium. Those skilled in the art will appreciate that, Hamaker constants tend to scale with refractive indices. In this regard, the present invention provides preferred embodiments directed to further stabilizing dispersions by reducing attractive van der Waals forces comprising the steps of:

providing a plurality of perforated microstructures; and combining the perforated microstructures with a suspension medium comprising at least one propellant wherein the suspension medium and the perforated microstructures are selected to provide a refractive index differential value of less than about 0.5.

Along with the formation and stabilization of dispersions, the present invention is further directed to the pulmonary delivery of at least one bioactive agent using a metered dose inhaler. As used herein, the terms "bioactive agent" refers to a substance which is used in connection with an application that is therapeutic or diagnostic in nature such as, methods for diagnosing the presence or absence of a disease in a patient and/or methods for treating disease in a patient. The bioactive agent may be incorporated, blended in, coated on or otherwise associated with the perforated microstructure.

Accordingly, the present invention provides for the use of a propellant in the manufacture of a stabilized dispersion for the pulmonary delivery of a bioactive agent whereby the stabilized dispersion is aerosolized using a metered dose inhaler to provide an aerosolized medicament that is administered to at least a portion of the pulmonary air passages of a patient in need thereof, said stabilized dispersion comprising a suspension medium having dispersed therein a plurality of perforated microstructures comprising at least one bioactive agent wherein the suspension medium comprises at least one propellant and substantially permeates said perforated microstructures.

Yet another aspect of the invention provides methods for the pulmonary delivery of one or more bioactive agents comprising the steps of:

providing a pressurized reservoir containing a stabilized respiratory dispersion comprising a suspension medium having dispersed therein a plurality of perforated microstructures comprising one or more bioactive agents, wherein said suspension medium comprises a propellant and substantially permeates said perforated microstructures;

aerosolizing said respiratory dispersion by releasing pressure on the pressurized reservoir to provide an aerosolized medicament comprising said perforated microstructures; and administering a therapeutically effective amount of said aerosolized medicament to at least a portion of the pulmonary passages of a patient in need thereof.

It will be appreciated that, due to the aerodynamic characteristics preferably afforded by the disclosed perforated microstructures, the present invention is particularly efficient at delivering the selected bioactive agent into the bronchial airways. As such, in another aspect, the invention provides methods for increasing the effective pulmonary deposition of a bioactive agent using a metered dose inhaler comprising the steps of:

associating said bioactive agent with a plurality of perforated microstructures having a mean aerodynamic diameter of less than about 5 µm;

dispersing said perforated microstructures in a suspension medium comprising a propellant to provide a respiratory dispersion; and charging a metered dose inhaler with said respiratory dispersion wherein said charged metered dose inhaler provides a fine particle fraction of greater than approximately 20% w/w upon activation.

With regard to administration, another aspect of the invention is directed to systems for the administration of one or more bioactive agents to a patient. In preferred embodiments, the systems comprise a metered dose inhaler. Accordingly, the present invention further provides systems for the pulmonary administration of a bioactive agent comprising:

a fluid reservoir;

a metering valve operably associated with said fluid reservoir, and a stabilized dispersion in said fluid reservoir wherein said stabilized dispersion comprises a suspension medium having dispersed therein a plurality of perforated microstructures comprising at least one bioactive agent wherein said suspension medium comprises at least one propellant and substantially permeates said perforated microstructures.

As to compatible bioactive agents, those skilled in the art will appreciate that any therapeutic or diagnostic agent may be incorporated in the stabilized dispersions of the present invention. For example, the bioactive agent may be selected from the group consisting of antiallergics, bronchodilators, bronchoconstrictors, pulmonary lung surfactants, analgesics, antibiotics, leukotriene inhibitors or antagonists, anticholinergics, mast cell inhibitors, antihistamines, antiinflammatories, antineoplastics, anesthetics, anti-tuberculars, imaging agents, cardiovascular agents, enzymes, steroids, genetic material, viral vectors, antisense agents, proteins, peptides and combinations thereof. As indicated above, the selected bioactive agent, or agents, may be used as the sole structural component of the perforated microstructures. Conversely, the perforated microstructures may comprise one or more components (i.e. structural materials, surfactants, excipients, etc.) in addition to the incorporated bioactive agents. in particularly preferred embodiments, the perforated microstructures will comprise relatively high concentrations of surfactant (greater than about 10% w/w) along with the incorporated bioactive agent(s).

As such, another aspect of the invention provides for respiratory dispersions for the pulmonary delivery of one or more bioactive agents comprising a suspension medium having dispersed therein a plurality of microparticles comprising greater than about 20% w/w surfactant and at least one bioactive agent wherein said suspension medium comprises at least one propellant. Those skilled in the art will appreciate that, due to their other physiochemical characteristics, the morphology of the incorporated high surfactant particulates may vary without substantially destabilizing the dispersion. As such, stabilized dispersions may be formed with such particulates even if they exhibit relatively low porosity or are substantially solid. That is, while preferred embodiments of the present invention will comprise perforated microstructures or microspheres associated with high levels of surfactant, acceptable dispersions may be formed using relatively low porosity particulates of the same surfactant concentration. In this respect, such embodiments are specifically contemplated as being within the scope of the present invention.

In addition to the components mentioned above, the stabilized dispersions may optionally comprise one or more additives to further enhance stability or increase biocompatibility. For example, various surfactants, co-solvents, osmotic agents, stabilizers, chelators, buffers, viscosity modulators, solubility modifiers and salts can be associated with the perforated microstructure, suspension medium or both. The use of such additives will be understood to those of ordinary skill in the art and the specific quantities, ratios, and types of agents can be determined empirically without undue experimentation.

Other objects, features and advantages of the present invention will be apparent to those skilled in the art from a consideration of the following detailed description of preferred exemplary embodiments thereof.

BRIEF DESCRIPTION OF THE DRAWINGS

FIGS. 1A1 to 1F2 illustrate changes in particle morphology as a function of variation in the ratio of fluorocarbon blowing agent to phospholipid (PFC/PC) present in the spray dry feed. The micrographs, produced using scanning electron microscopy and transmission electron microscopy techniques, show that in the absence of FCs, or at low PFC/PC ratios, the resulting spray dried microstructures comprising gentamicin sulfate are neither particularly hollow nor porous. Conversely, at high PFC/PC ratios, the particles contain numerous pores and are substantially hollow with thin walls.

FIG. 2 is a scanning electron microscopy image of perforated microstructures comprising cromolyn sodium illustrating a preferred hollow/porous morphology.

FIGS. 3A to 3D are photographs illustrating the enhanced stability provided by the dispersions of the present invention over time as compared to a commercial cromolyn sodium formulation (Intal, Rhone-Poulenc-Rorer). In the photographs, the commercial formulation on the left rapidly separates while the dispersion on the right, formed in accordance with the teachings herein, remains stable over an extended period.

DESCRIPTION

Figure 2:
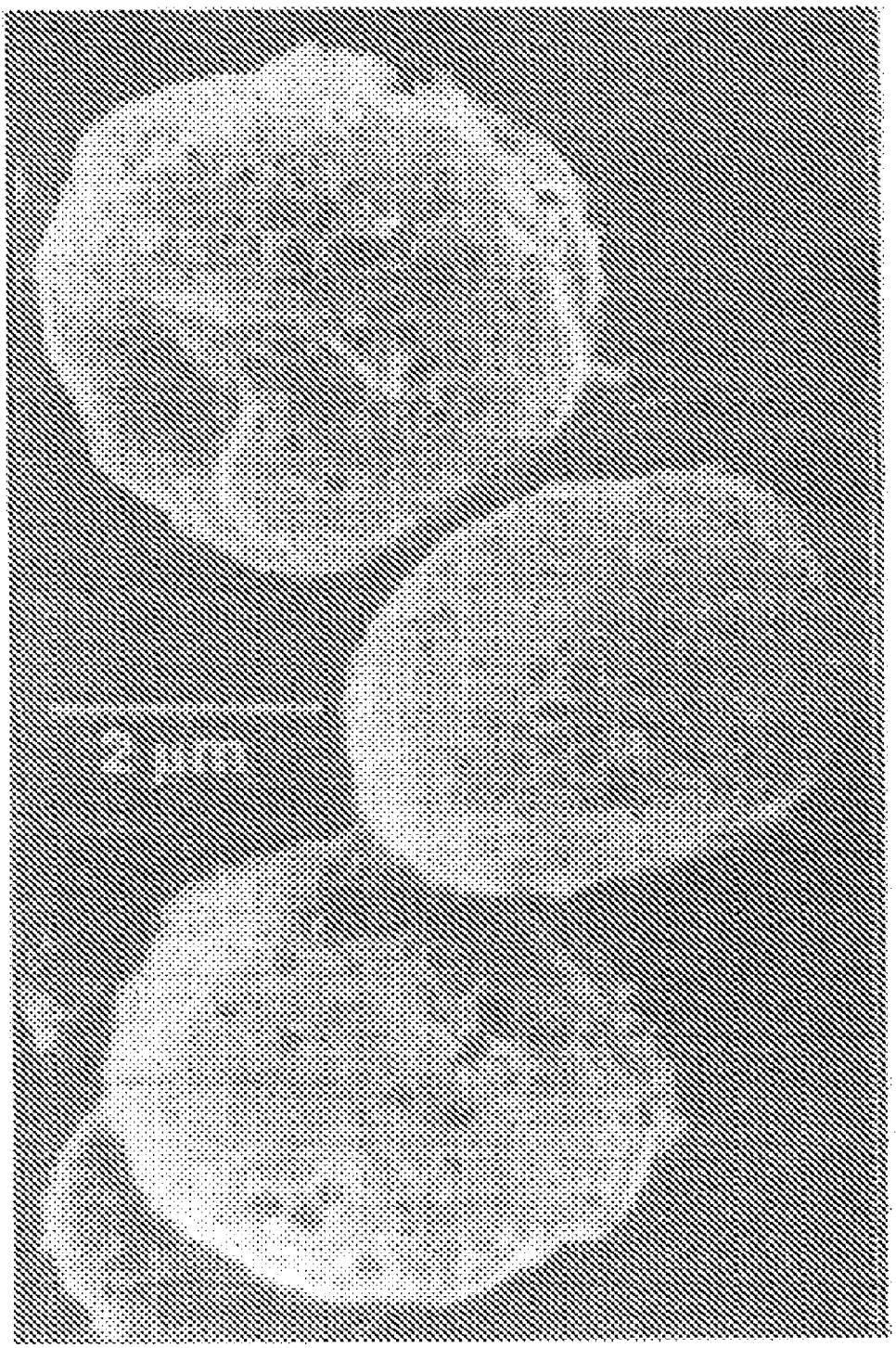

While the present invention may be embodied in many different forms, disclosed herein are specific illustrative embodiments thereof that exemplify the principles of the invention. It should be emphasized that the present invention is not limited to the specific embodiments illustrated.

As set forth above, the present invention provides methods and compositions that allow for the formation of stabilized suspensions that may advantageously be used for the delivery of bioactive agents. The enhanced stability of the suspensions is primarily achieved by lowering the van der Waals attractive forces between the suspended particles, and by reducing the differences in density between the suspension medium and the particles. In accordance with the teachings herein, the increases in suspension stability may be imparted by engineering perforated microstructures which are then dispersed in a compatible suspension medium. In this regard, the perforated microstructures preferably comprise pores, voids, hollows, defects or other interstitial spaces that allow the fluid suspension medium to freely permeate or perfuse the particulate boundary. Particularly preferred embodiments comprise perforated microstructures that are both hollow and porous, almost honeycombed or foam-like in appearance. In especially preferred embodiments the perforated microstructures comprise hollow, porous spray dried microspheres.

With respect to the instant specification, the terms "perforated microstructures" and "perforated microparticles" are used to describe porous products, preferably comprising a bioactive agent, distributed throughout the suspension medium in accordance with the teachings herein. Accordingly, the subject terms may be used interchangeably throughout the instant specification unless the contextual setting indicates otherwise.

When the perforated microstructures are placed in the suspension medium (i.e. propellant), the suspension medium is able to permeate the particles, thereby creating a "homodispersion", wherein both the continuous and dispersed phases are substantially indistinguishable. Since the defined or "virtual" particles (i.e. those comprising the volume circumscribed by the microparticulate matrix) are made up almost entirely of the medium in which they are suspended. the forces driving particle aggregation (flocculation) are minimized. Additionally, the differences in density between the defined particles and the continuous phase are minimized by having the microstructures filled with the medium, thereby effectively slowing particle creaming or sedimentation. As such, the stabilized suspensions of the present invention are particularly compatible with inhalation therapies and may be used in conjunction with metered dose inhalers (MDIs), to improve dose reproducibility, reduce clogging of the MDI valve, increase fine particle fraction, and reduce throat deposition and the resulting side-effects.

Typical prior art suspensions for inhalation therapy comprise solid micronized particles and small amounts (<1% w/w) of surfactant (e.g. lecithin, Span-85, oleic acid) to increase electrostatic repulsion between particles. In sharp contrast, the suspensions of the present invention are designed not to increase repulsion between particles, but rather to decrease the attractive forces between particles. The principal forces driving flocculation in nonaqueous media are van der Waals attractive forces. Van der Waals forces are quantum mechanical in origin, and can be visualized as attractions between fluctuating dipoles (i.e. induced dipole-induced dipole interactions). Dispersion forces are extremely short-range and scale as the sixth power of the distance between atoms. When two macroscopic bodies approach one another the dispersion attractions between the atoms sums up. The resulting force is of considerably longer range, and depends on the geometry of the interacting bodies.

More specifically, for two spherical particles, the magnitude of the van der Waals potential, $V_A$, can be approximated by:

$$V_A = \left( \frac{-A_{\mathit{eff}}}{6H_0} \frac{R_1 R_2}{(R_1 + R_2)} \right),$$

where $A_{\mathit{eff}}$ is the effective Hamaker constant which accounts for the nature of the particles and the medium, $H_0$ is the distance between particles, and $R_1$ and $R_2$ are the radii of spherical particles 1 and 2. The effective Hamaker constant is proportional to the difference in the polarizabilities of the dispersed particles and the suspension medium:

$$A_{\mathit{eff}} = (\sqrt{A_{\mathrm{PART}}} - \sqrt{A_{\mathrm{PART}}})^2,$$

where $A_{SM}$ and $A_{PART}$ are the Hamaker constants for the suspension medium and the particles, respectively. As the suspended particles and the dispersion medium become similar in nature, $A_{SM}$ and $A_{PART}$ become closer in magnitude, and $A_{\mathit{eff}}$ and $V_A$ become smaller. That is, by reducing the differences between the Hamaker constant associated with suspension medium and the Hamaker constant associated with the dispersed particles, the effective Hamaker constant (and corresponding van der Waals attractive forces) may be reduced.

One way to minimize the differences in the Hamaker constants is to create a "homodispersion", that is make both the continuous and dispersed phases essentially indistinguishable as discussed above. In addition to exploiting the morphology of the particles to reduce the effective Hamaker constant, the components of the structural matrix (defining the perforated microstructures) will preferably be chosen so as to exhibit a Hamaker constant relatively close to that of the selected suspension medium. In this respect, one may use the actual values of the Hamaker constants of the suspension medium and the particulate components to determine the compatibility of the dispersion ingredients and provide a good indication as to the stability of the preparation. Alternatively, one could select relatively compatible perforated microstructure components and suspension mediums using readily discernible characteristic physical values that coincide with measurable Hamaker constants.

In this respect, it has been found that the refractive index values of many compounds tend to scale with the corresponding Hamaker constant. Accordingly, easily measurable refractive index values may be used to provide a fairly good indication as to which combination of suspension medium and particle excipients will provide a dispersion having a relatively low effective Hamaker constant and associated stability. It will be appreciated that, since refractive indices of compounds are widely available or easily derived, the use of such values allows for the formation of stabilized dispersions in accordance with the present invention without undue experimentation. For the purpose of illustration only, the refractive indices of several compounds compatible with the disclosed dispersions are provided in Table I immediately below:

TABLE I

| Compound | Refractive Index |
|---|---|
| HFA-134a | 1.172 |
| HFA-227 | 1.223 |
| CFC-12 | 1.287 |
| CFC-114 | 1.288 |
| PFOB | 1.305 |
| Mannitol | 1.333 |
| Ethanol | 1.361 |
| n-octane | 1.397 |
| DMPC | 1.43 |
| Pluronic F-68 | 1.43 |
| Sucrose | 1.538 |
| Hydroxyethylstarch | 1.54 |
| Sodium chloride | 1.544 |

Consistent with the compatible dispersion components set forth above, those skilled in the art will appreciate that, the formation of dispersions wherein the components have a refractive index differential of less than about 0.5 is preferred. That is, the refractive index of the suspension medium will preferably be within about 0.5 of the refractive index associated with the perforated particles or microstructures. It will further be appreciated that, the refractive index of the suspension medium and the particles may be measured directly or approximated using the refractive indices of the major component in each respective phase. For the perforated microstructures, the major component may be determined on a weight percent basis. For the suspension medium, the major component will typically be derived on a volume percentage basis. In selected embodiments of the present invention the refractive index differential value will preferably be less than about 0.45, about 0.4, about 0.35 or even less than about 0.3. Given that lower refractive index differentials imply greater dispersion stability, particularly preferred embodiments comprise index differentials of less than about 0.28, about 0.25, about 0.2, about 0.15 or even less than about 0.1. It is submitted that a skilled artisan will be able to determine which excipients are particularly compatible without undue experimentation given the instant disclosure. The ultimate choice of preferred excipients will also be influenced by other factors, including biocompatibility, regulatory status, ease of manufacture, cost.

In contrast to prior art attempts to provide stabilized suspensions which require excipients (i.e. surfactants) that are soluble in the suspension medium, the present invention provides for stabilized dispersions, at least in part, by immobilizing the bioactive agent(s) and excipients within the structural matrix of the hollow, porous microstructures. Accordingly, preferred excipients useful in the present invention are substantially insoluble in the suspension medium. Under such conditions, even surfactants like, for example, lecithin cannot be considered to have surfactant properties in the present invention since surfactant performance requires the amphiphile to be reasonably soluble in the suspension medium. The use of insoluble excipients also reduces the potential for particle growth by Ostwald ripening.

As discussed above, the minimization of density differences between the particles and the continuous phase is largely dependent on the perforated and/or hollow nature of the microstructures, such that the suspension medium constitutes most of the particle volume. As used herein, the term "particle volume" corresponds to the volume of suspension medium that would be displaced by the incorporated hollow/porous particles if they were solid, i.e. the volume defined by the particle boundary. For the purposes of explanation, and as discussed above, these fluid filled particulate volumes may be referred to as "virtual particles." Preferably, the average volume of the bioactive agent/excipient shell or matrix (i.e. the volume of medium actually displaced by the perforated microstructure) comprises less than 70% of the average particle volume (or less than 70% of the virtual particle). More preferably, the volume of the microparticulate matrix comprises less than about 50%, 40%, 30% or even 20% of the average particle volume. Even more preferably, the average volume of the shell/matrix comprises less than about 10%, 5% or 3% of the average particle volume. Those skilled in the art will appreciate that, such a matrix or shell volumes typically contributes little to the virtual particle density which is overwhelmingly dictated by the suspension medium found therein. Of course, in selected embodiments the excipients used to form the perforated microstructure may be chosen so the density of the resulting matrix or shell approximates the density of the surrounding suspension medium.

It will further be appreciated that, the use of such microstructures will allow the apparent density of the virtual particles to approach that of the suspension medium substantially eliminating the attractive van der Waals forces. Moreover, as previously discussed, the components of the microparticulate matrix are preferably selected, as much as possible given other considerations, to approximate the density of suspension medium. Accordingly, in preferred embodiments of the present invention, the virtual particles and the suspension medium will have a density differential of less than about 0.6 g/cm$^3$. That is, the mean density of the virtual particles (as defined by the matrix boundary) will be within approximately 0.6 g/cm$^3$ of the suspension medium. More preferably, the mean density of the virtual particles will be within 0.5, 0.4, 0.3 or 0.2 g/cm$^3$ of the selected suspension medium. In even more preferable embodiments the density differential will be less than about 0.1, 0.05, 0.01, or even less than 0.005 g/cm$^3$.

In addition to the aforementioned advantages, the use of hollow, porous particles allows for the formation of free-flowing dispersions comprising much higher volume fractions of particles in suspension. It should be appreciated that, the formulation of prior art dispersions at volume fractions approaching close-packing generally results in dramatic increases in dispersion viscoelastic behavior. Rheological behavior of this type is not appropriate for MDI applications. Those skilled in the art will appreciate that, the volume fraction of the particles may be defined as the ratio of the apparent volume of the particles (i.e. the particle volume) to the total volume of the system. Each system has a maximum volume fraction or packing fraction. For example, particles in a simple cubic arrangement reach a maximum packing fraction of 0.52 while those in a face centered cubic/hexagonal close packed configuration reach a maximum packing fraction of approximately 0.74. For non-spherical particles or polydisperse systems, the derived values are different. Accordingly, the maximum packing fraction is often considered to be an empirical parameter for a given system.

Here, it was surprisingly found that the porous structures of the present invention do not exhibit undesirable viscoelastic behavior even at high volume fractions, approaching close packing. To the contrary, they remain as free flowing, low viscosity suspensions having little or no yield stress when compared with analogous suspensions comprising solid particulates. The low viscosity of the disclosed suspensions is thought to be due, at least in large part, to the relatively low van der Waals attraction between the fluid-filled hollow, porous particles. As such, in selected embodiments the volume fraction of the disclosed dispersions is greater than approximately 0.3. Other embodiments may have packing values on the order of 0.3 to about 0.5 or on the order of 0.5 to about 0.8, with the higher values approaching a close packing condition. Moreover, as particle sedimentation tends to naturally decrease when the volume fraction approaches close packing, the formation of relatively concentrated dispersions may further increase formulation stability.

Although the methods and compositions of the present invention may be used to form relatively concentrated suspensions, the stabilizing factors work equally well at much lower packing volumes and such dispersions are contemplated as being within the scope of the instant disclosure. In this regard, it will be appreciated that, dispersions comprising low volume fractions are extremely difficult to stabilize using prior art techniques. Conversely, dispersions incorporating perforated microstructures comprising a bioactive agent as described herein are particularly stable even at low volume fractions. Accordingly, the present invention allows for stabilized dispersions, and particularly respiratory dispersions, to be formed and used at volume fractions less than. 0.3. In some preferred embodiments, the volume fraction is approximately 0.0001-0.3, more preferably 0.001-0.01. Yet other preferred embodiments comprise stabilized suspensions having volume fractions from approximately 0.01 to approximately 0.1.

The perforated microstructures of the present invention may also be used to stabilize dilute suspensions of micronized bioactive agents. In such embodiments the perforated microstructures may be added to increase the volume fraction of particles in the suspension, thereby increasing suspension stability to creaming or sedimentation. Further, in these embodiments the incorporated microstructures may also act in preventing close approach (aggregation) of the micronized drug particles. It should be appreciated that, the perforated microstructures incorporated in such embodiments do not necessarily comprise a bioactive agent. Rather, they may be formed exclusively of various excipients, including surfactants.

As indicated throughout the instant specification, the dispersions of the present invention are preferably stabilized. In a broad sense, the term "stabilized dispersion" will be held to mean any dispersion that resists aggregation, flocculation or creaming to the extent required to provide for the effective delivery of a bioactive agent. While those skilled in the art will appreciate that there are several methods that may be used to assess the stability of a given dispersion, a preferred method for the purposes of the present invention comprises determination of creaming or sedimentation time. In this regard, the creaming time shall be defined as the time for the suspended drug particulates to cream to ½ the volume of the suspension medium. Similarly, the sedimentation time may be defined as the time it takes for the particulates to sediment in ½ the volume of the liquid medium. One relatively simple way to determine the creaming time of a preparation is to provide the particulate suspension in a sealed glass vial. The vials are agitated or shaken to provide relatively homogeneous dispersions which are then set aside and observed using appropriate instrumentation or by visual inspection. The time necessary for the suspended particulates to cream to ½ the volume of the suspension medium (i.e., to rise to the top half of the suspension medium), or to sediment within ½ the volume (i.e., to settle in the bottom ½ of the medium), is then noted. Suspension formulations having a creaming time greater than 1 minute are preferred and indicate suitable stability. More preferably, the stabilized dispersions comprise creaming times of greater than 1, 2, 5, 10, 15, 20 or 30 minutes. In particularly preferred embodiments, the stabilized dispersions exhibit creaming times of greater than about 1, 1.5, 2, 2.5, or 3 hours. Substantially equivalent periods for sedimentation times are indicative of compatible dispersions.

Regardless of the ultimate composition or precise creaming time, the stabilized respiratory dispersions of the present invention preferably comprise a plurality of perforated microstructures, or microparticulates that are dispersed or suspended in the suspension medium. In such cases, the perforated microstructures comprise a structural matrix that exhibits, defines or comprises voids, pores, defects, hollows, spaces, interstitial spaces, apertures, perforations or holes that allows the surrounding suspension medium, to freely permeate, fill or pervade the microstructure. The absolute shape (as opposed to the morphology) of the perforated microstructure is generally not critical and any overall configuration that provides the desired stabilization characteristics is contemplated as being within the scope of the invention. Accordingly, preferred embodiments can comprise approximately microspherical shapes. However, collapsed, deformed or fractured particulates are also compatible. With this caveat, it will be appreciated that, particularly preferred embodiments of the invention comprise spray dried hollow, porous microspheres.

In order to maximize dispersion stability and optimize distribution upon administration, the mean geometric particle size of the perforated microstructures is preferably about 0.5-50 µm, more preferably 1-30 µm. It will be appreciated that, large particles (i.e. greater than 50 µm) should not be used as large particles may tend to aggregate, separate from the suspension and clog the valve or orifice of the container. In especially preferred embodiments, the mean geometric particle size (or diameter) of the perforated microstructures is less than 20 µm or less than 10 µm. More preferably, the mean geometric diameter is less than about 5 µm, and even more preferably, less than about 2.5 µm. In especially preferred embodiments, the perforated microstructures will comprise a powder of dry, hollow, porous microspherical shells of approximately 1 to 10 µm in diameter, with shell thicknesses of approximately 0.1 µm to approximately 0.5 µm. It is a particular advantage of the present invention that the particulate concentration of the dispersions and structural matrix components can be adjusted to optimize the delivery characteristics of the selected particle size.

As discussed throughout the instant specification, the porosity of the microstructures may play a significant part in establishing dispersion stability. In this respect, the mean porosity of the perforated microstructures may be determined through electron microscopy coupled with modern imaging techniques. More specifically, electron micrographs of representative samples of the perforated microstructures may be obtained and digitally analyzed to quantify the porosity of the preparation. Such methodology is well known in the art and may be undertaken without undue experimentation.

For the purposes of the present invention, the mean porosity (i.e. the percentage of the particle surface area that is open to the interior and/or a central void) of the perforated microstructures may range from approximately 0.5% to approximately 80%. In more preferred embodiments, the mean porosity will range from approximately 2% to approximately 40%. Based on selected production parameters, the mean porosity may be greater than approximately, 2%, 5%, 10%, 15%, 20%, 25% or 30% of the microstructure surface area. In other embodiments, the mean porosity of the microstructures may be greater than about 40%, 50%, 60%, 70% or even 80%. As to the pores themselves, they typically range in size from about 5 nm to about 400 nm, with mean pore sizes preferably in the range of from about 20 nm, to about 200 nm. In particularly preferred embodiments, the mean pore size will be in the range of from about 50 nm to about 100 nm. As may be seen in FIGS. 1A1 to 1F2, and discussed in more detail below, it is a significant advantage of the present invention that the pore size and porosity may be closely controlled by careful selection of the incorporated components and production parameters.

Along with the geometric configuration, the perforated or porous and/or hollow design of the microstructures also plays an important role in the resulting aerosol properties upon activation of the MDI. In this respect, the perforated structure and relatively high surface area of the dispersed microparticles enables them to be carried along in the flow of gases during inhalation with greater ease for longer distances than non-perforated particles of comparable size. Because of their high porosity, the density of the particles is significantly less than 1.0 g/cm$^3$, typically less than 0.5 g/cm$^3$, more often on the order of 0.1 g/cm$^3$ and as low as 0.01 g/cm$^3$. Unlike the geometric particle size, the aerodynamic particle size, $d_{aer}$, of the perforated microstructures depends substantially on the particle density, $\rho$: $d_{aer}=d_{geo}\sqrt{\rho}$, where $d_{geo}$ is the geometric diameter. For a particle density of 0.1 g/cm$^3$, $d_{aer}$ will be roughly three times smaller than $d_{geo}$, leading to increased particle deposition into the peripheral regions of the lung and correspondingly less deposition in the throat. In this regard, the mean aerodynamic diameter of the perforated microstructures is preferably less than about 5 µm, more preferably less than about 3 µm, and, in particularly preferred embodiments, less than about 2 µm. Such particle distributions will act to increase the deep lung deposition of the administered agent.

As will be shown subsequently in the Examples, the particle size distribution of the aerosol formulations of the present invention are measurable by conventional techniques such as, for example, cascade impaction or by time of flight analytical methods. Determination of the emitted dose in pressurized inhalations was done according to the proposed U.S. Pharmacopeia method (Pharmacopeial Previews, 22 (1996) 3065) which is incorporated herein by reference. These and related techniques enable the "fine particle fraction" of the aerosol, which corresponds to those particulates that are likely to effectively deposited in the lung, to be calculated. As used herein the phrase "fine particle fraction" refers to the percentage of the total amount of active medicament delivered per actuation from the mouthpiece onto plates 2-7 of an 8 stage Andersen cascade impactor. Based on such measurements, the formulations of the present invention will preferably have a fine particle fraction of approximately 20% or more by weight of the perforated microstructures (w/w). More preferably, they will exhibit a fine particle fraction of from about 25% to 80% w/w, and even more preferably from about 30 to 70% w/w. In selected embodiments the present invention will preferably comprise a fine particle fraction of greater than about 30%, 40%, 50%, 60%, 70% or 80% by weight.

Further, it has also been found that the formulations of the present invention exhibit relatively low deposition rates, when compared with prior art preparations, on the induction port and onto plates 0 and 1 of the impactor. Deposition on these components is linked with deposition in the throat in humans. More specifically, commercially available CFC inhalers have simulated throat depositions of approximately 40-70% (w/w) of the total dose, while the formulations of the present invention typically deposit less than about 20% w/w. Accordingly, preferred embodiments of the present invention have simulated throat depositions of less than about 40%, 35%, 30%, 25%, 20%, 15% or even 10% w/w. Those skilled in the art will appreciate that, significant decrease in throat deposition provided by the present invention will result in a corresponding decrease in associated local side-effects such as, throat irritation and candidiasis.

With respect to the advantageous deposition profile provided by the instant invention, it is well known that MDI propellants typically force suspended particles out of the device at a high velocity towards the back of the throat. Since prior art formulations typically contain a significant percentage of large particles and/or aggregates, as much as two-thirds or more of the emitted dose may impact the throat. Yet, as discussed above, the stabilized dispersions of the present invention result in surprisingly low throat deposition upon administration. While not wishing to be bound by any particular theory, it appears that the reduced throat deposition provided by the instant invention results from decreases in particle aggregation and from the hollow and/or porous morphology of the incorporated microstructures. That is, the hollow and porous nature of the dispersed microstructures slows the velocity of particles in the propellant stream, just as a hollow/porous whiffle ball travels slower than a baseball. Thus, rather than impacting and sticking to the back of the throat, the relatively slow traveling particles are subject to inhalation by the patient. Accordingly, a substantially higher percentage of the administered bioactive agent is deposited in the pulmonary air passages where it may be efficiently absorbed.

Whatever configuration and/or size distribution is ultimately selected for the perforated microstructure, the composition of the defining structural matrix may comprise any one of a number of biocompatible materials. It will be appreciated that, as used herein, the terms "structural matrix" or "microstructure matrix" are equivalent and shall be held to mean any solid material forming the perforated microstructures which define a plurality of voids, apertures, hollows, defects, pores, holes, fissures, etc. that promote the formation of stabilized dispersions as explained above. The structural matrix may be soluble or insoluble in an aqueous environment. In preferred embodiments, the perforated microstructure defined by the structural matrix comprises a spray dried hollow porous microsphere incorporating at least one surfactant. For other selected embodiments the particulate material may be coated one or more times with polymers, surfactants or other compounds which aid suspension.

More generally, the perforated microstructures may be formed of any biocompatible material that is relatively stable and preferably insoluble with respect to the selected suspension medium and can provide the necessary perforated configuration. While a wide variety of materials may be used to form the particles, in particularly preferred embodiments, the structural matrix is associated with, or comprises, a surfactant such as, a phospholipid or fluorinated surfactant. Although not required, the incorporation of a compatible surfactant can improve the stability of the respiratory dispersions, increase pulmonary deposition and facilitate the preparation of the suspension. Moreover, by altering the components, the density of the structural matrix may be adjusted to approximate the density of the surrounding medium and further stabilize the dispersion. Finally, as will be discussed in further detail below, the perforated microstructures preferably comprise at least one bioactive agent.

As set forth above, the perforated microstructures of the present invention may optionally be associated with, or comprise, one or more surfactants. Moreover, miscible surfactants may optionally be combined with the suspension medium liquid phase. It will be appreciated by those skilled in the art that the use of surfactants, while not necessary to practice the instant invention, may further increase dispersion stability, simplify formulation procedures or increase bioavailability upon administration. With respect to MDIs, surfactants further serve to lubricate the metering valve, thereby ensuring consistent reproducibility of valve actuation and accuracy of dose dispersed. Of course combinations of surfactants, including the use of one or more in the liquid phase and one or more associated with the perforated microstructures are contemplated as being within the scope of the invention. By "associated with or comprise" it is meant that the structural matrix or perforated microstructure may incorporate, adsorb, absorb, be coated with or be formed by the surfactant.

In a broad sense, surfactants suitable for use in the present invention include any compound or composition that aids in the formation and maintenance of the stabilized respiratory dispersions by forming a layer at the interface between the structural matrix and the suspension medium. The surfactant may comprise a single compound or any combination of compounds, such as in the case of co-surfactants. Particularly preferred surfactants are substantially insoluble in the propellant, nonfluorinated, and selected from the group consisting of saturated and unsaturated lipids, nonionic detergents, nonionic block copolymers, ionic surfactants, and combinations of such agents. It should be emphasized that, in addition to the aforementioned surfactants, suitable (i.e. biocompatible) fluorinated surfactants are compatible with the teachings herein and may be used to provide the desired stabilized preparations.

Lipids, including phospholipids, from both natural and synthetic sources are particularly compatible with the present invention and may be used in varying concentrations to form the structural matrix. Generally, compatible lipids comprise those that have a gel to liquid crystal phase transition greater than about 40° C. Preferably, the incorporated lipids are relatively long chain (i.e. $C_{16}$-$C_{22}$) saturated lipids and more preferably comprise phospholipids. Exemplary phospholipids useful in the disclosed stabilized preparations comprise egg phosphatidylcholine, dilauroylphosphatidylcholine, dioleoylphosphatidylcholine, dipalmitoylphosphatidylcholine, disteroylphosphatidylcholine, short-chain phosphatidylcholines, phosphatidylethanolamine, dioleoylphosphatidylethanolamine, phosphatidylserine, phosphatidylglycerol, phosphatidylinositol, glycolipids, ganglioside GM1, sphingomyelin, phosphatidic acid, cardiolipin; lipids bearing polymer chains such as, polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein.

Compatible nonionic detergents comprise: sorbitan esters including sorbitan trioleate (SPAN® 85 [2-(4-hydroxy-3-octadec-9-enoyloxy-oxolan-2-yl)-2-octadec-9 enoyloxy-ethyl) octadec-9-enoate—$C_{60}H_{108}O_8$]), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.) which is incorporated herein in its entirety. Preferred block copolymers include diblock and triblock copolymers of polyoxyethylene and polyoxypropylene, including poloxamer 188 (PLURONIC® [methyloxirane-$C_5H_{10}O_2$]F-68 (a mixture of polyoxyethylene and polyoxypropylene)), poloxamer 407 (PLURONIC® F-127), and poloxamer 338. Ionic surfactants such as sodium sulfosuccinate, and fatty acid soaps may also be utilized. In preferred embodiments, the microstructures may comprise oleic acid or its alkali salt.

In addition to the aforementioned surfactants, cationic surfactants or lipids are preferred especially in the case of delivery or RNA or DNA. Examples of suitable cationic lipids include: DOTMA, N-[1-(2,3-dioleyloxy)propyl]-N,N,N-trimethylammonium-chloride; DOTAP, 1,2-dioleyloxy-3-(trimethylammonio)propane; and DOTB, 1,2-dioleyl-3-(4'-trimethylammonio)butanoyl-sn-glycerol. Polycationic amino acids such as polylysine, and polyarginine are also contemplated.

Those skilled in the art will further appreciate that, a wide range of surfactants may optionally be used in conjunction with the present invention. Moreover, the optimum surfactant or combination thereof for a given application can readily be determined by empirical studies that do not require undue experimentation. It will further be appreciated that, the preferred insolubility of any incorporated surfactant in the suspension medium will dramatically decrease the associated surface activity. As such, it is arguable as to whether these materials have surfactant-like character prior to contracting an aqueous bioactive surface (e.g. the aqueous hypophase in the lung). Finally, as discussed in more detail below, surfactants comprising the porous particles may also be useful in the formation of precursor oil-in-water emulsions (i.e. spray drying feed stock) used during processing to form the structural matrix.

Unlike prior art formulations, it has surprisingly been found that the incorporation of relatively high levels of surfactants (i.e. phospholipids) may be used to increase the stability of the disclosed dispersions. That is, on a weight to weight basis, the structural matrix of the perforated microstructures may comprise relatively high levels of surfactant. In this regard, the perforated microstructures will preferably comprise greater than about 1%, 5%, 10%, 15%, 18%, or even 20% w/w surfactant. More preferably, the perforated microstructures will comprise greater than about 25%, 30%, 35%, 40%, 45%, or 50% w/w surfactant. Still other exemplary embodiments will comprise perforated microstructures wherein the surfactant or surfactants are present at greater than about 55%, 60%, 65%, 70%, 75%, 80%, 85%, 90% or even 95% w/w. In selected embodiments the perforated microstructures will comprise essentially 100% w/w of a surfactant such as a phospholipid. Those skilled in the art will appreciate that, in such cases, the balance of the structural matrix (where applicable) will preferably comprise a bioactive agent or non surface active excipients or additives.

While such surfactant levels are preferably employed in perforated microstructures, they may be used to provide stabilized systems comprising relatively nonporous, or substantially solid, particulates. That is, while preferred embodiments will comprise perforated microstructures or microspheres associated with high levels of surfactant, acceptable dispersions may be formed using relatively low porosity particulates of the same surfactant concentration (i.e. greater than about 10% or 20% w/w). In this respect, such embodiments are specifically contemplated as being within the scope of the present invention.

In other preferred embodiments of the invention, the structural matrix defining the perforated microstructure optionally comprises synthetic or natural polymers or combinations thereof. In this respect, useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by selecting the appropriate polymers, the delivery profile of the respiratory dispersion may be tailored to optimize the effectiveness of the bioactive agent.

In addition to the aforementioned polymer materials and surfactants, it may be desirable to add other excipients to an aerosol formulation to improve microsphere rigidity, drug delivery and deposition, shelf-life and patient acceptance. Such optional excipients include, but are not limited to: coloring agents, taste masking agents, buffers, hygroscopic agents, antioxidants, and chemical stabilizers. Further, various excipients may be incorporated in, or added to, the particulate matrix to provide structure and form to the perforated microstructures (i.e. microspheres). These excipients may include, but are not limited to, carbohydrates including monosaccharides, disaccharides and polysaccharides, for example, monosaccharides such as dextrose (anhydrous and monohydrate), galactose, mannitol, D-mannose, sorbitol, sorbose and the like; disaccharides such as, lactose, maltose, sucrose, trehalose and the like; trisaccharides such as, raffinose and the like; and other carbohydrates such as, starches (hydroxyethylstarch), cyclodextrils and maltodextrins. Amino acids are also suitable excipients with glycine preferred. Mixtures of carbohydrates and amino acids are further held to be within the scope of the present invention. The inclusion of both inorganic (e.g. sodium chloride, calcium chloride), organic salts (e.g. sodium citrate, sodium ascorbate, magnesium gluconate, sodium gluconate, tromethamine hydrochloride) and buffers is also contemplated.

Yet other preferred embodiments include perforated microstructures that may comprise, or may be coated with, charged species that prolong residence time at the point of contact or enhance penetration through mucosae. For example, anionic charges are known to favor mucoadhesion while cationic charges may be used to associate the formed microparticulate with negatively charged bioactive agents, such as genetic material. The charges may be imparted through the association or incorporation of polyanionic or polycationic materials such as polyacrylic acids, polylysine, polylactic acid and chitosan.

In addition to, or instead of, the components discussed above, the perforated microstructures will preferably comprise at least one bioactive agent. As used herein, "bioactive agent" refers to a substance which is used in connection with an application that is therapeutic or diagnostic in nature, such as, methods for diagnosing the presence or absence of a disease in a patient and/or in methods for treating a disease in a patient. Particularly preferred bioactive agents for use in accordance with the invention include anti-allergics, peptides and proteins, bronchodilators and anti-inflammatory steroids for use in the treatment of respiratory disorders such as asthma by inhalation therapy.

It will be appreciated that, the perforated microstructures of the present invention may exclusively comprise one or more bioactive agents (i.e. 100% w/w). However, in selected embodiments the perforated microstructures may incorporate much less bioactive agent depending on the activity thereof. Accordingly, for highly active materials the perforated microstructures may incorporate as little as 0.001% by weight although a concentration of greater than about 0.1% w/w is preferred. Other embodiments of the invention may comprise greater than about 5%, 10%, 15%, 20%, 25%, 30% or even 40% w/w bioactive agent. Still more preferably, the perforated microstructures may comprise greater than about 50%, 60%, 70%, 75%, 80% or even 90% w/w bioactive agent. In particularly preferred embodiments, the final stabilized respiratory dispersion desirably contains from about 40%-60% w/w more preferably 50%-70% w/w, and even more preferably 60%-90% w/w of bioactive agent relative to the weight of the microparticulate matrix. The precise amount of bioactive agent incorporated in the stabilized dispersions of the present invention is dependent upon the agent of choice, the required dose, and the form of the drug actually used for incorporation. Those skilled in the art will appreciate that such determinations may be made by using well-known pharmacological techniques in combination with the teachings of the present invention.

Accordingly, bioactive agents that may be administered in the form of aerosolized medicaments in conjunction with the teachings herein include any drug that may be presented in a form which is relatively insoluble in the selected propellant and subject to pulmonary uptake in physiologically effective amounts. Compatible bioactive agents comprise hydrophilic and lipophilic respiratory agents, bronchodilators, antibiotics, antivirals, pulmonary lung surfactants, anti-inflammatories, steroids, antihistaminics, leukotriene inhibitors or antagonists, anticholinergics, antineoplastics, anesthetics, enzymes, cardiovascular agents, genetic material including DNA and RNA, viral vectors, immunoactive agents, imaging agents, vaccines, immunosuppressive agents, peptides, proteins and combinations thereof. Particularly, preferred bioactive agents for administration using aerosolized medicaments in accordance with the present invention include mast cell inhibitors (anti-allergics), bronchodilators, and anti-inflammatory steroids for use in the treatment of respiratory disorders such as asthma by inhalation therapy, for example cromoglycate (e.g. the sodium salt), and albuterol (e.g. the sulfate salt). For systemic delivery (e.g. delivery of the bioactive agent to the systemic circulation for the treatment of autoimmune diseases such as diabetes or multiple sclerosis), peptides and proteins are particularly preferred.

Exemplary medicaments or bioactive agents may be selected from, for example, analgesics, e.g. codeine, dihydromorphine, ergotamine, fentanyl, or morphine; anginal preparations, e.g. diltiazem; mast cell inhibitors, e.g. cromolyn sodium; antiinfectives, e.g. cephalosporins, macrolides, quinolines, penicillins, streptomycin, sulphonamides, tetracyclines and pentamidine; antihistamines, e.g. methapyrilene; anti-inflammatories, e.g. fluticasone propionate, beclomethasone dipropionate, flunisolide, budesonide, tripedane, cortisone, prednisone, prednisolone, dexamethasone, betamethasone, or triamcinolone acetonide; antitussives, e.g. noscapine; bronchodilators, e.g. ephedrine, adrenaline, fenoterol, formoterol, isoprenaline, metaproterenol, salbutamol, albuterol, salmeterol, terbutaline; diuretics, e.g. amiloride; anticholinergics, e.g. ipatropium, atropine, or oxitropium; lung surfactants e.g. Surfaxin, Exosurf, Survanta; xanthines, e.g. aminophylline, theophylline, caffeine; therapeutic proteins and peptides, e.g. DNAse, insulin, glucagon, LHRH, nafarelin, goserelin, leuprolide, interferon, rhu IL-1 receptor, macrophage activation factors such as lymphokines and muramyl dipeptides, opioid peptides and neuropeptides such as enkaphalins, endorphins, renin inhibitors, cholecystokinins, DNAse, growth hormones, leukotriene inhibitors and the like. In addition, bioactive agents that comprise an RNA or DNA sequence, particularly those useful for gene therapy, genetic vaccination, genetic tolerization, or antisense applications, may be incorporated in the disclosed dispersions as described herein. Representative DNA plasmids include pCMVp (available from Genzyme Corp, Framington, Mass.) and pCMV-β-gal (a CMV promoter linked to the *E. coli* Lac-Z gene, which codes for the enzyme β-galactosidase).

The selected bioactive agent(s) may comprise, be associated with, or incorporated in, the perforated microstructures in any form that provides the desired efficacy and is compatible with the chosen production techniques. As used herein, the terms "associate" or "associating" mean that the structural matrix or perforated microstructure may comprise, incorporate, adsorb, absorb, be coated with or be formed by the bioactive agent. Where appropriate, the medicaments may be used in the form of salts (e.g. alkali metal or amine salts or as acid addition salts) or as esters or as solvates (hydrates). In this regard, the form of the bioactive agents may be selected to optimize the activity and/or stability of the medicament and/or to minimize the solubility of the medicament in the suspension medium. It will further be appreciated that, the aerosolized formulations according to the invention may, if desired, contain a combination of two or more active ingredients. The agents may be provided in combination in a single species of perforated microstructure or individually in separate species of perforated microstructures that are combined in the suspension medium. For example, two or more bioactive agents may be incorporated in a single feed stock preparation and spray dried to provide a single microstructure species comprising a plurality of medicaments. Conversely, the individual medicaments could be added to separate stocks and spray dried separately to provide a plurality of microstructure species with different compositions. These individual species could be added to the propellant medium in any desired proportion and placed in the aerosol delivery system as described below. Further, as briefly mentioned above, the perforated microstructures (with or without an associated medicament) may be combined with one or more conventionally micronized bioactive agents to provide the desired dispersion stability.

Based on the foregoing, it will be appreciated by those skilled in the art that a wide variety of bioactive agents may be incorporated in the disclosed stabilized dispersions. Accordingly, the list of preferred bioactive agents above is exemplary only and not intended to be limiting. It will also be appreciated by those skilled in the art that the proper amount of bioactive agent and the timing of the dosages may be determined for the formulations in accordance with already-existing information and without undue experimentation.

As seen from the passages above, various components may be associated with, or incorporated in the perforated microstructures of the present invention. Similarly, several techniques may be used to provide particulates having the appropriate morphology (i.e. a perforated configuration) and density. Among other methods, perforated microstructures compatible with the instant invention may be formed by techniques including lyophilization, spray drying, multiple emulsion, micronization, or crystallization. It will further be appreciated that, the basic concepts of many of these techniques are well known in the prior art and would not, in view of the teachings herein, require undue experimentation to adapt them so as to provide the desired perforated microstructures.

While several procedures are generally compatible with the present invention, particularly preferred embodiments typically comprise perforated microstructures formed by spray drying. As is well known, spray drying is a one-step process that converts a liquid feed to a dried particulate form. With respect to pharmaceutical applications, it will be appreciated that, spray drying has been used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996, which is incorporated herein by reference.

In general, spray drying consists of bringing together a highly dispersed liquid, and a sufficient volume of hot air to produce evaporation and drying of the liquid droplets. The preparation to be spray dried or feed (or feed stock) can be any solution, course suspension, slurry, colloidal dispersion, or paste that may be atomized using the selected spray drying apparatus. Typically, the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. or Niro Corp. will effectively produce particles of desired size. It will further be appreciated that, these spray dryers, and specifically their atomizers, may be modified or customized for specialized applications, i.e. the simultaneous spraying of two solutions using a double nozzle technique. More specifically, a water-in-oil emulsion can be atomized from one nozzle and a solution containing an anti-adherent such as mannitol can be co-atomized from a second nozzle. In other cases, it may be desirable to push the feed solution though a custom designed nozzle using a high pressure liquid chromatography (HPLC) pump provided that microstructures comprising the correct morphology and/or composition are produced. The choice of apparatus is not critical and would be apparent to the skilled artisan in view of the teachings herein.

While the resulting spray-dried powdered particles typically are approximately spherical in shape, nearly uniform in size and frequently are hollow, there may be some degree of irregularity in shape depending upon the incorporated medicament and the spray drying conditions. In many instances the dispersion stability of spray-dried microspheres appears to be more effective if an inflating agent (or blowing agent) is used in their production. Particularly preferred embodiments may comprise an emulsion with the inflating agent as the disperse or continuous phase (the other phase being aqueous in nature). The inflating agent is preferably dispersed with a surfactant solution, using, for instance, a commercially available microfluidizer at a pressure of about 5000 to 15,000 psi. This process forms an emulsion, preferably stabilized by an incorporated surfactant, typically comprising submicron droplets of water immiscible blowing agent dispersed in an aqueous continuous phase. The formation of such dispersions using this and other techniques are common and well known to those in the art. The blowing agent is preferably a fluorinated compound (e.g. perfluorohexane, perfluorooctyl bromide, perfluorodecalin, perfluorobutyl ethane) which vaporizes during the spray-drying process, leaving behind generally hollow, porous aerodynamically light microspheres. As will be discussed in more detail below, other suitable blowing agents include chloroform, Freons, and hydrocarbons. Nitrogen gas and carbon dioxide are also contemplated as a suitable blowing agent.

Although the perforated microstructures are preferably formed using a blowing agent as described above, it will be appreciated that in some instances, no blowing agent is required and an aqueous dispersion of the medicament and surfactant(s) are spray dried directly. In such cases, the formulation may be amenable to process conditions (e.g., elevated temperatures) that generally lead to the formation of hollow, relatively porous microparticles. Moreover, the medicament may possess special physicochemical properties (e.g., high crystallinity, elevated melting temperature, surface activity, etc.) that make it particularly suitable for use in such techniques.

When a blowing agent is employed, the degree of porosity of the perforated microstructure appears to depend, at least in part, on the nature of the blowing agent, its concentration in the feed stock (i.e. as an emulsion), and the spray drying conditions. With respect to controlling porosity, it has surprisingly been found that the use of compounds, heretofore unappreciated as blowing agents, may provide perforated microstructures having particularly desirable characteristics. More particularly, in this novel and unexpected aspect of the present invention it has been found that the use of fluorinated compounds having relatively high boiling points (i.e. greater than about 60° C.) may be used to produce particulates that are especially suitable for inhalation therapies. In this regard, it is possible to use fluorinated blowing agents having boiling points of greater than about 70° C., 80° C., 90° C. or even 95° C. Particularly preferred blowing agents have boiling points greater than the boiling point of water, i.e. greater than 100° C. (e.g. perflubron, perfluorodecalin). In addition, blowing agents with relatively low water solubility ($<10^{-6}$ M) are preferred since they enable the production of stable emulsion dispersions with mean weighted particle diameters less than 0.3 µm. As indicated above, these blowing agents will preferably be incorporated in an emulsified feed stock prior to spray drying. For the purposes of the present invention this feed stock will also preferably comprise one or more bioactive agents, one or more surfactants, or one or more excipients. Of course, combinations of the aforementioned components are also within the scope of the invention.

While not limiting the invention in any way it is hypothesized that, as the aqueous feed component evaporates during spray drying it leaves a thin crust at the surface of the particle. The resulting particle wall or crust formed during the initial moments of spray drying appears to trap any high boiling blowing agents as hundreds of emulsion drop lets (ca. 200-300 nm). As the drying process continues, the pressure inside the particulate increases thereby vaporizing at least part of the incorporated blowing agent and forcing it through the relatively thin crust. This venting or outgassing apparently leads to the formation of pores or other defects in the crust. At the same time, remaining particulate components (possibly including some blowing agent) migrate from the interior to the surface as the particle solidifies. This migration apparently slows during the drying process as a result of increased resistance to mass transfer caused by an increased internal viscosity. Once the migration ceases, the particle solidifies, leaving vesicles, vacuoles or voids where the emulsifying agent resided. The number of pores, their size, and the resulting wall thickness is largely dependent on the nature of the selected blowing agent (i.e. boiling point), its concentration in the emulsion, total solids concentration, and the spray-drying conditions.

It has been surprisingly found that substantial amounts of these relatively high boiling blowing agents may be retained in the resulting spray dried product. That is, the spray dried perforated microstructures may comprise as much as 5%, 10%, 20%, 30% or even 40% w/w of the blowing agent. In such cases, higher production yields were obtained as a result an increased particle density caused by residual blowing agent. It will be appreciated by those skilled in the art that this retained fluorinated blowing agent may alter the surface characteristics of the perforated microstructures and further increase the stability of the respiratory dispersions. Conversely, the residual blowing agent can easily be removed with a post-production evaporation step in a vacuum oven.

Optionally, pores may be formed by spray drying a bioactive agent and an excipient that can be removed from the formed microspheres under a vacuum.

In any event, typical concentrations of blowing agent in the feed stock are between 5% and 100% w/v, and more preferably, between about 20% to 90% w/v. In other embodiments, blowing agent concentrations will preferably be greater than about 10%, 20%, 30%, 40% 50% or even 60% w/v. Yet other feed stock emulsions may comprise 70%, 80%, 90% or even 95% w/v of the selected high boiling point compound.

In preferred embodiments, another method of identifying the concentration of blowing agent used in the feed is to provide it as a ratio of the concentration of the blowing agent to that of the stabilizing surfactant (i.e. phospholipid) in the precursor emulsion. For fluorocarbon blowing agents such as perfluorooctyl bromide and phosphatidylcholine, the ratio may be termed a perfluorocarbon/phosphatidylcholine ratio (or PFC/PC ratio). While phosphatidylcholine is used as an example, it will be appreciated that the appropriate surfactants may be substituted therefor. In any event, the PFC/PC ratio will range from about 1 to about 60 and more preferably, from about 10 to about 50. For preferred embodiments, the ratio will generally be greater than about 5, 10, 20, 25, 30, 40 or even 50. In this respect, FIG. 1 shows a series of pictures taken of perforated microstructures formed of phosphatidylcholine (PC) using various amounts of perfluorooctyl bromide (PFC), a relatively high boiling point fluorocarbon as the blowing agent. The PFC/PC ratios are provided under each subset of pictures, i.e. from IA to IF. Formation and imaging conditions are discussed in greater detail in Examples I and II below. With regard to the micrographs, the column on the left shows the intact microstructures while the column on the right illustrates cross-sections of fractured microstructures from the same preparations.

As may easily be seen in the FIG. 1, the use of higher PFC/PC ratios provides structures of a more hollow and porous nature. More particularly, those methods employing a PFC/PC ratio of greater than about 0.4.8 tended to provide structures that are particularly compatible with the dispersions disclosed herein. Similarly, FIG. 2, a micrograph which will be discussed in more detail in Example IV below, illustrates a preferably porous morphology obtained by using higher boiling point blowing agents (in this case perfluorodecalin).

While relatively high boiling point blowing agents comprise one preferred aspect of the instant invention, it will be appreciated that more conventional blowing or inflating agents may also be used to provide compatible perforated microstructures. Generally, the inflating agent can be any material that will turn to a gas at some point during the spray drying or post-production process. Suitable agents include:

1. Dissolved low-boiling (below 100° C.) solvents with limited miscibility with aqueous solutions, such as methylene chloride, acetone and carbon disulfide used to saturate the solution at room temperature.

2. A gas, e.g. $CO_2$ or $N_2$, used to saturate the solution at room temperature and elevated pressure (e.g. 3 bar). The droplets are then supersaturated with the gas at 1 atmosphere and 100° C.

3. Emulsions of immiscible low-boiling (below 100° C.) liquids such as Freon 113, perfluoropentane, perfluorohexane, perfluorobutane, pentane, butane, FC-11, FC-11B1, FC-11B2, FC-12B2, FC-21, FC-21B1, FC-21B2, FC-31B1, FC-113A, FC-122, FC-123, FC-132, FC-133, FC-141, FC-141B. FC-142. FC-151, FC-152, FC-1112, FC-1121 and FC-1131.

With respect to these lower boiling point inflating agents, they are typically added to the feed stock in quantities of about 1% to 80% w/v of the surfactant solution. Approximately 30% w/v inflating agent has been found to produce a spray dried powder that may be used to form the stabilized dispersions of the present invention.

Regardless of which blowing agent is ultimately selected, it has been found that compatible perforated microstructures may be produced particularly efficiently using a Buchi mini spray drier (model B-191, Switzerland). As will be appreciated by those skilled in the art, the inlet temperature and the outlet temperature of the spray drier are not critical but will be of such a level to provide the desired particle size and to result in a product that has the desired activity of the medicament. In this regard, the inlet and outlet temperatures are adjusted depending on the melting characteristics of the formulation components and the composition of the feed stock. The inlet temperature may thus be between 60° C. and 170° C., with the outlet temperatures of about 40° C. to 120° C. depending on the composition of the feed and the desired particulate characteristics. Preferably, these temperatures will be from 90° C. to 120° C. for the inlet and from 60° C. to 90° C. for the outlet. The flow rate which is used in the spray drying equipment will generally be about 3 ml per minute to about 15 ml per minute. The atomizer air flow rate will vary between values of 1,200 liters per hour to about 3,900 liters per hour. Commercially available spray dryers are well known to those in the art, and suitable settings for any particular dispersion can be readily determined through standard empirical testing, with due reference to the examples that follow. Of course, the conditions may be adjusted so as to preserve biological activity in larger molecules such as proteins or peptides.

Particularly preferred embodiments of the present invention comprise spray drying preparations comprising a surfactant such as a phospholipid and at least one bioactive agent. In other embodiments, the spray drying preparation may further comprise an excipient comprising a hydrophilic moiety such as, for example, a carbohydrate (i.e. glucose, lactose, or starch) in addition to any selected surfactant. In this regard, various starches and derivatized starches suitable for use in the present invention. Other optional components may include conventional viscosity modifiers, buffers such as phosphate buffers or other conventional biocompatible buffers or pH adjusting agents such as acids or bases, and osmotic agents (to provide isotonicity, hyperosmolarity, or hyposmolarity). Examples of suitable salts include sodium phosphate (both monobasic and dibasic), sodium chloride, calcium phosphate, calcium chloride and other physiologically acceptable salts.

Whatever components are selected, the first step in particulate production typically comprises feed stock preparation. Preferably, the selected drug is dissolved in water to produce a concentrated solution. The drug may also be dispersed directly in the emulsion, particularly in the case of water insoluble agents. Alternatively, the drug may be incorporated in the form of a solid particulate dispersion. The concentration of the drug used is dependent on the dose of drug required in the final powder and the performance of the MDI drug suspension (e.g., fine particle dose). As needed, co-surfactants such as poloxamer 188 or span 80 may be added to this annex solution. Additionally, excipients such as sugars and starches can also be added.

In selected embodiments an oil-in-water emulsion is then formed in a separate vessel. The oil employed is preferably a fluorocarbon (e.g., perfluorooctyl bromide, perfluorodecalin) which is emulsified using a surfactant such as a long chain saturated phospholipid. For example, one gram of phospholipid may be homogenized in 150 g hot distilled water (e.g., 60° C.) using a suitable high shear mechanical mixer (e.g., ULTRA-TURRAX™, [a shear mixing instrument], model T-25 mixer) at 8000 rpm for 2 to 5 minutes. Typically 5 to 25 g of fluorocarbon is added dropwise to the dispersed surfactant solution while mixing. The resulting perfluorocarbon in water emulsion is then processed using a high pressure homogenizer to reduce the particle size. Typically the emulsion is processed at 12,000 to 18,000 psi, 5 discrete passes and kept at 50 to 80° C.

The drug solution and perfluorocarbon emulsion are then combined and fed into the spray dryer. Typically the two preparations will be miscible as the emulsion will preferably comprise an aqueous continuous phase. While the bioactive agent is solubilized separately for the purposes of the instant discussion it will be appreciated that, in other embodiments, the bioactive agent may be solubilized (or dispersed) directly in the emulsion. In such cases, the bioactive emulsion is simply spray dried without combining a separate drug preparation.

In any event, operating conditions such as inlet and outlet temperature, feed rate, atomization pressure, flow rate of the drying air, and nozzle configuration can be adjusted in accordance with the manufacturers guidelines in order to produce the required particle size, and production yield of the resulting dry microstructures. Exemplary settings are as follows: an air inlet temperature between 60° C. and 170° C.; an air outlet between 40° C. to 120° C.; a feed rate between 3 ml to about 15 ml per minute; and an aspiration setting of 100% and an atomization, air flow rate between 1,200 to 2,800 L/hr. The selection of appropriate apparatus and processing conditions are well within the purview of a skilled artisan in view of the teachings herein and may be accomplished without undue experimentation. It will be appreciated that, the use of these and substantially equivalent methods provide for the formation of hollow porous aerodynamically light microspheres with particle diameters appropriate for aerosol deposition into the lung.

Along with spray drying the perforated microstructures of the present invention may be formed by lyophilization. Those skilled in the art will appreciate that lyophilization is a freeze-drying process in which water is sublimed from the composition after it is frozen. The particular advantage associated with the lyophilization process is that biologicals and pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of peptides, proteins, genetic material and other natural and synthetic macromolecules in the perforated microstructures without compromising physiological activity. Methods for providing lyophilized particulates are known to those of skill in the art and it would clearly not require undue experimentation to provide dispersion compatible microstructures in accordance with the teachings herein. Accordingly, to the extent that lyophilization processes may be used to provide microstructures having the desired porosity and size they are conformance with the teachings herein and are expressly contemplated as being within the scope of the instant invention.

In addition to the aforementioned techniques, the perforated microstructures of the present invention may also be formed using a double emulsion method. In the double emulsion method the medicament is first dispersed in a polymer dissolved in an organic solvent (e.g. methylene chloride) by sonication or homogenization. This primary emulsion is then stabilized by forming a multiple emulsion in a continuous aqueous phase containing an emulsifier such as polyvinylalcohol. The organic solvent is then removed by evaporation or extraction using conventional techniques and apparatus. The resulting microspheres are washed, filtered and dried prior to combining them with an appropriate suspension medium in accordance with the present invention.

As extensively discussed above, the stabilized dispersions of the present invention further comprise a continuous phase suspension medium. It is an advantage of the present invention that any biocompatible suspension medium having adequate vapor pressure to act as a propellant may be used. Particularly preferred suspension media are compatible with use in a metered dose inhaler. That is, they will be able to form aerosols upon the activation of the metering valve and associated release of pressure. In general, the selected suspension medium should be biocompatible (i.e. relatively non-toxic) and non-reactive with respect to the suspended perforated microstructures comprising the bioactive agent. Preferably, the suspension medium will not act as a substantial solvent for any components incorporated in the perforated microspheres. Selected embodiments of the invention comprise suspension media selected from the group consisting of fluorocarbons (including those substituted with other halogens), hydrofluoroalkanes, perfluorocarbons, hydrocarbons, alcohols, ethers or combinations thereof. It will be appreciated that, the suspension medium may comprise a mixture of various compounds selected to impart specific characteristics.

Particularly suitable propellants for use in the suspension mediums of the present invention are those propellant gases that can be liquefied under pressure at room temperature and, upon inhalation or topical use, are safe, toxicologically innocuous and free of side effects. In this regard, compatible propellants may comprise any hydrocarbon, fluorocarbon, hydrogen-containing fluorocarbon or mixtures thereof having a sufficient vapor pressure to efficiently form aerosols upon activation of a metered dose inhaler. Those propellants typically termed hydrofluoroalkanes or HFAs are especially compatible. Suitable propellants include, for example, short chain hydrocarbons, $C_{1-4}$ hydrogen-containing chlorofluorocarbons such as $CH_2ClF$, $CCl_2F_2CHClF$, $CF_3CHClF$, $CHF_2CClF_2$, $CHClFCHF_2$, $CF_3CH_2Cl$, and $CClF_2CH_3$; $C_{1-4}$ hydrogen-containing fluorocarbons (e.g. HFAs) such as $CHF_2CHF_2$, $CF_3CH_2F$, $CHF_2CH_3$, and $CF_3CHFCF_3$; and perfluorocarbons such as $CF_3CF_3$ and $CF_3CF_2CF_3$. Preferably, a single perfluorocarbon or hydrogen-containing fluorocarbon is employed as the propellant. Particularly preferred as propellants are 1,1,1,2-tetrafluoroethane ($CF_3CH_2F$) (HFA-134a) and 1,1,1,2,3,3,3-heptafluoro-n-propane ($CF_3CHFCF_3$) (HFA-227), perfluoroethane; monochlorodifluoromethane, 1,1-difluoroethane, and combinations thereof. It is desirable that the formulations contain no components that deplete stratospheric ozone. In particular it is desirable that the formulations are substantially free of chlorofluorocarbons such as $CCl_3F$, $CCl_2F_2$, and $CF_3CCl_3$.

Specific fluorocarbons, or classes of fluorinated compounds, that are useful in the suspension media include, but are not limited to, fluoroheptane, fluorocycloheptane, fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluorobutane, fluorocyclobutane, fluoropropane, fluoroethers, fluoropolyethers and fluorotriethylamines. It will be appreciated that, these compounds may be used alone or in combination with more volatile propellants. It is a distinct advantage that such compounds are generally environmentally sound and biologically non-reactive.

In addition to the aforementioned fluorocarbons and hydrofluoroalkanes, various chlorofluorocarbons and substituted fluorinated compounds may also be used as suspension mediums in accordance with the teachings herein. In this respect, FC-11 (CCL3F), FC-11 B (CBrCl2F), FC-11B2 (CBr2ClF), FC 1 2B2 (CF2Br2), FC21 (CHCl2F), FC21B1 (CHBrClF), FC-21B2 (CHBr2F), FC-3 1B1 (CH2BrF), FC-113A (CC13CF3), FC-122 (CClF2CHCl$_2$), FC-123 (CF3CHCl$_2$), FC-132 (CHClFCHClF), FC-133 (CHClFCHF2), FC-141 (CH2ClCHClF), FC-141B (CCl2FCH3), FC-142 (CHF2CH$_2$Cl), FC-151 (CH2FCH$_2$Cl), FC-152 (CH2FCH2F), FC-1112 (CClF=CClF), FC-1121 (CHCl=CFCl) and FC-1131 (CHCl=CHF) are all compatible with the teachings herein despite possible attendant environmental concerns. As such, each of these compounds may be used, alone or in combination with other compounds (i.e. less volatile fluorocarbons) to form the stabilized respiratory dispersions of the present invention.

With respect to possible media combinations, relatively volatile compounds may be mixed with lower vapor pressure components to provide suspension media having specified physical characteristics selected to further improve stability or enhance the bioavailability of the dispersed bioactive agent. In preferred embodiments, the lower vapor pressure compounds will comprise fluorinated compounds (e.g. fluorocarbons) having a boiling point greater than about 25° C. Particularly preferred lower vapor pressure fluorinated compounds for use in the suspension medium may comprise of perfluorooctylbromide $C_8F_{17}Br$ (PFOB or perflubron), dichlorofluorooctane $C_8F_{16}Cl_2$, perfluorooctylethane $C_8F_{17}C_2H_5$ (PFOE), perfluorodecylbromide $C_{10}F_{21}Br$ (PFDB) or perfluorobutylethane $C_4F_9C_2H_5$. Preferably, these lower vapor pressure compounds are present in a relatively low level. Such compounds may be added directly to the suspension medium or may be associated with the perforated microstructures.

Similarly, as indicated above, it is an advantage of the present invention that stabilized dispersions may be formed in HFA or PFC propellants without the use of additional cosolvents or adjuvants. Accordingly, in selected embodiments the formulations are substantially free of potentially reactive liquid components of higher polarity than the propellant employed. This is largely because the presence of cosolvents or adjuvants could potentially increase the solubility of the perforated particles in the suspension medium, thereby altering particle morphology, and particle size (growth by Ostwald ripening) over time. However, depending on the perforated microstructure composition, or the selection of propellant, it may be desirable to include an appropriate cosolvent or adjuvant to adjust vapor pressure or increase administration efficiency. As such, it is expressly contemplated that an HFA propellant containing suspension medium may additionally contain an adjuvant or cosolvent as long as it does not adversely impact the stability of the particles. For example propane, ethanol, isopropyl alcohol, butane, isobutane, pentane, isopentane or a dialkyl ether such as dimethyl ether may be incorporated in the suspension media. Similarly, the suspension medium may contain a volatile fluorocarbon. In general, up to 50% w/w of the propellant may comprise a volatile adjuvant such as a hydrocarbon or fluorocarbon. More preferably, the suspension medium will comprise less than about 40%, 30%, 20% or 10% w/w of cosolvent or adjuvant.

It will further be appreciated that, one of ordinary skill in the art can readily determine other compounds that would perform suitably in the present invention which apparently do not exhibit a desirable vapor pressure and/or viscosity. Rather, it will be understood that, certain compounds outside the preferred ranges of vapor pressure or viscosity can be used if they provide the desired aerosolized medicament upon activation of a MDI.

The stabilized suspensions or dispersions of the present invention may be prepared by dispersal of the microstructures in the selected suspension medium which may then be placed in a container or reservoir. In this regard, the stabilized preparations of the present invention can be made by simply combining the components in sufficient quantity to produce the final desired dispersion concentration. Although the microstructures readily disperse without mechanical energy, the application of energy (e.g., sonication or stirring) to aid in dispersion is expressly contemplated as being within the scope of the invention. Alternatively, the components may be mixed by simple shaking or other type of agitation. The process is preferably carried out under anhydrous conditions to obviate any adverse effects of moisture on suspension stability. Once formed, the dispersion has a reduced susceptibility to flocculation and sedimentation.

The remarkable stability provided by the preparations of the instant invention is graphically illustrated in FIGS. 3A to 3D where a MDI formulation prepared in accordance with the present invention (as will be discussed more fully in Example XVIII below) is compared with a commercially available MDI formulation. In each of the pictures, taken at 0 seconds, 30 seconds, 60 seconds and 2 hours after shaking, the commercial formulation is on the left, and the perforated microstructure dispersion formed accordance with the present invention is on the right. Whereas the commercial cromolyn sodium formulation shows creaming within 30 seconds of mixing, almost no creaming is noted in the spray-dried particles after as long as 2 hours. Moreover, there was little creaming in perforated microstructure formulation after 4 hours (not shown). This example clearly illustrates the stability that can be achieved when the hollow porous particles of compatible materials are filled with the suspension medium (i.e. in the form of a homodispersion).

It will also be understood that, other components can be included in the pharmaceutical compositions of the present invention. For example, osmotic agents, stabilizers, chelators, buffers, hygroscopic agents, viscosity modulators, salts, and sugars can be added to fine tune the stabilized dispersions for maximum life and ease of administration. Such components may be added directly to the suspension medium or associated with, or incorporated in, the dispersed perforated microstructures. Considerations such as sterility, isotonicity, and biocompatibility may govern the use of conventional additives to the disclosed compositions. The use of such agents will be understood to those of ordinary skill in the art and the specific quantities, ratios, and types of agents can be determined empirically without undue experimentation.

Conventional bulk manufacturing methods and machinery well known to those skilled in the art of pharmaceutical manufacture may be employed for the preparation of large scale batches for commercial production of filled canisters, or reservoirs for MDIs. With MDIs for example, in one bulk manufacturing method, a metering valve is crimped onto an aluminum can to provide an empty canister or reservoir. The perforated microparticles are added to a charge vessel, and a liquefied propellant (suspension medium) is pressure-filled through the charge vessel into a manufacturing vessel. The respiratory blend or drug suspension is mixed before recirculation to a filling machine and an aliquot of the stabilized dispersion is then filled through the metering valve into the reservoir. Typically, in batches prepared for pharmaceutical use, each filled canister is check-weighed, coded with a batch number and packed into a tray for storage before release testing.

In other embodiments, the perforated microparticles are introduced into an empty reservoir which is then crimp-sealed to the metering valve. The reservoir or canister is then charged with HFA propellant by over pressure through the valve stem. In yet another embodiment, the stabilized dispersion may be prepared outside the canister or reservoir and then introduced cold filling techniques. The canister is then crimped sealed. Those skilled in the art will appreciated that the filling procedure selected will, at least to some extent, depend on the type of valve chosen.

The canisters generally comprise a container or reservoir capable of withstanding the vapor pressure of the propellant used such as, a plastic or plastic-coated glass bottle, or preferably, a metal can or, for example, an aluminum can which may optionally be anodized, lacquer-coated and/or plastic-coated, wherein the container is closed with a metering valve. The metering valves are designed to deliver a metered amount of the formulation per actuation. The valves incorporate a gasket to prevent leakage of propellant through the valve. The gasket may comprise any suitable elastomeric material such as, for example, low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DFIO, DF30, DF 31/50 ACT, DF60), Bespak plc, LTK (e.g. BK300, BK356) and 3M-Neotechnic Ltd., LIK (e.g. SPRAYMISER™, a heribicide applicator).

Each filled canister is conveniently fitted into a suitable channeling device prior to use to form a metered dose inhaler for administration of the medicament into the lungs or nasal cavity of a patient. Suitable channeling devices comprise for example a valve actuator and a cylindrical or cone-like passage through which medicament may be delivered from the filled canister via the metering valve, to the nose or mouth of a patient e.g., a mouthpiece actuator. Metered dose inhalers are designed to deliver a fixed unit dosage of medicament per actuation such as, for example, in the range of 10 to 5000 micrograms of bioactive agent per actuation. Typically, a single charged canister will provide for tens or even hundreds of shots or doses.

It will be appreciated that, the stabilized preparations for use in metered dose inhalers of the present invention may be advantageously supplied to the physician or other health care professional, in a sterile, prepackaged or kit form. More particularly, the formulations may be supplied as charged MDI reservoirs or canisters, ready for administration. Such kits may contain a number of charged canisters, preferably along with a disposable actuator. In this regard, the patient may then change or substitute canisters during a particular course of treatment. It will also be appreciated that, such kits may include a single charged canister associated or affixed to an actuator, or that the preparation may be supplied in a disposable MDI device.

Administration of bioactive agent may be indicated for the treatment of mild, moderate or severe, acute or chronic symptoms or for prophylactic treatment. Moreover, the bioactive agent may be administered to treat local or systemic conditions or disorders. It will be appreciated that, the precise dose administered will depend on the age and condition of the patient, the particular medicament used and the frequency of administration and will ultimately be at the discretion of the attendant physician. When combinations of bioactive agents are employed, the dose of each component of the combination will generally be the same as that employed for each component when used alone.

As discussed throughout the specification, the stabilized dispersions disclosed herein are preferably administered to the lung or pulmonary air passages of a patient via aerosolization, such as with a metered dose inhaler. MDIs are well known in the art and could easily be employed for administration of the claimed dispersions without undue experimentation. Breath activated MDIs, as well as those comprising other types of improvements which have been, or will be, developed are also compatible with the stabilized dispersions and present invention and, as such, are contemplated as being with in the scope thereof. However, it should be emphasized that, in preferred embodiments, the stabilized dispersions may be administered using a number of different routes including, but not limited to, topical, nasal, pulmonary or oral. Those skilled in the art will appreciate that, such routes are well known and that the dosing and administration procedures may be easily derived for the stabilized dispersions of the present invention.

More efficient delivery of the aerosolized medicament to the bronchial airways has several important clinical implications. Among such advantages are: reduced cost of diagnosis and therapy due to reduction in the amount of aerosolized material required to generate a clinical result; smaller, more effective and more efficient patient dosing at the desired site (i.e., the lung or bronchus); and reduced side effects due to less deposition in the throat. Such advantages may in turn help to increase overall patient compliance.

The foregoing description will be more fully understood with reference to the following Examples. Such Examples, are, however, merely representative of preferred methods of practicing the present invention and should not be read as limiting the scope of the invention.

I Preparation of Hollow Porous Particles of Gentamicin Sulfate by Spray-Drying 40 to 60 ml of the following solutions were prepared for spray drying:

50% w/w hydrogenated phosphatidylcholine, E-100-3 (Lipoid Kg, Ludwigshafen, Germany)

50% w/w gentamicin sulfate (Amresco, Solon, Ohio)

Perfluorooctylbromide, Perflubron (NMK, Japan)

Deionized water

Perforated microstructures comprising gentamicin sulfate were prepared by a spray drying technique using a B-191 Mini Spray-Drier (Buchi, Flawil, Switzerland) under the following conditions: aspiration: 100%, inlet temperature: 85° C.; outlet temperature: 61° C.; feed pump: 10%; $N_2$ flow: 2,800 L/hr. Variations in powder porosity were examined as a function of the blowing agent concentration.

Fluorocarbon-in-water emulsions of perfluorooctyl bromide containing a 1:1 w/w ratio of phosphatidylcholine (PC), and gentamicin sulfate were prepared varying only the PFC/PC ratio. Hydrogenated egg phosphatidylcholine (1.3 grams) was dispersed in 25 mL deionized water using an Ultra-Turrax mixer (model T-25) at 8000 rpm for 2 to 5 minutes (T=60-70° C.). A range from 0 to 40 grams of perflubron was added dropwise during mixing (T=60-70° C.). After addition was complete, the fluorocarbon-in-water emulsion was mixed for an additional period of not less than 4 minutes. The resulting coarse emulsions were then homogenized under high pressure with an Avestin (Ottawa, Canada) homogenizer at 15,000 psi for 5 passes. Gentamicin sulfate was dissolved in approximately 4 to 5 mL deionized water and subsequently mixed with the perflubron emulsion immediately prior to the spray dry process. The gentamicin powders were then obtained by spray drying using the conditions described above. A free flowing, pale yellow powder was obtained from all perflubron containing emulsions. The yield for each of the various formulations ranged from 35% to 60%.

II Morphology of Gentamicin Sulfate Spray-Dried Powders

A strong dependence of the powder morphology, degree of porosity, and production yield was observed as a function of the PFC/PC ratio by scanning electron microscopy (SEM). A series of six SEM micrographs illustrating these observations, labeled 1A1 to 1F1, are shown in the left hand column of FIG. 1. As seen in these micrographs the porosity and surface roughness was found to be highly dependent on the concentration of the blowing agent, where the surface roughness, number and size of the pores increased with increasing PFC/PC ratios. For example, the formulation devoid of perfluorooctyl bromide produced microstructures that appeared to be highly agglomerated and readily adhered to the surface of the glass vial. Similarly, smooth, spherically shaped microparticles were obtained when relatively little (PFC/PC ratio=1.1 or 2.2) blowing agent was used; As the PFC/PC ratio was increased the porosity and surface roughness increased dramatically.

As shown in the right hand column of FIG. 1, the hollow nature of the microstructures was also enhanced by the incorporation of additional blowing agent. More particularly, the series of six micrographs labeled 1A2 to 1F2 show cross sections of fractured microstructures as revealed by transmission electron microscopy (TEM). Each of these images was produced using the same microstructure preparation as was used to produce the corresponding SEM micrograph in the left hand column. Both the hollow nature and wall thickness of the resulting perforated microstructures appeared to be largely dependent on the concentration of the selected blowing agent. That is, the hollow nature of the preparation appeared to increase and the thickness of the particle walls appeared to decrease as the PFC/PC ratio increased. As may be seen in FIGS. 1A2 to 1C2 substantially solid structures were obtained from formulations containing little or no fluorocarbon blowing agent. Conversely, the perforated microstructures produced using a relatively high PFC/PC ratio of approximately 45 (shown in FIG. 1F2 proved to be extremely hollow with a relatively thin wall ranging from about 43.5 to 261 nm.

III Preparation of Hollow Porous Particles of Albuterol Sulfate by Spray-Drying

Hollow porous albuterol sulfate particles were prepared by a spray-drying technique with a B-191 Mini Spray-Drier (Buchi, Flawil, Switzerland) under the following spray conditions: aspiration: 100%, inlet temperature: 85° C.; outlet temperature: 61° C.; feed pump: 10%; $N_2$ flow: 2,800 L/hr. The feed solution was prepared by mixing two solutions A and B immediately prior to spray drying.

Solution A: 20 g of water was used to dissolve Ig of albuterol sulfate (Accurate Chemical, Westbury, N.Y.) and 0.021 g of poloxamer 188 NF grade (BASF, Mount Olive, N.J.).

Solution B: A fluorocarbon-in-water emulsion stabilized by phospholipid was prepared in the following manner. The phospholipid, 1 μg EPC-100-3 (Lipoid KG, Ludwigshafen, Germany), was homogenized in 150 g of hot deionized water (T=50 to 60° C.) using an Ultra-Turrax mixer (model T-25) at 8000 rpm for 2 to 5 minutes (T=60-70° C.). 25 g of perfluorooctyl bromide (Atochem, Paris, France) was added dropwise during mixing. After the fluorocarbon was added, the emulsion was mixed for a period of not less than 4 minutes. The resulting coarse emulsion was then passed through a high pressure homogenizer (Avestin, Ottawa, Canada) at 18,000 psi for 5 passes.

Solutions A and B were combined and fed into the spray-dryer under the conditions described above. A free flowing, white powder was collected at the cyclone separator. The hollow porous albuterol sulfate particles had a volume-weighted mean aerodynamic diameter of 1.18±1.42 μm as determined by a time-of-flight analytical method (Aerosizer, Amherst Process Instruments, Amherst, Mass.). Scanning electron microscopy (SEM) analysis showed the powders to be spherical and highly porous. The tap density of the powder was determined to be less than 0.1 g/cm$^3$.

This foregoing example serves to illustrate the inherent diversity of the present invention as a drug delivery platform capable of effectively incorporating any one of a number of pharmaceutical agents. The principle is further illustrated in the next example.

IV Preparation of Hollow Porous Particles of Cromolyn Sodium by Spray-Drying

Perforated microstructures comprising cromolyn sodium were prepared by a spray-drying technique with a B-191 Mini Spray-Drier (Buchi, Flawil, Switzerland) under the following spray conditions: aspiration: 100%, inlet temperature: 85° C.; outlet temperature: 61° C.; feed pump: 10%; $N_2$ flow: 2,800 L/hr. The feed solution was prepared by mixing two solutions A and B immediately prior to spray drying.

Solution A: 20 g of water was used to dissolve 1 g of cromolyn sodium (Sigma Chemical Co, St. Louis, Mo.) and 0.021 g of poloxamer 188 NF grade (BASF, Mount Olive, N.J.).

Solution B: A fluorocarbon-in-water emulsion stabilized by phospholipid was prepared in the following manner. The phospholipid, 1 g EPC-100-3 (Lipoid KG, Ludwigshafen, Germany), was homogenized in 150 g of hot deionized water (T=50 to 60° C.) using an Ultra-Turrax mixer (model T-25) at 8000 rpm for 2 to 5 minutes (T=60-70° C.). 27 g of perfluorodecalin (Air Products, Allentown, Pa.) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Solutions A and B were combined and fed into the spray dryer under the conditions described above. A free flowing, pale yellow powder was collected at the cyclone separator. The hollow porous cromolyn sodium particles had a volume-weighted mean aerodynamic diameter of 1.23±1.31 μm as determined by a time-of-flight analytical method (Aerosizer, Amherst Process Instruments, Amherst, Mass.). As shown in FIG. 2, scanning electron microscopy (SEM) analysis showed the powders to be both hollow and porous. The tap density of the powder was determined to be less than 0.1 g/cm$^3$.

V Preparation of Hollow Porous Particles of BDP by Spray-Drying

Perforated microstructures comprising beclomethasone dipropionate (BDP) particles were prepared by a spray-drying technique with a B-191 Mini Spray-Drier (Buchi, Flawil, Switzerland) under the following spray conditions: aspiration: 100%, inlet temperature: 85° C.; outlet temperature: 61° C.; feed pump: 10%; $N_2$ flow: 2,800 L/hr. The feed stock was prepared by mixing 0.11 g of lactose with a fluorocarbon-in-water emulsion immediately prior to spray drying. The emulsion was prepared by the technique described below.

74 mg of BDP (Sigma, Chemical Co., St. Louis, Mo.), 0.5 g of EPC-100-3 (Lipoid KG, Ludwigshafen, Germany), 15 mg sodium oleate (Sigma), and 7 mg of poloxamer 188

(BASF, Mount Olive, N.J.) were dissolved in 2 ml of hot methanol. The methanol was then evaporated to obtain a thin film of the phospholipid/steroid mixture. The phospholipid/steroid mixture was then dispersed in 64 g of hot deionized water (T=50 to 60° C.) using an Ultra-Turrax mixer (model T-25) at 8000 rpm for 2 to 5 minutes (T=60-70° C.). 8 g of perflubron (Atochem, Paris, France) was added dropwise during mixing. After the addition was complete, the emulsion was mixed for an additional period of not less than 4 minutes. The resulting coarse emulsion was then passed through a high pressure homogenizer (Avestin, Ottawa, Canada) at 18,000 psi for 5 passes. This emulsion was then used to form the feed stock which was spray dried as described above. A free flowing, white powder was collected at the cyclone separator. The hollow porous BDP particles had a tap density of less than 0.1 g/cm$^3$.

VI Preparation of Hollow Porous Particles of TAA by Spray-Drying

Perforated microstructures comprising triamcinolone acetonide (TAA) particles were prepared by a spray drying technique with a B-191 Mini Spray-Drier (Buchi, Flawil, Switzerland) under the following spray conditions: aspiration: 100%, inlet temperature: 85° C.; outlet temperature: 61° C.; feed pump: 10%; $N_2$ flow: 2,800 L/hr. The feed stock was prepared by mixing 0.57 g of lactose with a fluorocarbon-in-water emulsion immediately prior to spray drying. The emulsion was prepared by the technique described below.

100 mg of TAA (Sigma, Chemical Co., St. Louis, Mo.), 0.56 g of EPC-100-3 (Lipoid KG Ludwigshafen, Germany), 25 mg sodium oleate (Sigma), and 13 mg of poloxamer 188 (BASF, Mount Olive, N.J.) were dissolved in 2 ml of hot methanol. The methanol was then evaporated to obtain a thin film of the phospholipid/steroid mixture. The phospholipid/steroid mixture was then dispersed in 64 g of hot deionized water (T 50 to 60° C.) using an Ultra-Turrax mixer (model T-25) at 8000 rpm for 2 to 5 minutes (T 60-70° C.). 8 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes. This emulsion was then used to form the feed stock which was spray dried as described above. A free flowing, white powder was collected at the cyclone separator. The hollow porous TAA particles had a tap density of less than 0.1 g/cm$^3$.

VII Preparation of Hollow Porous Particles of DNase I by Spray-Drying

Hollow porous DNase I particles were prepared by a spray drying technique with a B-191 Mini Spray-Drier (Buchi, Flawil, Switzerland) under the following conditions: aspiration: 100%, inlet temperature: 80° C.; outlet temperature: 61° C.; feed pump: 10%; $N_2$ flow: 2,800 L/hr. The feed was prepared by mixing two solutions A and B immediately prior to spray drying.

Solution A: 20 g of water was used to dissolve 0.5 gr of human pancreas DNase I (Calbiochem, San Diego Calif.) and 0.012 g of poloxamer 188 NF grade (BASF, Mount Olive, N.J.).

Solution B: A fluorocarbon-in-water emulsion stabilized by phospholipid was prepared in the following way. The phospholipid, 0.52 g EPC-100-3 (Lipoid KG, Ludwigshafen, Germany), was homogenized in 87 g of hot deionized water (T=50 to 60° C.) using an Ultra-Turrax mixer (model T-25) at 8000 rpm for 2 to 5 minutes (T=60-70° C.). 13 g of perflubron (Atochem, Paris, France) was added dropwise during mixing. After the fluorocarbon was added, the emulsion was mixed for at least 4 minutes. The resulting coarse emulsion was then passed through a high pressure homogenizer (Avestin, Ottawa, Canada) at 18,000 psi for 5 passes.

Solutions A and B were combined and fed into the spray dryer under the conditions described above. A free flowing, pale yellow powder was collected at the cyclone separator. The hollow porous DNase I particles had a volume-weighted mean aerodynamic diameter of 1.29±1.40 μm as determined by a time-of-flight analytical method (Aerosizer, Amherst Process Instruments. Amherst, Mass.). Scanning electron microscopy (SEM) analysis showed the powders to be both hollow and porous. The tap density of the powder was determined to be less than 0.1 g/cm$^3$.

The foregoing example further illustrates the extraordinary compatibility of the present invention with a variety of bioactive agents. That is, in addition to relatively small, hardy compounds such as steroids, the preparations of the present invention may be formulated to effectively incorporate larger, fragile molecules such as proteins and genetic material.

VIII Preparation of Hollow Porous Powder by Spray Drying a Gas-in-Water Emulsion The following solutions were prepared with water for injection:

Solution 1: 3.9% w/v m-HES hydroxyethylstarch (Ajinomoto, Tokyo, Japan) 3.25% w/v Sodium chloride (Mallinckrodt, St. Louis, Mo.) 2.83% w/v Sodium phosphate, dibasic (Mallinckrodt, St. Louis, Mo.) 0.42% w/v Sodium phosphate, monobasic (Mallinckrodt, St. Louis, Mo.) Solution 2: 0.45% w/v Poloxamer 188 (BASF, Mount Olive, N.J.) 1.35% w/v Hydrogenated egg phosphatidylcholine, EPC-3 (Lipoid KG, Ludwigshafen, Germany)

The ingredients of solution 1 were dissolved in warm water using a stir plate. The surfactants in solution 2 were dispersed in water using a high shear mixer. The solutions were combined following emulsification and saturated with nitrogen prior to spray drying.

The resulting dry, free flowing, hollow spherical product had a mean particle diameter of 2.6±1.5 μm. The particles were spherical and porous as determined by SEM.

The previous example illustrates the point that a wide variety of blowing agents (here nitrogen) may be used to provide microstructures exhibiting the desired morphology. Indeed, one of the primary advantages of the present invention is the ability to alter formation conditions so as to preserve biological activity (i.e. with proteins), or to produce microstructures having selected porosity.

IX Preparation of Metered Dose Inhalers Containing Hollow Porous Particles

A pre-weighed amount of the hollow porous particles prepared in Examples I, III, IV, V, VI, and VII were placed into 10 ml aluminum cans, and dried in a vacuum oven under the flow of nitrogen for 3-4 hours at 40° C. The amount of powder filled into the can was determined by the amount of drug required for therapeutic effect. After this, the can was crimp sealed using a DF31/50 act 50 μl valve (Valois of America, Greenwich, Conn.) and filled with HFA-13a (DuPont, Wilmington, Del.) propellant by overpressure through the stem. The amount of the propellant in the can was determined by weighing the can before and after the fill.

X Andersen Impactor Test for Assessing MDI Performance

The MDIs prepared in Example IX were then tested using commonly accepted pharmaceutical procedures. The method utilized was compliant with the United State Pharmacopeia (USP) procedure (Pharmacopeial Previews (1996) 22:3065-3098) incorporated herein by reference. After 5 shots to waste, 20 shots from the test MDI were made into an Andersen Impactor.

Extraction procedure. The extraction from all the plates, induction port, and actuator were performed in closed vials with 10 mL of a suitable solvent. The filter was installed but not assayed, because the polyacrylic binder interfered with the analysis. The mass balance and particle size distribution trends indicated that the deposition on the filter was negligibly small. Methanol was used for extraction of beclomethasone dipropionate and triamcinolone acetonide. Deionized water was used for albuterol sulfate, cromolyn sodium, and DNase I. For albuterol MDIs, 0.5 ml of 1 N sodium hydroxide was added to the plate extract, which was used to convert the albuterol into the phenolate form.

Quantitation procedure. All drugs were quantitated by absorption spectroscopy (Beckman DU640 spectrophotometer) relative to an external standard curve with the extraction solvent as the blank. Beclomethasone dipropionate and triamcinolone acetonide were quantitated by measuring the absorption of the plate extracts at 238 nm Albuterol. MDIs were quantified by measuring the absorption of the extracts at 243 nm, while cromolyn sodium was quantitated using the absorption peak at 326 nm. DNase quantitation was done by a protein assay technique using Bio-Rad's microtiter plates (Bio-Rad Protein Assay Dye Reagent Concentrate) against a DNase calibration curve.

Calculation procedure. For each MDI, the mass of the drug in the stem (component −3), actuator (−2), induction port (−1) and plates (0-7) were quantified as described above. The Fine Particle Dose and Fine Particle Fraction was calculated according to the USP method referenced above. Throat deposition was defined as the mass of drug found in the induction port and on plates 0 and 1. The mean mass aerodynamic diameters (MMAD) and geometric standard diameters (GSD) were evaluated by fitting the experimental cumulative function with log-normal distribution by using two-parameter fitting routine. The results of these experiments are presented in subsequent examples.

XI Andersen Cascade Impactor Results for Albuterol MDI Formulations

The results of the cascade impactor test for two commercially available formulations, Proventil HFA and Ventolin and an analogous spray dried hollow porous powder prepared according to Example III are tabulated below. The Alliance formulation was prepared as described in Example IX above. The actuator supplied with Proventil HFA (Key Pharmaceuticals) was used for assessing the performance of the hollow/porous particle MDIs. In all cases the actuator was washed and dried prior to each Andersen Impactor test. The results are presented in Table II immediately below.

TABLE II

Albuterol MDI's

|  | MMAD (GSD) | Throat Deposition, μg | Fine Particle Fraction, % | Fine Particle Dose, μg |
|---|---|---|---|---|
| Proventil ® [Albuterol], HFA (3M Pharm.) 108 μg dose | 2.6 ± 0.1 (2.1 ± 0.3) | 50.5 | 49.0 ± 0.7 | 48.5 ± 0.7 |
| Ventolin ® [Albuterol], CFC (Glaxo Welcome) 108 μg dose | 2.2 ± 0.2 (1.9 ± 0.3) | 58.9 | 43.5 ± 2.6 | 45.3 ± 3.3 |
| Perforated Microstructures, HFA (Alliance Pharm.) 60 μg dose | 3.1 ± 0.2 (1.7 ± 0.01) | 14.9 | 49.0 ± 0.6 | 57.1 ± 05.7 |

Proventil HFA and Ventolin were found to perform very similarly, with a fine particle fraction of .about.45%, throat deposition of .about.55 μg, fine particle dose of .about.47 μg, MMAD of .about.2.4 μm and GSD of 2.0. The MDI formulated with spray dried hollow porous particles had a substantially higher fine particle fraction (.about.80%), and significantly lower throat deposition (15 μg).

XII Andersen Cascade Impactor Results for Albuterol MDI Formulations: Effect of Suspension Concentration on Performance Albuterol sulfate MDI dispersions prepared according to Examples III and IX were studied at different suspension concentrations to determine the effect it may have upon fine particle fraction, MMAD, GSD, and fine particle dose. MDIs containing 0.78% w/w., 0.46% w/w., 0.32% w/w., and 0.25% w/w spray dried hollow porous powders in HFA 134a were studied, and their results are tabulated and presented in Table III below.

TABLE III

Spray-dried hollow porous albuterol sulfate Particles in HFA-134a MDI

| wt % | Fine particle fraction, % | Fine Particle Dose, μg | MMAD | GSD |
|---|---|---|---|---|
| 0.78 | 71 | 61.9 | 3.31 | 1.74 |
| 0.46 | 71 | 37.2 | 3.05 | 1.70 |
| 0.32 | 72 | 25.9 | 3.04 | 1.75 |
| 0.25 | 71 | 22.1 | 3.02 | 1.80 |

Similar performance was observed across the entire concentration range for the MDIs in terms of fine particle fraction, MMAD and GSD. A fine particle dose ranging from 22.1 to nearly 62 μg was observed. These results clearly demonstrate that a wide range of doses can be delivered without any loss in fine particle fraction or any increase in throat deposition. From a practical point of view this may be advantageous for both low and high dose MDI applications.

XIII Andersen Cascade Impactor Results for Cromolyn Sodium MDT Formulations

The results of the cascade impactor tests for a commercially available product (Intal®, Rhone-Poulenc Rorer) and an analogous spray-dried hollow porous powder prepared according to Example IV and IX are shown below in Table IV.

TABLE IV

Cromolyn Sodium MDI's

|  | MMAD (GSD) | Throat Deposition, μg | Fine Particle Fraction, % | Fine Particle Dose, μg |
|---|---|---|---|---|
| Intal ® [$C_{23}H_{16}O_{11}$], CFC (n = 4) (Rhone Poulenc) 800 μg dose | 4.7 ± 0.5 (1.9 ± 0.06) | 629 | 24.3 ± 2.1 | 202 ± 27 |
| Spray dried hollow porous powder, HFA (Alliance) (n = 3) 300 μg dose | 3.4 ± 0.2 (2.0 ± 0.3) | 97 | 67.3 ± 5.5 | 200 ± 11 |

The MDI formulated with perforated microstructures was found to have superior aerosol performance compared with Intal. At a comparable fine particle dose, the spray dried cromolyn formulations possessed a substantially higher fine particle fraction (.about.67%), and significantly decreased throat deposition (6-fold), and a smaller MMAD value. It is important to note that the effective delivery provided for by the present invention allowed for a fine particle dose that was approximately the same as the prior art commercial formulation even though the amount of perforated microstructures administered (300 μg) was roughly a third of the Intal® dose (800 μg) administered.

XIV Andersen Cascade Impactor Results for Beclomethasone Dipropionate MDI Formulations The results of cascade impactor tests for a commercially available formulation (Vanceril, Schering Corp.) and a MDI formulation of an analogous spray-dried hollow porous powder prepared according to Examples V and IX are listed below in Table V.

TABLE V

Beclomethasone Dipropionate MDI's

|  | MMAD (GSD) | Throat Deposition, μg | Fine Particle Fraction, % | Fine Particle Dose, μg |
|---|---|---|---|---|
| Vanceril ® [$C_{28}H_{37}ClO_7$], CFC (n = 4) (Schering) 42 μg dose | 3.47 (2.29) | 32 | 35 ± 2.1 | 17 ± 1.2 |
| Perforated Microstructures, HFA (n = 4) (Alliance) 28 μg dose | 3.75 (1.9) | 12 | 56.3 | 16 ± 0.7 |

At an equivalent fine particle dose, the MDIs formulated with spray dried hollow porous particles were found to have superior aerosol performance compared with Vanceril. The spray dried beclomethasone dipropionate formulations possessed a substantially higher fine particle fraction (56% vs. 35%), and significantly lower throat deposition (3-fold) than Vanceril. The MMAD was found to be slightly higher for the spray dried formulations.

XV Andersen Cascade Impactor Results for Triamcinolone Acetonide MDI Formulations A comparison of a commercial formulation of triamcinolone acetonide (Azmacort, Rhone-Poulenc) and an MDI formulation of hollow porous particles of TAA prepared according to Examples VI and IX are detailed below. Azmacort contains a built-in spacer device to limit steroid deposition in the throat which causes local irritation and candidiasis. The results are shown in Table VI immediately below.

TABLE VI

Throat Respirable Particle

|  | MMAD μg | Device, μg | Throat Deposition μg | Respirable Fraction, % | Fine Particle Dose μg |
|---|---|---|---|---|---|
| Azmacort ®, [triamcinolone acetonide] CFC (Rhone-Poulenc) 200 μg dose, (n = 4) | 6.0 | 133 | 42 | 11.5 ± 23 | 23 |
| Perforated microstructures, HFA 50 μg dose, (Alliance) (n = 4) | 3.4 | 13 | 15 | 45.3 ± 23 | 23 |

Roughly ⅔ of the initial dose of TAA in Azmacort was lost in the spacer device. Approximately ⅔ of the remaining dose was deposited in the throat, with only 11.5% or 23 μg of the initial 200 μg available to the lung. In contrast, the perforated microstructures of the present invention administered without a spacer device deposited an equivalent dose with high efficiency, losing an order of magnitude less material in the device and roughly three times less into the throat. Due to the increased efficiency, four times less TAA is required to deliver the required fine particle dose of 23 μg. These results show that the present formulations can eliminate the need for cumbersome spacer devices in the delivery of steroids to the lung.

XVI Andersen Cascade Impactor Results for DNase I MDI Formulations

The inhalation properties of a MDI formulated as in Example IX with hollow porous particles of DNase I prepared according to Example VII was assessed using an Andersen Cascade impactor. A fine particle fraction of 76%, and MMAD of 3.31 μm were observed. The activity of the spray-dried DNase I powder was assessed for its ability to cleave DNA using gel electrophoresis. No difference was observed between the neat and spray-dried DNase I particles.

XVII Effect of Powder Porosity on MDI Performance

In order to examine the effect powder porosity has upon the suspension stability and aerodynamic diameter, MDIs were prepared with various preparations of perforated microstructures comprising gentamicin formulations as described in Example I. MDIs containing 0.48 wt % spray dried powders in HFA 134a were studied. As set forth in Example I, the spray dried powders exhibit varying porosity. The formulations were filled in clear glass vials to allow for visual examination.

A strong dependence of the suspension stability and mean volume weighted aerodynamic diameter was observed as a function of PFC/PC ratio and/or porosity. The volume weighted mean aerodynamic diameter (VMAD) decreased and suspension stability increased with increasing porosity. The powders that appeared solid and smooth by SEM and TEM techniques had the worst suspension stability and largest mean aerodynamic diameter. MDIs which were formulated with highly porous and hollow perforated microstructures had the greatest resistance to creaming and the smallest aerodynamic diameters. The measured VMAD values for the dry powders produced in Example I are shown in Table VII immediately below.

TABLE VII

| PFC/PC | Powder VMAD, μm |
|---|---|
| 0 | 6.1 |
| 1.1 | 5.9 |
| 2.2 | 6.4 |
| 4.8 | 3.9 |
| 18.8 | 2.6 |
| 44.7 | 1.8 |

XVIII Comparison of Sedimentation Rates in Cromolyn Sodium Formulations

A comparison of the creaming rates of the commercial Intal formulation (Rhone-Poulenc Rorer) and spray-dried hollow porous particles formulated in HFA-134a according to Examples IV and IX (i.e. see FIG. 2) is shown in FIGS. 3A to 3D. In each of the pictures, taken at 0 seconds, 30 seconds, 60 seconds and two hours after shaking, the commercial formulation is on the left and the perforated microstructure dispersion formed accordance with the present invention is on the right. Whereas the commercial Intal formulation shows sedimentation within 30 seconds of mixing, almost no sedimentation is noted in the spray-dried particles after 2 hours. Moreover, there was little sedimentation in perforated microstructure formulation after 4 hours (not shown). This example clearly illustrates the balance in density which can be achieved when the hollow porous particles are filled with the suspension medium (i.e. in the formation of a homodispersion).

Those skilled in the art will further appreciate that, the present invention may be embodied in other specific forms without departing from the spirit or central attributes thereof. In that the foregoing description of the present invention discloses only exemplary embodiments thereof, it is to be understood that, other variations are contemplated as being within the scope of the present invention. Accordingly, the present invention is not limited to the particular embodiments that have been described in detail herein. Rather, reference should be made to the appended claims as indicative of the scope and content of the invention.

What is claimed is:

1. A respiratory dispersion for pulmonary delivery, the respiratory dispersion comprising:
   one or more bioactive agents;
   a suspension medium;
   a plurality of perforated microstructures having a mean aerodynamic diameter of less than 5 μm,
   wherein said suspension medium comprises at least one propellant and permeates said perforated microstructures.

2. The respiratory dispersion of claim 1, wherein said propellant is selected from the group consisting of 1,1,1,2-tetrafluoroethane, 1,1,1,2,3,3,3-heptafluoro-n-propane, perfluoroethane, monochlorodifluoromethane, 1,1-difluoroethane and combinations thereof.

3. The respiratory dispersion of claim 1 wherein said perforated microstructures comprise a surfactant.

4. The respiratory dispersion of claim 3 wherein said surfactant is selected from the group consisting of phospholipids, nonionic detergents, nonionic block copolymers, ionic surfactants, biocompatible fluorinated surfactants and combinations thereof.

5. The respiratory dispersion of claim 3 wherein said surfactant comprises a phospholipid.

6. The respiratory dispersion of claim 5 wherein said phospholipid is selected from the group consisting of dilauroylphosphatidylcholine, dioleylphosphatidylcholine, dipalmitoylphosphatidylcholine, disteroylphosphatidylcholine behenoylphosphatidylcholine, arachidoylphosphatidylcholine and combinations thereof.

7. The respiratory dispersion of claim 1 wherein the mean geometric diameter of the perforated microstructures is between 1 and 5 μm.

8. The respiratory dispersion of claim 1 wherein said bioactive agent is selected from the group consisting of antiallergics, bronchodilators, pulmonary lung surfactants, analgesics, antibiotics, antiinfectives, leukotriene inhibitors or antagonists, antihistamine, antiinflammatories, antineoplastics, antocholinergics, anesthetics, anti-tuberculars, imaging agents, cardiovascular agents, enzymes, steroids, genetic material, viral vectors, antisense agents, proteins, peptides, and combinations thereof.

9. A respiratory dispersion of claim 1 wherein the bioactive agent comprises a bronchodilator.

10. A respiratory dispersion of claim 9 wherein said bronchodilator is selected from ephedrine, adrenaline, fenoterol, formoterol, isoprenaline, metaproterenol, albuterol, salmeterol, and terbutaline.

11. A respiratory dispersion of claim 1 wherein the bioactive agent comprises an anti-inflammatory agent.

12. A respiratory dispersion of claim 11 wherein the anti-inflammatory agent comprises an anti-inflammatory steroid.

13. A respiratory dispersion of claim 12 wherein the anti-inflammatory agent comprises one or more of fluticasone, beclomethasone, flunisolide, budesonide, tripedane, cortisone, prednisone, prednisolone, dexamethoasone, betamethasone or triamcinalone.

14. A respiratory dispersion of claim 1 comprising beclomethasone.

15. A respiratory dispersion of claim 1 comprising formoterol.

16. A respiratory dispersion of claim 1 comprising beclomethasone diproprionate and formoterol.

17. A respiratory dispersion of claim 1 wherein the bioactive agent comprises an anti-cholinergic agent.

18. A respiratory dispersion of claim 17 where the anti-cholinergic agent comprises one or more of ipratropium, atropine, or oxitropium.

19. A respiratory dispersion of claim 9 wherein said bronchodilator is salbutamol.

* * * * *